US009095475B2

(12) United States Patent
Takai et al.

(10) Patent No.: US 9,095,475 B2
(45) Date of Patent: Aug. 4, 2015

(54) APPARATUS AND METHOD FOR MANUFACTURING A TAMPON

(75) Inventors: Masakatsu Takai, Kagawa (JP); Sadami Tabuchi, Kagawa (JP); Satoshi Nozaki, Kagawa (JP); Shinobu Seki, Kagawa (JP); Hideki Onishi, Kagawa (JP); Masashi Hosokawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 945 days.

(21) Appl. No.: 13/056,384

(22) PCT Filed: Jul. 17, 2009

(86) PCT No.: PCT/JP2009/062938
§ 371 (c)(1),
(2), (4) Date: Apr. 14, 2011

(87) PCT Pub. No.: WO2010/013605
PCT Pub. Date: Feb. 4, 2010

(65) Prior Publication Data
US 2011/0179612 A1    Jul. 28, 2011

(30) Foreign Application Priority Data

| Jul. 31, 2008 | (JP) | 2008-198349 |
| Aug. 29, 2008 | (JP) | 2008-222213 |
| Sep. 29, 2008 | (JP) | 2008-251447 |

(51) Int. Cl.
*A61F 13/20* (2006.01)
(52) U.S. Cl.
CPC .................... *A61F 13/2085* (2013.01)
(58) Field of Classification Search
CPC .................................................. A61F 13/2085
USPC ...... 29/771, 783, 791; 28/118, 119; 604/385.1, 385.17–385.18, 904; 264/320; 425/392, 393
See application file for complete search history.

(56) References Cited

U.S. PATENT DOCUMENTS 2,342,680 A * 2/1944 Melzer ............................ 406/76
2,572,942 A   10/1951 Malsbary
(Continued)

FOREIGN PATENT DOCUMENTS

| AU | 655065 | 4/1993 |
| GB | 1469972 | 4/1977 |

(Continued)

OTHER PUBLICATIONS
International Search Report for PCT/JP2009/062938 mailed Oct. 20, 2009.
(Continued)

*Primary Examiner* — David Bryant
*Assistant Examiner* — Steven A Maynard
(74) *Attorney, Agent, or Firm* — Lowe Hauptman & Ham, LLP

(57) ABSTRACT

An apparatus for manufacturing a tampon which includes an absorbent body, an accommodating member and a pushing member, includes: an orienting mechanism; a first inserting mechanism that inserts the pushing member into the accommodating member; and a second inserting mechanism that inserts the absorbent body into the accommodating member in which the pushing member is inserted. The orienting mechanism has an opening through which the accommodating member is inputted; a pair of first protruded parts; and a pair of second protruded parts located on other-end side in the longitudinal direction of the opening and protruding inwardly in an opposing manner into the opening, a gap between the pair of first protruded parts, and a gap between the pair of second protruded parts being greater than the external diameter of the minor diameter part and smaller than the external diameter of the major diameter part.

6 Claims, 38 Drawing Sheets

(56) References Cited

U.S. PATENT DOCUMENTS

| | | | | |
|---|---|---|---|---|
| 3,549,008 A | * | 12/1970 | Anderson | 209/586 |
| 4,302,174 A | | 11/1981 | Hinzmann | |
| 4,321,993 A | * | 3/1982 | Hinzmann et al. | 198/400 |
| 4,500,229 A | * | 2/1985 | Cole et al. | 406/88 |
| 4,561,806 A | * | 12/1985 | Lenhart | 406/88 |

FOREIGN PATENT DOCUMENTS

| | | |
|---|---|---|
| JP | 5014192 | 2/1975 |
| JP | 57173054 | 10/1982 |
| JP | 03-265419 A | 11/1991 |
| JP | 584263 | 4/1993 |
| JP | 2002255335 | 9/2002 |

OTHER PUBLICATIONS

Office Action issued in Chinese Application No. 200980129466.9 dated Dec. 14, 2012, 8 pages.

Office Action issued Jan. 3, 2014, corresponds to European patent application No. 09802848.3.

Office Action issued Apr. 4, 2014, corresponds to Chinese patent application No. 201310142053.2.

Extended European Search Report issued Apr. 11, 2013 corresponds to EP Patent application No. 09802848.3.

Office Action issued Apr. 25, 2013 corresponds to Eurasian patent application No. 201001893.

Office Action dated Aug. 28, 2013, corresponds to Chinese patent application No. 200980129466.9.

Office Action issued Apr. 22, 2014, corresponds to Chinese patent application No. 201310142234.5.

Office Action as mailed on Mar. 5, 2013 in corresponding Japanese Patent Application No. 2008-222213.

Office Action as mailed on Mar. 5, 2013 in corresponding Japanese Patent Application No. 2008-251447.

Office Action as mailed on Mar. 5, 2013 in corresponding Japanese Patent Application No. 2008-198349.

Office Action issued Mar. 12, 2014, corresponds to Chinese patent application No. 200980129466.9.

Notification of the Second Office Action in corresponding Chinese Application No. 201310142053.2 dated Nov. 25, 2014.

* cited by examiner

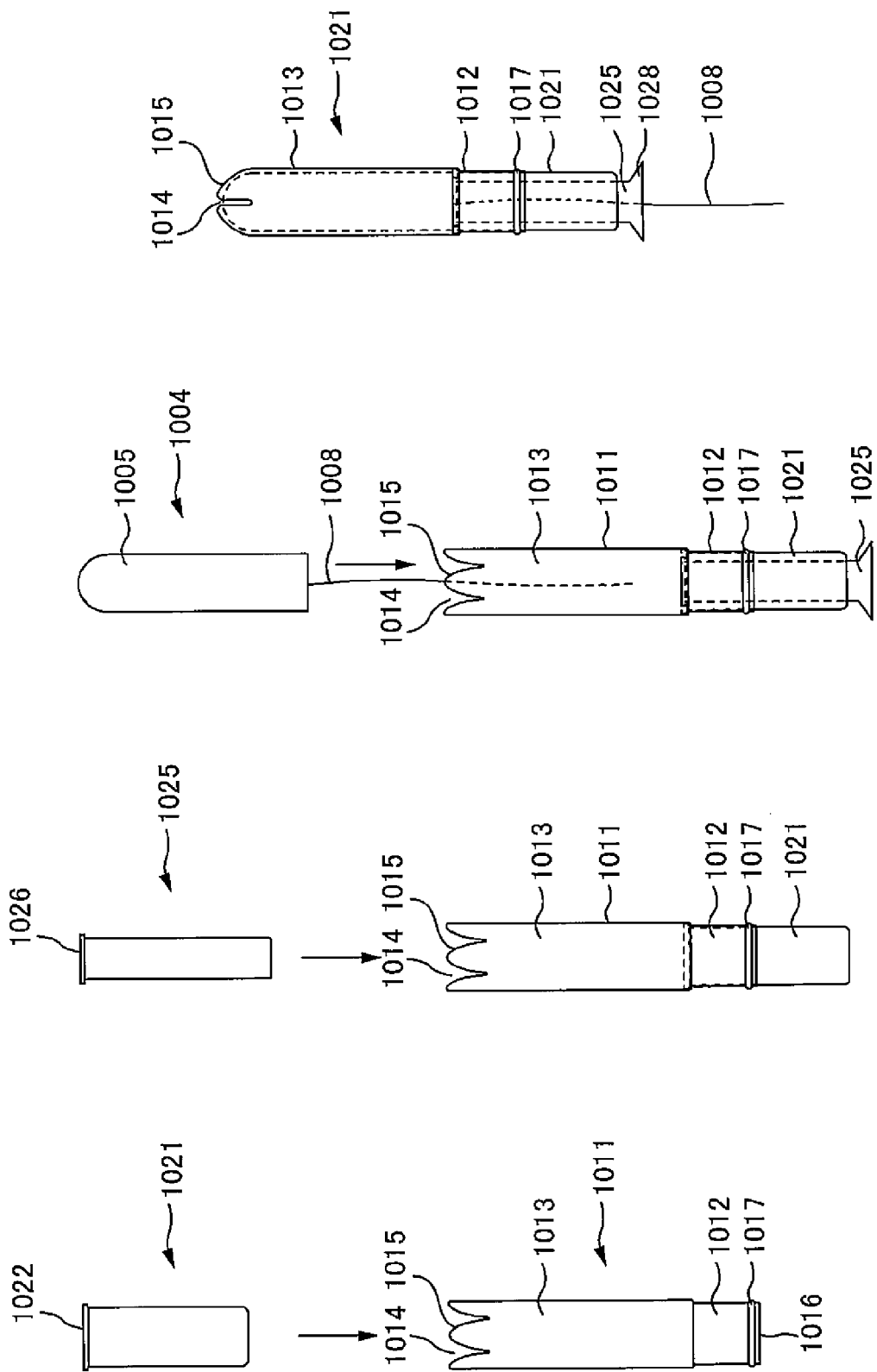

LEADING-END SIDE ←——→ REAR-END SIDE

LEADING-END SIDE ←——→ REAR-END SIDE

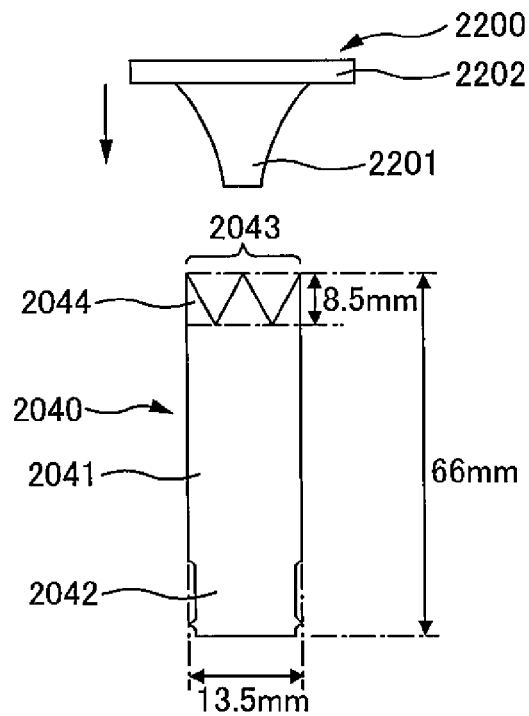
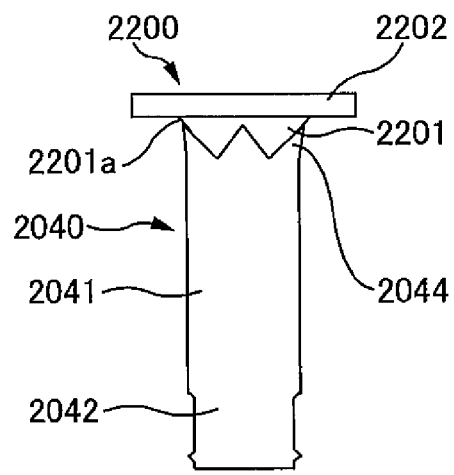
FIG. 25A
FIG. 25B
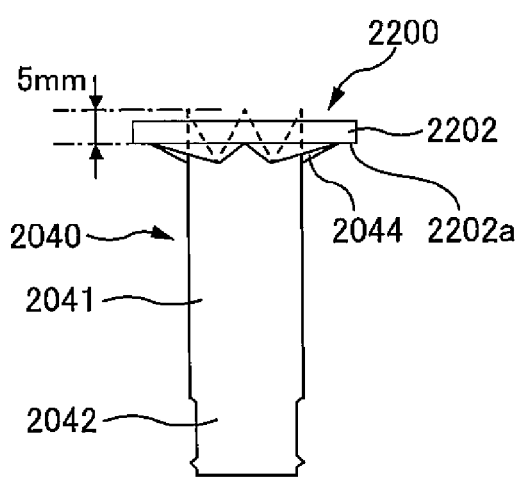
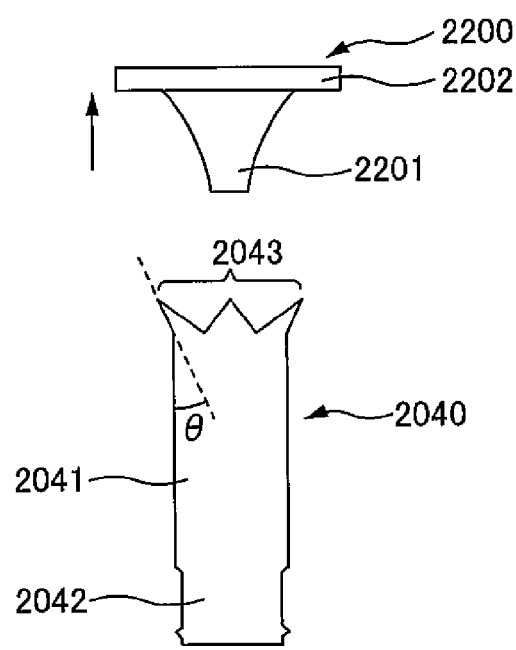
FIG. 25C
FIG. 25D

LEADING-END SIDE ◄─────────► REAR-END SIDE

LEADING-END SIDE ◄─────────► REAR-END SIDE

APPARATUS AND METHOD FOR MANUFACTURING A TAMPON

RELATED APPLICATIONS

The present application is a national phase of PCT/JP2009/062938, filed Jul. 17, 2009 and is based on, and claims priority from, Japanese Application Number 2008-198349, filed Jul. 31, 2008, Japanese Application Number 2008-222213, filed Aug. 29, 2008, and Japanese Application Number 2008-251447, filed Sep. 29, 2008.

TECHNICAL FIELD (Part One)

The present invention relates to an apparatus and method for manufacturing a tampon.

(Part Two)

The present invention relates to a method and apparatus for manufacturing a tampon. Particularly, the present invention relates to a method and apparatus for manufacturing a tampon including a tampon main body, an accommodating cylinder accommodating the tampon main body, the accommodating cylinder having an opening formed at a leading end and a plurality of petaloid parts surrounding the opening, and a pushing member that is movable in the accommodating member and pushes the tampon main body out of the accommodating cylinder through the opening.

(Part Three)

The present invention relates to an apparatus and method for manufacturing a tampon. Particularly, the present invention relates to an apparatus and method of manufacturing a tampon including a tampon main body, an accommodating cylinder that accommodates the tampon main body, and a pushing member that moves in the accommodating cylinder and pushes the tampon main body out of the accommodating cylinder, a plurality of petaloid parts being provided at a one-end part in the longitudinal direction of the accommodating cylinder.

BACKGROUND ART (Part One)

A tampon (sanitary tampon) is known which is inserted into a vaginal cavity in the body and absorbs menstrual blood etc. Such a tampon includes, for example, an absorbent body that absorbs liquid such as menstrual blood, a cylindrical accommodating member that accommodates the absorbent body, and a pushing member that moves inside the accommodating member to push the absorbent body out of the accommodating member. A user of the tampon inserts into the vaginal cavity the accommodating member in which the absorbent body is accommodated and then pushes out the absorbent body using the pushing member. Thus, the absorbent body is guided into the vaginal cavity. Then, the absorbent body that is guided into the vaginal cavity absorbs menstrual blood etc., (see Patent Document 1).

(Part Two)

A tampon including a tampon main body, an accommodating cylinder accommodating the tampon main body, the accommodating cylinder having an opening formed at a leading end and a plurality of petaloid parts surrounding the opening, and a pushing member that is movable in the accommodating member and pushes the tampon main body out of the accommodating cylinder through the opening is widely known as a sanitary product (for example, see Patent Document 1).

A tampon of the above structure is, for example, manufactured by fabricating each item constituting the tampon (i.e., a tampon main body, an accommodating cylinder and a pushing member) and inserting each of the pushing member and the tampon main body into the accommodating cylinder through the opening of the accommodating cylinder.

(Part Three)

A tampon including a tampon main body, an accommodating cylinder that accommodates the tampon main body, and a pushing member that moves in the accommodating cylinder and pushes the tampon main body out of the accommodating cylinder, a plurality of petaloid parts being provided at a one-end part in the longitudinal direction of the accommodating cylinder is widely known as a sanitary product (for example, see Patent Document 1).

The above-mentioned tampon is manufactured by fabricating each of a tampon main body, an above-mentioned and a pushing member that constitutes a tampon and inserting the pushing member and the tampon main body into the accommodating cylinder. Further, a manufacturing apparatus of tampon may include a supplying mechanism that supplies the fabricated accommodating cylinder. The supplying mechanism includes a transport path that transports the accommodating cylinder. As the result of the transportation of the accommodating cylinder by the transport path, the accommodating cylinder is supplied to the predetermined supply destination.

Further, the transport path may include a first transport path that transports the accommodating cylinder in a first transport direction lying along the longitudinal direction of the accommodating cylinder; and a second transport path that receives from the first transport path the accommodating cylinder that has traveled on the first transport path and that transports the accommodating cylinder in a second transport direction intersecting the longitudinal direction of the accommodating cylinder. In such a case, the second transport path includes a receiving part that receives the accommodating cylinder from the first transport path. The accommodating cylinder that has traveled on the first transport path will travel on the second transport path after being received by the receiving part.

RELATED ART DOCUMENTS

Patent Document

Patent document 1: JP-A-05-84263

DISCLOSURE OF INVENTION

Problems to be Solved by the Invention (Part One)

When manufacturing a tampon of the above-mentioned structure, first, components of the tampon (an absorbent body, an accommodating member and a pushing member) are manufactured. Then, the manufactured components are respectively supplied to a transport conveyor etc., and the pushing member and the absorbent body are inserted into the accommodating member, so as to assemble the tampon. In order to assemble the tampon properly, it is necessary to supply each component to the transport conveyor with the component being oriented in a proper predetermined direction.

In consideration of the operability of the tampon, some type of the above-mentioned accommodating member may include a minor diameter part provided on one end thereof, and a major diameter part provided on the other end thereof and having an external diameter that is greater than that of the minor diameter part. With the accommodating member of such a structure, it is difficult to orient it in a predetermined direction and thus it is difficult to supply the accommodating member to the transport conveyor accurately and rapidly.

The present invention has been made in view of such a problem and its object is to supply the accommodating member accurately and rapidly while manufacturing a tampon.

(Part Two)

In order to improve production speed of tampons, it is required to insert the tampon main body and the pushing member smoothly into the accommodating cylinder. However, there are cases where the plurality of petaloid parts provided on the accommodating cylinder is inclined inwardly in the radial direction of the accommodating cylinder due to causes such as impaction between accommodating cylinders. With the plurality of petaloid parts being inwardly inclined in the radial direction of the accommodating cylinder, the opening, which serves as an inserting inlet when inserting the tampon main body and the pushing member, is narrowed. Therefore, it will be difficult to insert the tampon main body and the pushing member into the accommodating cylinder.

The present invention has been made in view of such a problem and its object is to insert the tampon main body and the pushing member smoothly into the accommodating cylinder.

(Part Three)

With above-mentioned structure, if the receiving part receives an accommodating cylinder and further receives an accommodating cylinder when the previous accommodating cylinder is already in the receiving part, there is a possibility that the accommodating cylinders will not be supplied properly. Specifically, if the receiving part receives an accommodating cylinder and further receives an accommodating cylinder when the previous accommodating cylinder is already in the receiving part, the accommodating cylinders will not fit into the second transport path.

In detail, if the receiving part tries to further receive accommodating cylinders with the previous accommodating cylinder being already in the receiving part, a plurality of accommodating cylinders will pile up before the receiving part (that is to say, the terminal end part of the first transport path). At this time, the accommodating cylinders piles up in a direction lying along the longitudinal direction of the accommodating cylinders. Regarding the accommodating cylinders which have piled up as has been described above, there may be an accommodating cylinder each of whose petaloid parts being inclined outwards, and the other accommodating cylinder (specifically, the other end part in the longitudinal direction of the other accommodating cylinder) may fit into such an accommodating cylinder. (For example, see FIG. 45). In other words, if the plurality of accommodating cylinders piles up before the receiving part, the accommodating cylinders may join with each other. Under a situation where the accommodating cylinders are joined with each other, it will be difficult to supply the accommodating cylinders properly.

Accordingly, the present invention has been made in view of such a problem and its object is to supply the accommodating cylinders properly.

Means for Solving the Problems (Part One)

In order to achieve the objects described above, the main aspect of the present invention is:

an apparatus for manufacturing a tampon, the tampon including an absorbent body that absorbs liquid, an accommodating member that is cylindrical and accommodates the absorbent body, and a pushing member that moves inside the accommodating member and pushes the absorbent body out of the accommodating member, the accommodating member including a minor diameter part provided at a one-end part thereof and a major diameter part provided at an other-end part thereof, the major diameter part having an external diameter greater than that of the minor diameter part, including:

an orienting mechanism that orients the accommodating member;

a first inserting mechanism that inserts the pushing member into the accommodating member oriented by the orienting mechanism; and a second inserting mechanism that inserts the absorbent body into the accommodating member in which the pushing member is inserted, the orienting mechanism including:

an opening through which the accommodating member is inputted;

a pair of first protruded parts located on one-end side in a longitudinal direction of the opening and protruding inwardly in an opposing manner into the opening; and a pair of second protruded parts located on other-end side in the longitudinal direction of the opening and protruding inwardly in an opposing manner into the opening, a gap between the pair of first protruded parts being greater than the external diameter of the minor diameter part and smaller than the external diameter of the major diameter part, and a gap between the pair of second protruded parts being greater than the external diameter of the minor diameter part and smaller than the external diameter of the major diameter part.

(Part Two)

In order to achieve the objects described above, the main aspect of the present invention is:

a method of manufacturing a tampon including a tampon main body, an accommodating cylinder accommodating the tampon main body, the accommodating cylinder having an opening formed at a leading end and a plurality of petaloid parts surrounding the opening, and a pushing member that is movable in the accommodating member and pushes the tampon main body out of the accommodating cylinder through the opening, including:

performing a broadening process on the accommodating cylinder, the broadening process broadens the opening by outwardly bending each of the plurality of petaloid parts in the radial direction of the accommodating cylinder;

after performing the broadening process, inserting the pushing member into the accommodating cylinder through the opening; and after performing the broadening process, inserting the tampon main body into the accommodating cylinder through the opening.

(Part Three)

In order to achieve the objects described above, the main aspect of the present invention is:

an apparatus for manufacturing a tampon including a tampon main body, an accommodating cylinder that accommodates the tampon main body, and a pushing member that moves in the accommodating cylinder and pushes the tampon main body out of the accommodating cylinder, a plurality of petaloid parts being provided at a one-end part in the longitudinal direction of the accommodating cylinder, comprising:

a supplying mechanism that supplies the accommodating cylinder; and an inserting mechanism that inserts the tampon main body and the pushing member into the accommodating cylinder supplied by the supplying mechanism, the supplying mechanism including:

a first transport path that transports the accommodating cylinder in a first transport direction lying along the longitudinal direction of the accommodating cylinder; and a second transport path that transports the accommodating cylinder in a second transport direction intersecting the longitudinal direction of the accommodating cylinder, the second transport path including:

a receiving part that receives from the first transport path the accommodating cylinder that has traveled on the first transport path;

a side wall formed on an end part opposite to a side where the accommodating cylinder is passed to the receiving part from the first transport path in the first transport direction; and an outlet formed in the side wall and through which the accommodating cylinder is discharged from the second transport path, the side wall retains in the receiving part the accommodating cylinder which the receiving part has received when there is no accommodating cylinder in the receiving part, and the accommodating cylinder which the receiving part has received when there is an accommodating cylinder in the receiving part is discharged from the second transport path through the outlet.

Other features of the present invention will become apparent from descriptions of this specification and of accompanying drawings.

Effect of the Invention (Part One)

According to an aspect of the invention, the accommodating member can be supplied accurately and rapidly while manufacturing a tampon.

(Part Two)

According to an aspect of the invention, the tampon main body and the pushing member can be smoothly inserted into the accommodating cylinder.

(Part Three)

According to an aspect of the invention, the accommodating cylinders can be supplied properly.

BRIEF DESCRIPTION OF DRAWINGS

FIGS. 3A to 3D are diagrams in a series showing the assembling step of a tampon 1001.

FIGS. 25A to 25D are explanatory diagrams of a broadening process.

Figure 1A:
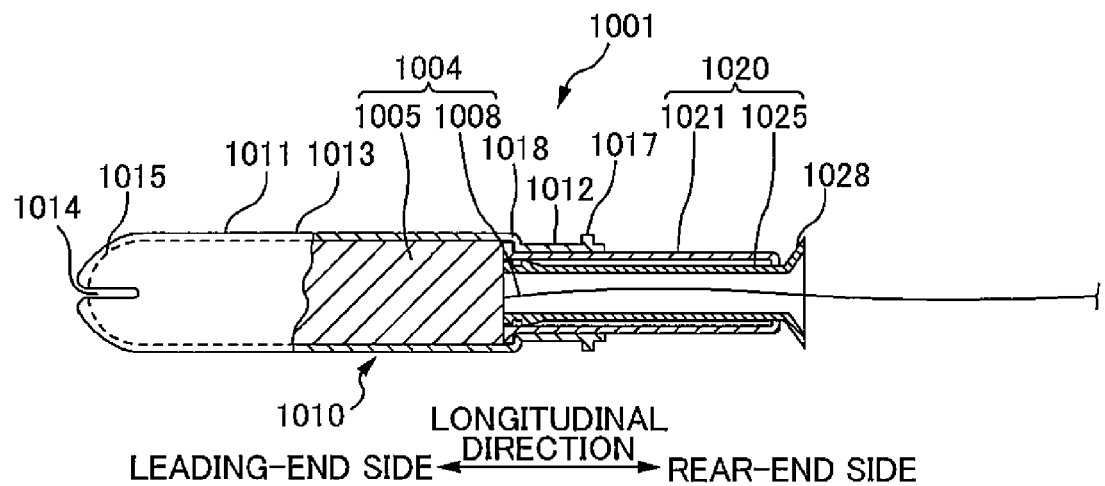
FIG. 1A is a partial cross-sectional view of a tampon 1001 with an inner cylinder 1020 being contracted.

At least the following matters will be disclosed in the present specification and accompanying drawings.

(Part One)

An apparatus for manufacturing a tampon, the tampon including an absorbent body that absorbs liquid, an accommodating member that is cylindrical and accommodates the absorbent body, and a pushing member that moves inside the accommodating member and pushes the absorbent body out of the accommodating member, the accommodating member including a minor diameter part provided at a one-end part thereof and a major diameter part provided at an other-end part thereof, the major diameter part having an external diameter greater than that of the minor diameter part, is provided, which includes:

an orienting mechanism that orients the accommodating member;

a first inserting mechanism that inserts the pushing member into the accommodating member oriented by the orienting mechanism; and a second inserting mechanism that inserts the absorbent body into the accommodating member in which the pushing member is inserted, the orienting mechanism including:

an opening through which the accommodating member is inputted;

a pair of first protruded parts located on one-end side in a longitudinal direction of the opening and protruding inwardly in an opposing manner into the opening; and a pair of second protruded parts located on other-end side in the longitudinal direction of the opening and protruding inwardly in an opposing manner into the opening, a gap between the pair of first protruded parts being greater than the external diameter of the minor diameter part and smaller than the external diameter of the major diameter part, and a gap between the pair of second protruded parts being greater than the external diameter of the minor diameter part and smaller than the external diameter of the major diameter part.

With such an apparatus for manufacturing a tampon, since the above-mentioned relationship is established between the major diameter part, the minor diameter part, the gap between the first protruded parts and the gap between the second protruded parts, it becomes easier for the minor diameter part to pass through the opening before the major diameter part. As a result, the accommodating member is automatically oriented and thus the accommodating member can be supplied properly and rapidly.

In the above apparatus for manufacturing a tampon, it is preferable that, with respect to the accommodating member inputted into the opening in such a manner that a longitudinal direction of the accommodating member lies along the longitudinal direction of the opening, one of the pair of first protruded parts and the pair of second protruded parts is provided at a position at which the minor diameter part passes between the pair of protruded parts; and the other of the pair of first protruded parts and the pair of second protruded parts is provided at a position at which the major diameter part cannot pass between the pair of protruded parts.

With such an apparatus, since it can effectively prevent the major diameter part from passing through the opening before the minor diameter part, it is facilitated to orient the accommodating member properly.

In the above apparatus for manufacturing a tampon, it is preferable that, with respect to the accommodating member inputted into the opening in such a manner that the longitudinal direction of the accommodating member lies along the longitudinal direction of the opening, the other of the pair of first protruded parts and the pair of second protruded parts is provided at a position where it comes into contact with a part of the accommodating member that is nearer to the center than the petaloid parts in the longitudinal direction.

With such an apparatus, the petaloid parts do not come into contact with the protruded parts. Therefore, for example, the petaloid parts can be prevented from being deformed and passing between the protruded parts (that is to say, the major diameter part can be prevented from passing between the protruded parts).

In the above apparatus for manufacturing a tampon, it is preferable that, with respect to the accommodating member inputted into the opening in such a manner that the longitudinal direction of the accommodating member lies along the longitudinal direction of the opening, the other of the pair of first protruded parts and the pair of second protruded parts is provided at a position where it comes into contact with a part of the accommodating member that is nearer to the petaloid parts than the center of the accommodating member in the longitudinal direction.

With such an apparatus, the part of the accommodating member that comes into contact with the other protruded parts when the accommodating member is inputted in the opening is at leading-end side of the major diameter part. (The accommodating member passes through the opening by rotating around this part). Therefore, thereafter, it becomes easier for the accommodating member to pass through the opening from the leading-end side of the minor diameter part that is on the opposite side. As a result, it becomes easier for the minor diameter part to surely pass through the opening before the major diameter part.

In the above apparatus for manufacturing a tampon, it is preferable that, the accommodating member includes an annular protrusion provided nearer to the end than the minor diameter part;

an external diameter of the annular protrusion being greater than the gap between the pair of first protruded parts and being greater than the gap between the pair of second protruded parts; and with respect to the accommodating member inputted into the opening in such a manner that the longitudinal direction of the accommodating member lies along the longitudinal direction of the opening, the one of the pair of first protruded parts and the pair of second protruded parts being provided at a position where it does not come into contact with the annular protrusion.

With such an apparatus, even though an annular protrusion is provided, by providing the protruded parts at positions where they do not come into contact with the annular protrusion, the annular protrusion will not be an obstruction when the minor diameter part passes between the protruded parts. Therefore, it is likely that the minor diameter part will be discharged prior to the major diameter part.

In the above apparatus for manufacturing a tampon, it is preferable that, the orienting mechanism includes:

a first jet part that is provided at a position opposing the first protruded parts and injects air towards the first protruded parts; and a second jet part that is provided at a position opposing the second protruded parts and injects air towards the second protruded parts.

With such an apparatus, since the time taken for the accommodating member to pass through the opening will be shortened due to the air flow injected by the jet parts, the accommodating member can be supplied more rapidly.

In the above apparatus for manufacturing a tampon, it is preferable that, the apparatus includes:

a transport path that transports the accommodating member and inputs the accommodating member into the opening; and the transport path inputs the accommodating member into the opening in such a manner that the attitude of the accommodating member, after being inputted, will be such that the major diameter part comes into contact with one of the pair of first protruded parts and the pair of second protruded parts.

With such an apparatus, since the accommodating member comes into contact with the protruded parts when inputted into the opening, even if the major diameter part is inputted into the opening prior to the major diameter part, the minor diameter part will be discharged prior to the major diameter part. Therefore, the accommodating member can be surely oriented.

In the above apparatus for manufacturing a tampon, it is preferable that, the opening is formed in a rectangular shape; and a distance in the longitudinal direction between an edge on the one-end side in the longitudinal direction of the opening and the first protruded parts is equal to a distance in the longitudinal direction between an edge on the other-end side in the longitudinal direction of the opening and the second protruded parts.

As for the mode of inputting the accommodating member into the opening, there may be a case in which the major diameter part comes into contact with the first protruded parts and a case in which the major diameter part comes into contact with the second protrude parts. According to the apparatus described above, by providing the first protruded parts and the second protruded parts at an equal distance from the edge of the opening in the longitudinal direction, the accommodating member can be properly oriented in both cases.

Further, a method of manufacturing a tampon, the tampon including an absorbent body that absorbs liquid, an accommodating member that is cylindrical and accommodates the absorbent body, and a pushing member that moves inside the accommodating member and pushes the absorbent body out of the accommodating member, the accommodating member including a minor diameter part provided at a one-end part thereof and a major diameter part provided at an other-end part thereof, the major diameter part having an external diameter greater than that of the minor diameter part, is provided, which includes:

orienting, by an orienting mechanism, an orientation of the accommodating member; and inserting, by an inserting mechanism, the absorbent body and the pushing member into the accommodating member that is oriented by the orienting mechanism, the orienting mechanism including:

an opening through which the accommodating member is inputted;

a pair of first protruded parts protruding inwardly into the opening; and a pair of second protruded parts protruding inwardly into the opening;

a gap between the pair of first protruded parts being greater than the external diameter of the minor diameter part and smaller than the external diameter of the major diameter part, a gap between the pair of second protruded parts being greater than the external diameter of the minor diameter part and smaller than the external diameter of the major diameter part, the orienting mechanism allowing the minor diameter part of the inputted accommodating member to pass through one of the pair of first protruded parts and the pair of second protruded parts, and not allowing the major diameter part of the inputted accommodating member to pass through the other of the pair of first protruded parts and the pair of second protruded parts, thereby discharging the minor diameter part of the accommodating member before the major diameter part of the accommodating member.

With such a method of manufacturing a tampon, since the minor diameter part is discharged from the opening prior to the major diameter part, the accommodating member is automatically oriented and thus the accommodating member can be supplied properly and rapidly.

—Structure of Tampon with Applicator—

Figure 1B:
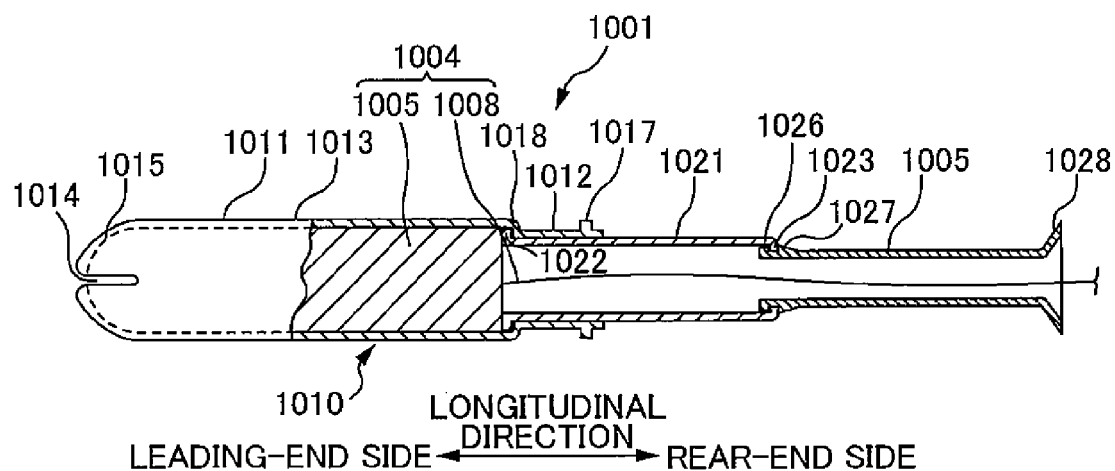
FIG. 1B is a partial cross-sectional view of a tampon 1001 with an inner cylinder 1020 being extended.

Structure of a tampon with an applicator (hereinafter referred to as a tampon 1001) will be described with reference to FIGS. 1A and 1B. FIG. 1A is a partial cross-sectional diagram of the tampon 1001 with an inner cylinder 1020 being contracted. FIG. 1B is a partial cross-sectional diagram of the tampon 1001 with an inner cylinder 1020 being extended. Regarding the longitudinal direction of the tampon 1001 shown in the drawings such as FIG. 1A, a side that is inserted into a vaginal cavity shall be referred to as a leading-end side and the opposite side shall be referred to as a rear-end side.

The tampon 1001 is a sanitary product including a tampon main body 1004 and an applicator 1010.

The tampon main body 1004 includes an absorbent body 1005 and a cord 1008. The absorbent body 1005 is a cotton body that blocks the vaginal cavity and absorbs liquid such as menstrual blood. The absorbent body 1005 is formed by cutting a cotton strip covered with non-woven fabric on both sides and heat forming into a substantially bullet like shape. The cord 1008 is sewn onto the absorbent body 1005 and extends from the rear-end side of the absorbent body 1005. The cord 1008 is then held by a user when the absorbent body 1005 inside the vaginal cavity is pulled out of the vaginal cavity.

The applicator 1010 is an aid device for guiding the tampon main body 1004 (specifically, the absorbent body 1005) into the vaginal cavity. The applicator 1010 includes an outer cylinder 1011 which is an example of an accommodating member that is cylindrical and accommodates the absorbent body 1005 and an inner cylinder 1020 which is an example of a pushing member that moves inside the outer cylinder 1011 and pushes the absorbent body 1005 out of the outer cylinder 1011.

The outer cylinder 1011 is a cylindrical body formed by injection molding a thermoplastic resin and is flexible. The outer cylinder 1011 includes a minor diameter part 1012 provided at the rear-end part (one-end) and a major diameter part 1013 having an external diameter that is greater than that of a minor diameter part 1012 provided on the leading-end part (the other end). The minor diameter part 1012 is a grip part held by a user when using the tampon 1001. The major diameter part 1013 is a part which has an internal diameter that is greater than the external diameter of the absorbent body 1005 and which accommodates the absorbent body 1005 therein. When using the tampon 1001, the major diameter part 1013 is inserted into the vaginal cavity with the absorbent body 1005 being accommodated therein.

The outer cylinder 1011 (specifically, the major diameter part 1013) includes a leading-end opening 1014 formed at its leading end and a plurality of petaloid parts 1015 surrounding the leading edge opening 1014. When shipping the tampon 1001, each of the plurality of petaloid parts 1015 is inwardly bent in an arc in the radial direction of the outer cylinder 1011. Therefore, when the outer cylinder 1011 is inserted into the vaginal cavity, the leading-end part of the major diameter part 1013 is substantially hemispherical and the leading-end opening 1014 is substantially in a closed position.

Further, the outer cylinder 1011 includes a rear-end opening 1016 formed at its rear end (see FIG. 3A) and an annular protrusion (annular rib) 1017 provided at a position slightly towards the leading-end side than the rear-end opening 1016 (provided at a position nearer to the rear-end side than the minor diameter part 1012). Further, an annular stepped part 1018 is formed between the minor diameter part 1012 and the major diameter part 1013.

The inner cylinder 1020 is a cylindrical body inserted in the minor diameter part 1012. The inner cylinder 1020 is provided at a position nearer to the rear-end side than the absorbent body 1005 accommodated in the major diameter part 1013 and pushes the absorbent body 1005 from the rear towards the leading-end opening 1014. Thereby, the absorbent body 1005 (tampon main body 1004) pushes out each of the plurality of petaloid parts 1015 outwardly in the radial direction of the outer cylinder 1011 and is pushed out of the major diameter part 1013. The cord 1008 extends through the inner cylinder 1020 and is pulled out from the opening at the rear-end side of the inner cylinder 1020. It is to be noted that the inner cylinder 1020 of the present embodiment is formed as an extendable two-tier structure. In detail, the inner cylinder 1020 includes a first inner cylinder 1021 and a second inner cylinder 1025 that is slidably inserted in the first inner cylinder.

The first inner cylinder 1021 has an external diameter that is smaller than the internal diameter of the minor diameter part 1012 and is inserted in the minor diameter part 1012. An annular flange part 1022 is formed on an outer peripheral surface of the leading-end part of the first inner cylinder 1021. The flange part 1022 has an external diameter that is smaller than the internal diameter of the major diameter part 1013 (greater than the internal diameter of the minor diameter part 1012) and engages an inner surface of the stepped part 1018 of the outer cylinder 1011, thereby preventing the inner cylinder 1020 from falling off from the rear-end opening 1016 of the outer cylinder 1011. Further, at the rear-end side on an inner peripheral surface of the first inner cylinder 1021, an annular protrusion 1023 extending inwardly in the radial direction is provided.

The second inner cylinder 1025 has an external diameter that is smaller than the internal diameter of the first inner cylinder 1021. The second inner cylinder 1025 is, when the inner cylinder 1020 is in a contracted state, inserted in the first inner cylinder 1021 as shown in FIG. 1A and, when the inner cylinder 1020 is in an extended state, connected to the rear-end part of the first inner cylinder 1021 at the leading-end part of the second inner cylinder 1025 as shown in FIG. 1B. Further, on the outer peripheral surface of the leading-end part of the second inner cylinder 1025, an arcuate flange part 1026 and a protruded part 1027 provided at a position nearer to the rear-end side than the flange part 1026 is formed. When the annular protrusion 1023 of the first inner cylinder 1021 is at a position between the flange part 1026 and the protruded part 1027 as shown in FIG. 1B, the protrusion 1023 engages the flange part 1026 and the protruded part 1027, and thus the first inner cylinder 1021 and the second inner cylinder 1025 are connected. Further, a flared part 1028 is formed at the rear-end part of the second inner cylinder 1025. The external diameter of the flared part 1028 is greater than the internal diameter of the first inner cylinder 1021.

—Method of Manufacturing a Tampon 1001—

Figure 2A:
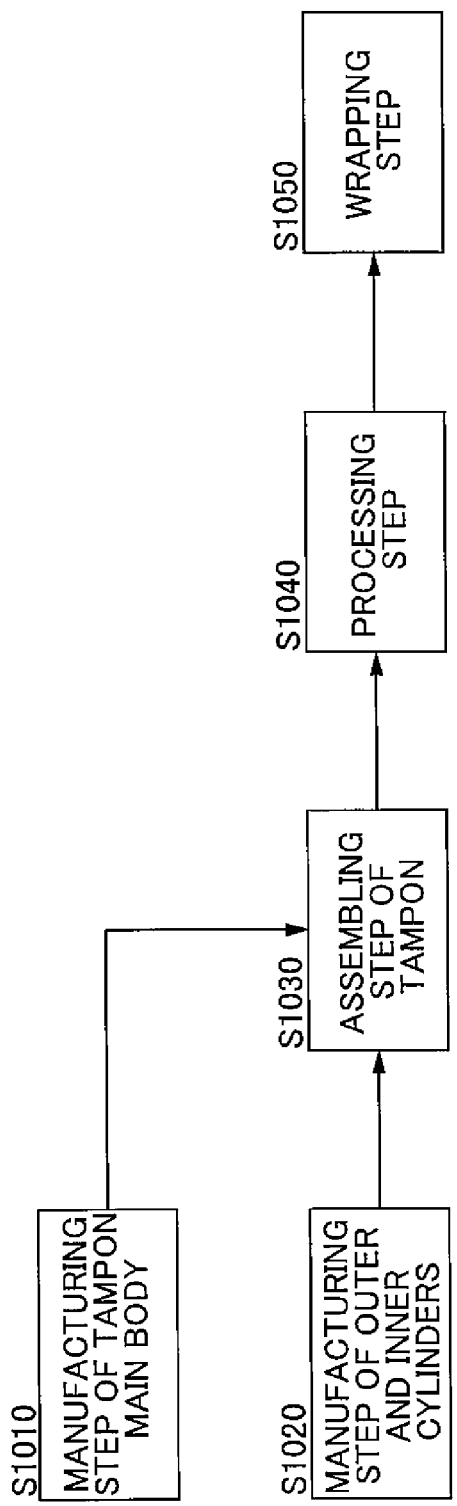
FIG. 2A is a flowchart showing the manufacturing of a tampon 1001.
Figure 2B:
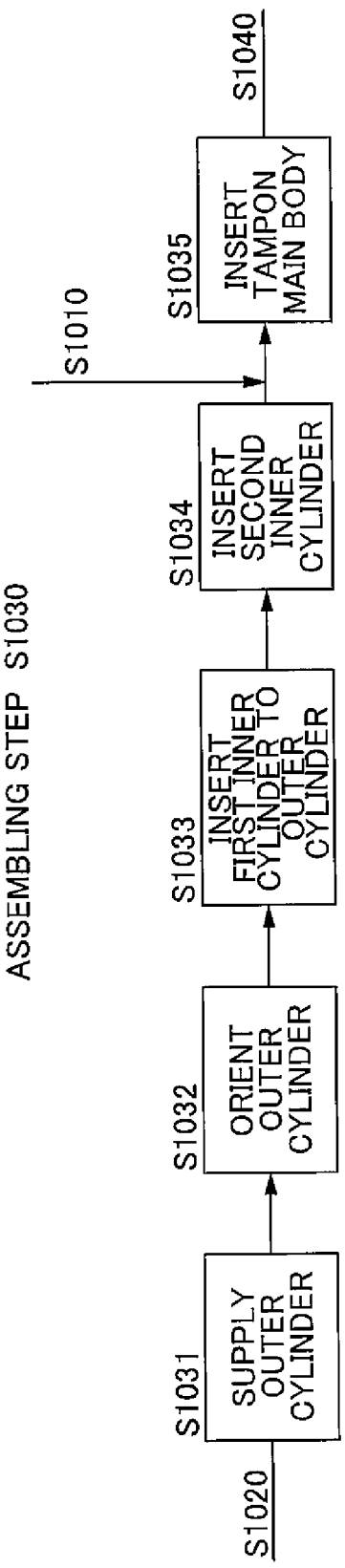
FIG. 2B is a diagram showing the details of an assembling step.

FIG. 2A is a flowchart showing how the tampon 1001 is manufactured. FIG. 2B is a diagram showing details of the assembling step. FIGS. 3A to 3D are diagrams showing the assembling step of the tampon 1001 in a series. In the following description, the method of manufacturing the tampon 1001 will be described step by step (steps S1010, S1020, S1030, S1040 and S1050).

<<Manufacturing Step of Tampon Main Body 1004: STEP S1010>>

First, a cotton strip is covered with non-woven fiber on both surfaces and then the cotton strip is cut. Secondly, a cord is sewn on the cut cotton strip using a sewing thread. Then, the cotton strip on which the cord is sewn is pressed into a substantially bullet-shaped cotton body and then heat formed. In this manner, the tampon main body 1004 having the absorbent body 1005 and the cord 1008 is manufactured.

<<Manufacturing Step of Outer Cylinder 1011 and Inner Cylinder 1020: STEP S1020>>

Using an injection molding machine, the outer cylinder 1011 and the inner cylinder 1020 (the first inner cylinder 1021 and the second inner cylinder 1025) are each injection molded. The outer cylinder 1011 is injection molded using a thermoplastic resin, for example. It is to be noted that at the time of manufacture, the outer cylinder 1011 is in a state where each of the plurality of petaloid parts 1015 is open, i.e., a leading-end opening 1014 is in an open state (See FIG. 3A). Also, the flared part 1028 is not formed at the rear-end part of the second inner cylinder 1025 (See FIG. 3B).

<<Assembling Step of Tampon 1001: STEP S1030>>

The manufactured tampon main body 1004, the outer cylinder 1011 and the inner cylinder 1020 (the first inner cylinder 1021 and the second inner cylinder 1025) are assembled by an assembling apparatus 1040 (details will be described later), which is an example of the manufacturing apparatus of the tampon 1001.

An outline of the assembling of the tampon 1001 will be described.

First, in the assembling apparatus 1040, the outer cylinder 1011 is supplied to a transport conveyor (step S1031). The outer cylinder 1011 that is being supplied is oriented (step S1032). Then, as shown in FIG. 3A, the first inner cylinder 1021 is inserted into the oriented outer cylinder 1011 (step S1033). It is to be noted that the first inner cylinder 1021 is inserted into the outer cylinder 1011 through the leading-end opening 1014 thereof. Then, as shown in FIG. 3B, the second inner cylinder 1025 is inserted into the outer cylinder 1011 in which the first inner cylinder 1021 is inserted (step S1034). In this manner, the applicator 1020 is assembled. Then, as shown in FIG. 3C, the tampon main body 1004 is inserted into the outer cylinder 1011 (step 1035). In this step, the cord 1008 is firstly inserted into the outer cylinder 1011. Thereby, the absorbent body 1005 is accommodated in the major diameter part 1013.

It is to be noted that in this assembling step, step S1032 corresponds to the step of orienting the outer cylinder 1011 by the orienting mechanism 1060 (to be described later) and steps S1033 to S1035 correspond to the steps of inserting the absorbent body 1005 and the inner cylinder 1020 into the outer cylinder 1011 which has been oriented by the orienting mechanism 1060 by the tampon main body inserting part 1070 (to be described later).

<Structure of Assembling Apparatus 1040>

Figure 4:
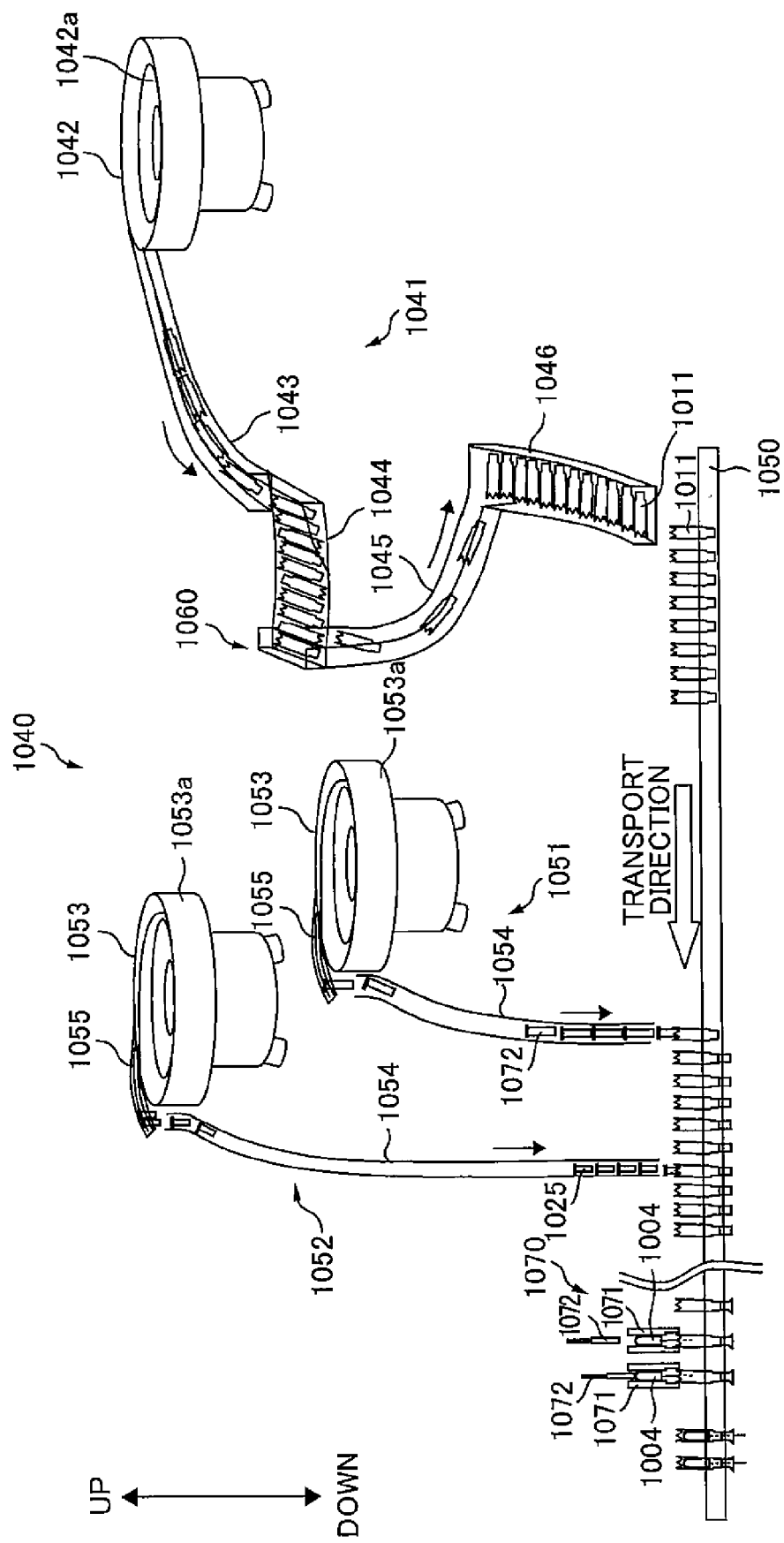
FIG. 4 is a diagram showing an assembling apparatus 1040 of a tampon 1001.

The structure of the assembling apparatus 1040 that assembles the tampon 1001 will now be described. FIG. 4 is a diagram showing the assembling apparatus 1040 of the tampon 1001.

The assembling apparatus 1040 includes an outer cylinder supplying part 1041, a transport conveyor 1050, a first inner cylinder supplying part 1051, a second inner cylinder supplying part 1052 and a tampon main body inserting part 1070.

The transport conveyor 1050 transports the outer cylinder 1011 and each article (the first inner cylinder 1021, the second inner cylinder 1025 and the tampon main body 1004) inserted in the outer cylinder 1011 in a transport direction. A fixing table (not shown) adapted to fix the outer cylinder 1011 is provided on the transport conveyor 1050. As the fixing table is transported by the transport conveyor 1050, the outer cylinder 1011 etc., that is fixed on the fixing table is transported in the transport direction.

The outer cylinder supplying part 1041 supplies the outer cylinder 1011 to the transport conveyor 1050. The outer cylinder supplying part 1041 includes an outer cylinder transport feeder 1042 and a transport path 1043 on which the supplied outer cylinders 1011 are transported.

The outer cylinder transport feeder 1042 is a parts feeder having a bowl-shaped vibratory table 1042a. By vibrating the vibratory table 1042a, the outer cylinder transport feeder 1042 transports the outer cylinder 1011 to the transport path 1043.

At a middle part and an end part of the transport path 1043, accumulating parts 1044 and 1046 are formed that accumulate the outer cylinders 1011 which are being transported primarily in a side-by-side manner. The plurality of outer cylinders 1011 accumulated in the accumulating parts 1044 and 1046 are arranged in a side-by-side manner. Between the accumulating parts 1044 and 1046, there is provided a drop chute 1045 through which the outer cylinders 1011 drop. At the end of the transport path 1043, an outer cylinder setting part (not shown) that sets the outer cylinder 1011 accumulated in the accumulating part 1046 on the fixing table of the transport conveyor 1050 is provided. At the inlet of the drop chute 1045, an orienting mechanism 1060 (details will be described later) that orients the outer cylinder 1011 that is inputted into the drop chute 1045 is provided.

With the outer cylinder supplying part 1041 of such structure, the outer cylinders 1011 transported on the transport path 1043 and accumulated in the accumulating part 1044 drop through the drop chute 1045 sequentially. (During this, the outer cylinders 1011 are oriented). Then, the outer cylinders 1011 that have passed through the drop chute 1045 are accumulated in the accumulating part 1046. Then, the outer cylinders 1011 accumulated in the accumulating part 1046 are set on the fixing table of the transport conveyor 1050 by the outer cylinder setting part.

The first inner cylinder supplying part 1051 supplies the first inner cylinder 1021 to the transport conveyor 1050, which first inner cylinder 1021 is to be inserted into the outer cylinder 1011 transported by the transport conveyor 1050. The first inner cylinder supplying part 1051 includes an inner cylinder transport feeder 1053 and a transport tube 1054.

The inner cylinder transport feeder 1053 is a parts feeder having a bowl-shaped vibratory table 1053a. A pair of rails 1055 forming a part of the transport path of the first inner cylinder 1021 is attached to the inner cylinder transport feeder 1053. Between the pair of rails 1055, a space that can hold the first inner cylinder 1021 between the rails 1055 is formed. The flange part 1022 of the first inner cylinder 1021 held in the space engages the top part of the pair of rails 1055 and the first inner cylinder 1021 is transported while being hung down from the pair of rails 1055.

The first inner cylinder 1021 transported by the pair of rails 1055 drops in the transport tube 1054 with its leading end being located above the rear end. At the end of the transport tube 1054, an inner cylinder inserting mechanism (not shown) that inserts The first inner cylinder 1021 into the outer cylinder 1011 is provided. When the outer cylinder 1011 that is being transported by the transport conveyor 1050 is located below the inner cylinder inserting mechanism, the inner cylinder inserting mechanism presses the first inner cylinder 1021 dropped in the transport tube 1054 and inserts it into the outer cylinder 1011. In other words, the first inner cylinder 1021 is inserted into the outer cylinder 1011 as shown in FIG. 3A. It is to be noted that the transport tube 1054 and the inner cylinder inserting mechanism correspond to the first inserting mechanism.

The second inner cylinder supplying part 1052 supplies the second inner cylinder 1025 to the transport conveyor 1050, which second inner cylinder 1025 is to be inserted into the outer cylinder 1011 that is being transported with the first inner cylinder 1021 inserted therein. Since the structure of the second inner cylinder supplying part 1052 is similar to that of the first inner cylinder supplying part 1051, it will not be described here. As shown in FIG. 3B, the second inner cylinder 1025 is inserted into the outer cylinder 1011 by the second inner cylinder supplying part 1052.

The tampon main body inserting part 1070 (an example of the second inserting mechanism) inserts the absorbent body 1005 (tampon main body 1004) into the outer cylinder 1011 in which the first inner cylinder 1021 and the second inner cylinder 1025 are inserted. The tampon main body inserting part 1070 includes a guide part 1071 that guides the insertion of the tampon main body 1004 into the outer cylinder 1011 and a pin 72 that pushes the tampon main body 1004 out of the guide part 1071. The guide part 1071 further includes a mechanism that holds the tampon main body 1004. The tampon main body 1004 in the guide part 1071 is held in a state that the cord 1008 is situated below the absorbent body 1005.

When the outer cylinder 1011 that is being transported by the transport conveyor 1050 is situated below the guide part 1071, the tampon main body inserting part 1070 pushes the tampon main body 1004 held by the guide part 1071 using the pin 1072. Thereby, as shown in FIG. 3C, the tampon main body 1004 is inserted into the outer cylinder 1011.

By performing the assembling step (step S1030) with the assembling apparatus 1040 of the above-mentioned structure, the first inner cylinder 1021, the second inner cylinder 1025 and the tampon main body 1004 are properly inserted into the outer cylinder 1011.

<<Processing Step: STEP S1040>>

In this processing step, a bending process for arcuately bending the petaloid parts 1015 in the open state of the outer cylinder 1011 inwardly in the radial direction of the outer cylinder 1011 is performed. It is to be noted that the process of forming the flared part 1028 at the rear-end part of the second inner cylinder 1025 is performed in the assembling step (step S1030). With these processes, the tampon 1001 shown in FIG. 3D is formed.

<<Wrapping Step: STEP S1050>>

With the processing of the tampon 1001 is completed, the tampon 1001 is inserted into a wrapper that is formed into a cylindrical shape to wrap the tampon 1001. Thereafter, a plurality of wrapped tampons 1001 are packed in a box. Thus, the manufacturing of the tampons 1001 is completed and they will be shipped later on.

—Detailed Structure of Orienting Mechanism 1060—

Figure 5:
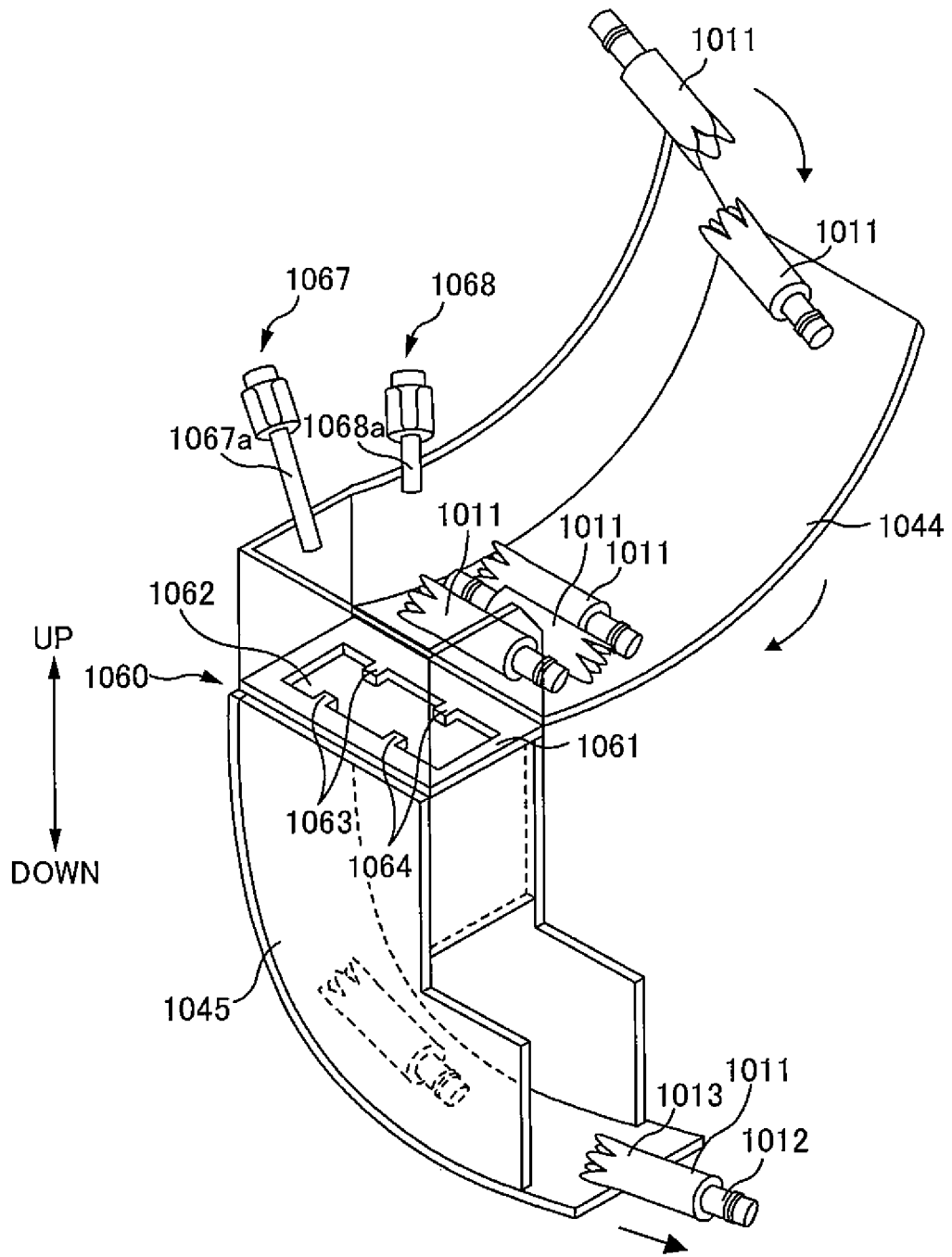
FIG. 5 is a perspective diagram showing an orienting mechanism 1060 and a neighboring part thereof.
Figure 6:
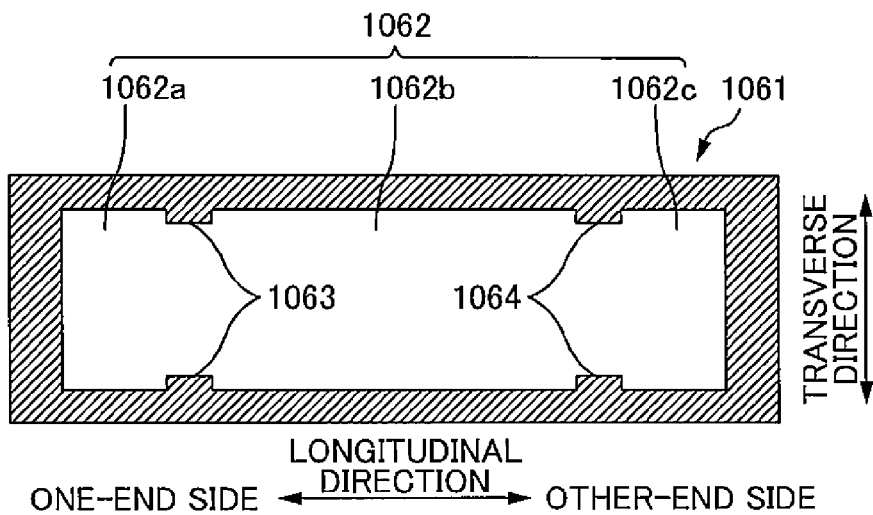
FIG. 6 is a top view showing an orienting plate 1061.
Figure 7A:
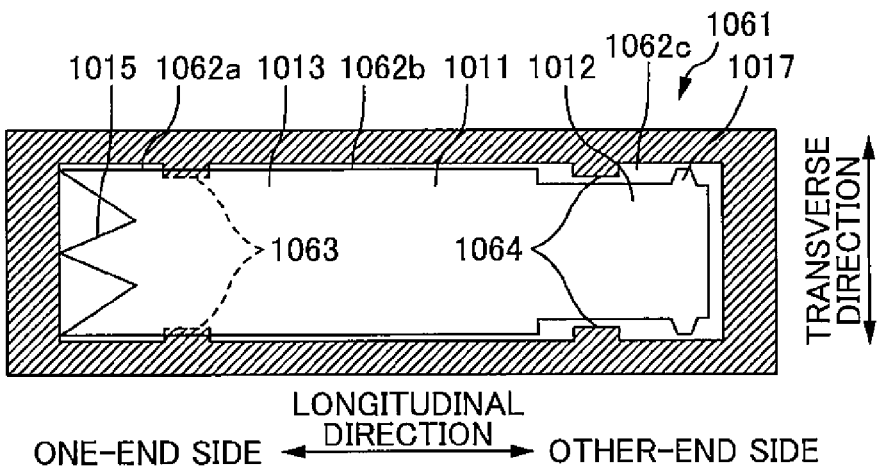
FIGS. 7A and 7B are diagrams showing a positional relationship between an outer cylinder 1011 and an orienting plate 1061 when the outer cylinder 1011 is being inputted into an opening 1062.
Figure 7B:
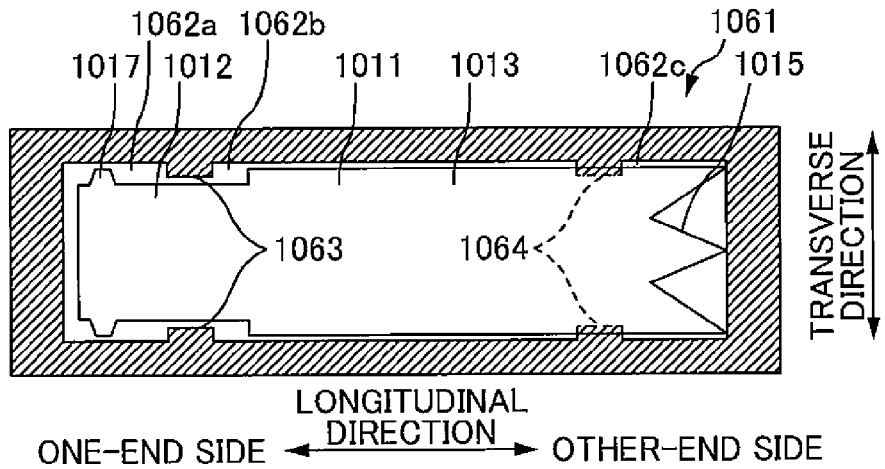

FIG. 5 is a perspective diagram showing an orienting mechanism 1060 and the neighboring part thereof. FIG. 6 is a top view showing an orienting plate 1061. FIGS. 7A and 7B are diagrams showing a positional relationship between the outer cylinder 1011 and an orienting plate 1061 when the outer cylinder 1011 is being dropped into an opening 1062.

As shown in FIG. 5, the orienting mechanism 1060 is provided at the inlet of the drop chute 1045 and includes the orienting plate 1061, a first jet part 1067 and a second jet part 1068. In the following description, after describing the structure of the orienting plate 1061, the structures of a first jet part 1067 and a second jet part 1068 will be described.

<<Structure of the Orienting Plate 1061>>

The orienting plate 1061 is a rectangular flat plate provided at the inlet of the drop chute 1045. The outer cylinders 1011 accumulated side-by-side in the accumulating part 1044 are dropped through the orienting plate 1061 and the outer cylinders 1011 are oriented.

As shown in FIG. 6, the orienting plate 1061 includes an opening 1062 through which the outer cylinder 1011 is inputted and first protruded parts 1063 and second protrude parts 1064 protruding inwardly into the opening 1062.

The opening 1062 is a rectangular opening and is formed in such a manner that its size is slightly greater that the size of the outer cylinder 1011. The outer cylinders 1011 that are transported on the transport path 1043 and accumulated in the accumulating part 1044 are inputted into the opening 1062 sequentially. As shown in FIGS. 7A and 7B, the outer cylinder 1011 is inputted in such a manner that the longitudinal direction of the outer cylinder 1011 lies along the longitudinal direction of the opening 1062. For example, among the outer cylinders 1011 accumulated in the accumulating part 1044 shown in FIG. 5, the outer cylinder 1011 that is at the nearest position to the opening 1062 is inputted as shown in FIG. 7A and the outer cylinder 1011 that is at the second nearest position to the opening 1062 is inputted as shown in FIG. 7B.

The first protruded parts 1063 are provided at one end side in the longitudinal direction of the opening 1062 and are a pair of opposing protruded parts. As shown in FIGS. 7A and 7B, the gap between the pair of the first protruded part 1063 is greater than the external diameter of the minor diameter part 1012 of the outer cylinder 1011 and is smaller than the external diameter of the major diameter part 1013. Further, the external diameter of the annular protrusion 1017 of the outer cylinder 1011 is greater than a gap between a pair of first protruded parts 1063. Therefore, the major diameter part 1013 and the annular protrusion 1017 cannot pass through the pair of first protruded part 1063 and on the other hand the minor diameter part 1012 can pass through the pair of first protruded part 1063.

The second protruded parts 1064 are provided at the other end side in the longitudinal direction of the opening 1062 and are a pair of opposing protruded parts. Similarly to the first protruded part 1063, the gap between a pair of the second protruded parts 1064 is greater than the external diameter of the minor diameter part 1012 of the outer cylinder 1011 and is smaller than the external diameter of the major diameter part 1013. Further, the external diameter of the annular protrusion 1017 of the outer cylinder 1011 is greater than a gap between a pair of first protruded parts 1063. Therefore, the major diameter part 1013 and the annular protrusion 1017 cannot pass through the pair of first protruded parts 1063 and on the other hand the minor diameter part 1012 can pass through the pair of first protruded part 1063.

The opening 1062 is divided into three portions by the first protruded parts 1063 and the second protruded parts 1064. (In other words, it is divided into a one-end opening 1062a, a central opening 1062b and other-end opening 1062c.) The one-end opening 1062a is at a location nearer to the one-end side in the longitudinal direction of the opening than the first protruded parts 1063, the central opening 1062b is at a location between the first protruded parts 1063 and the second protruded parts 1064 in the longitudinal direction, and the other end opening 1062c is at a position nearer to the other end side than the second protruded part 1064 in the longitudinal direction. The width in the longitudinal direction of the one end opening 1062a and the width in longitudinal direction of the other end opening 1062c are smaller than the external diameter of the minor diameter part 1012. On the other hand, the width in longitudinal direction of the central opening 1062b is greater than the external diameter of the major diameter part 1013. The width in longitudinal direction of the one end opening 1062a (in other words, the distance between the edge on the one end side of the longitudinal direction of the first end opening 1062a and the first protruded parts 1063) is the same as the width in the longitudinal direction of the other end opening 1062c (in other words, the distant between an edge on The opening 1062 other end part in the longitudinal direction and the second protruded parts 1064).

The positional relationship between the outer cylinder 1011 inputted into the opening 1062 and the first and second protruded parts 1063, 1064 will now be described.

First, a case in which the outer cylinder 1011 is inputted as shown in FIG. 7A will be described. With regards to the outer cylinder 1011 inputted into the opening 1062, among the first protruded parts 1063 and the second protruded parts 1064, the second protruded parts 1064 are provided at positions where they do not come into contact with the annular protrusion 1017 (specifically, at positions nearer to the center than the annular protrusion 1017 in the longitudinal direction of the opening 1062.) On the other hand, the first protruded parts 1063 are provided at positions where they come into contact with a part of the outer cylinder 1011 which is nearer to the center than the petaloid parts 1015 in the longitudinal direction (specifically, at a part of the outer cylinder 1011 nearer to the petaloid parts 1015 than the center). Accordingly, the second protruded parts 1064 are provided at positions where the minor diameter part 1012 passes between the pair of second protruded parts 1064 and the first protruded parts 1063 are provided at positions where the major diameter part 1013 cannot pass between the pair of first protruded parts 1063.

Secondly, a case in which the outer cylinder 1011 is inputted as shown in FIG. 7B is described. With regards to the outer cylinder 1011 inputted into the opening 1062, among the first protruded parts 1063 and the second protruded parts 1064, the first protruded parts 1063 are provided at positions where they do not come into contact with the annular protrusion 1017 (specifically, at positions nearer to the center than the annular protrusion 1017 in the longitudinal direction of the opening 1062.) On the other hand, the second protruded parts 1064 are provided at positions where they come into contact with a part of the outer cylinder 1011 which is nearer to the center than the petaloid parts 1015 in the longitudinal direction (specifically, at a part of the outer cylinder 1011 nearer to the petaloid parts 1015 than the center). Accordingly, the first protruded parts 1063 are provided at positions where the minor diameter part 1012 passes between the pair of first protruded parts 1063 and the second protruded parts 1064 are provided at positions where the major diameter part 1013 cannot pass between the pair of second protruded parts 1064.

By providing the orienting plate 1061 of such a structure, the orientation of the outer cylinder 1011 inputted into the opening 1062 is properly and quickly oriented based on the mechanism of orienting the outer cylinder 1011 to be described later.

<<Structure of First Jet Part 1067 and Second Jet Part 1068>>

As shown in FIG. 5, a first jet part 1067 is provided at a position above the orienting plate 1061 and opposing the first protruded parts 1063. Further, the first jet part 1067 includes a nozzle 1067a that injects air and injects air towards the first protruded parts 1063. In other words, the first jet part 1067 injects air towards the outer cylinder 1011 inputted into the opening 1062 (in the case of FIG. 7A, towards the major diameter part 1013).

The second jet part 1068 is provided at a position above the orienting plate 1061 and opposing the second protruded parts 1064. Further, the second jet part 1068 includes a nozzle 1068a that injects air and injects the air towards the second protruded parts 1064. In other words, the second jet part 1068 injects the air towards the outer cylinder 1011 inputted into the opening 1062 (in the case of FIG. 7A, towards the minor diameter part 1012).

Because the first jet part 1067 and the second jet part 1068 inject air towards the outer cylinder 1011 inputted into the opening 1062, the time taken for the outer cylinder 1011 to pass through the opening 1062 (drop chute 1045) can be shortened and the supply speed of the outer cylinder 1011 can be increased. It is to be noted that during the supply of outer cylinder 1011, the first jet part 1067 and the second jet part 1068 inject air continuously. Of course, air can be intermittently injected in accordance with the dropping timing of the outer cylinder 1011 into the opening 1062.

—Mechanism of Orienting the Outer Cylinder 1011 Using the Orienting Mechanism 1060—

As has been described above, the outer cylinder 1011 is inputted into the opening 1062 with one of the two modes shown in FIGS. 7A and 7B. Since the mechanism for orienting the outer cylinder 1011 inputted as shown in FIG. 7A and the mechanism for orienting the outer cylinder 1011 inputted as shown in FIG. 7B are similar, the following description will be made with reference to the mechanism of orienting the outer cylinder 1011 that is inputted as shown in FIG. 7A.

FIGS. 8A to 8D are diagrams illustrating the mechanism of orienting the outer cylinder 1011.

Figure 8A:
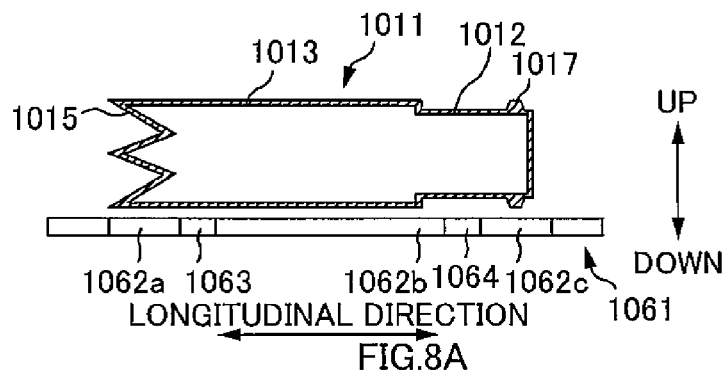
FIGS. 8A to 8D are diagrams illustrating the mechanism of orienting an outer cylinder 1011.

FIG. 8A shows how the outer cylinder 1011 accumulated side-by-side in the accumulating part 1044 is inputted into the opening 1062 in the orienting plate 1061 in a state shortly before the outer cylinder 1011 is inputted into the opening 1062. The outer cylinder 1011 is inputted into the opening 1062 with an attitude such that the major diameter part 1013 comes into contact with the pair of first protruded parts 1063 after being inputted. In detail, the outer cylinder 1011 is inputted in such a manner that the outer cylinder 1011 and the opening 1062 are in parallel. Therefore, since the minor diameter part 1012 and the major diameter part 1013 of the outer cylinder 1011 are inputted into the opening 1062 substantially at the same time, the subsequent orienting can be performed properly.

Figure 8B:
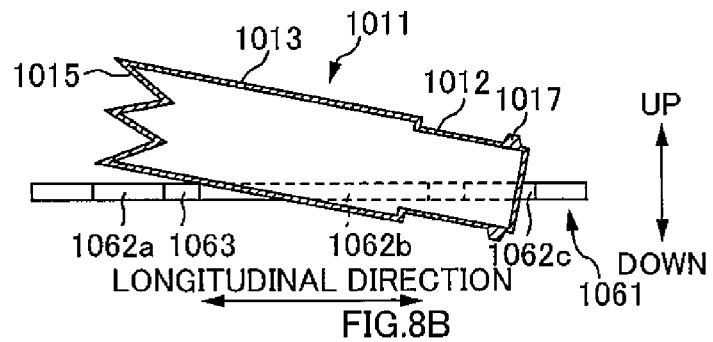

The major diameter part 1013 of the outer cylinder 1011 that is inputted comes into contact with the first protruded parts 1063 as shown in FIG. 8B, since the external diameter of the major diameter part 1013 is greater than the gap between the pair of first protruded parts 1063. In other words, the major diameter part 1013 does not pass between the first protruded parts 1063. It is to be noted that because the first protruded parts 1063 come into contact with a part of the major diameter part 1013 nearer to the center than the petaloid parts 1015 in the longitudinal direction, the petaloid parts 1015 can be prevented from being deformed by coming into contact with the first protruded parts 1063 and passing between the first protruded parts 1063.

On the other hand, since the external diameter of the minor diameter part 1012 is smaller than the gap between the pair of second protruded parts 1064, the minor diameter part 1012 of the outer cylinder 1011 starts passing between the pair of second protruded parts 1064 as shown in FIG. 8B. It is to be noted that because the first protruded parts 1063 come into contact with a part of the outer cylinder 1011 nearer to the petaloid parts 1015 than the center, it is likely to drop from the leading-end side of the minor diameter part 1012 on the opposite side. As a result, it is easier for the minor diameter part 1012 to pass between the second protruded parts 1064.

Also, when the minor diameter part 1012 passes between the second protruded parts 1064, the annular protrusion 1017 of the outer cylinder 1011 starts passing the other-end opening 1062c. That is to say, the annular protrusion 1017 does not obstruct the passage of the minor diameter part 1012 through the opening 1062 because the annular protrusion 1017 is at a position that does not come into contact with the second protruded parts 1064. Further, since the second jet part 1068 opposing the second protruded parts 1064 injects air towards the minor diameter part 1012, the speed at which the minor diameter part 1012 passes between the pair of second protruded parts 1064 increases.

Figure 8C:
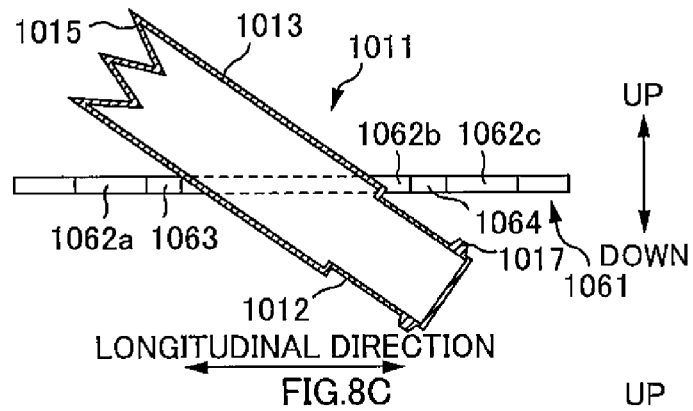

Also after the minor diameter part 1012 has started passing between the second protruded parts 1064, while major diameter part 1013 remains in contact with the first protruded parts 1063 (i.e., a state in which the major diameter part 1013 does not pass between the pair of first protruded parts 1063), the minor diameter part 1012 drops between the pair of second protruded parts 1064 (the minor diameter part 1012 rotates about a part at which the major diameter part 1013 is in contact with the first protruded parts 1063). Thus, the minor diameter part 1012 completely passes between the pair of second protruded parts 1064 as shown in FIG. 8C. At this point, the major diameter part 1013 starts passing through the central opening 1062b.

Figure 8D:
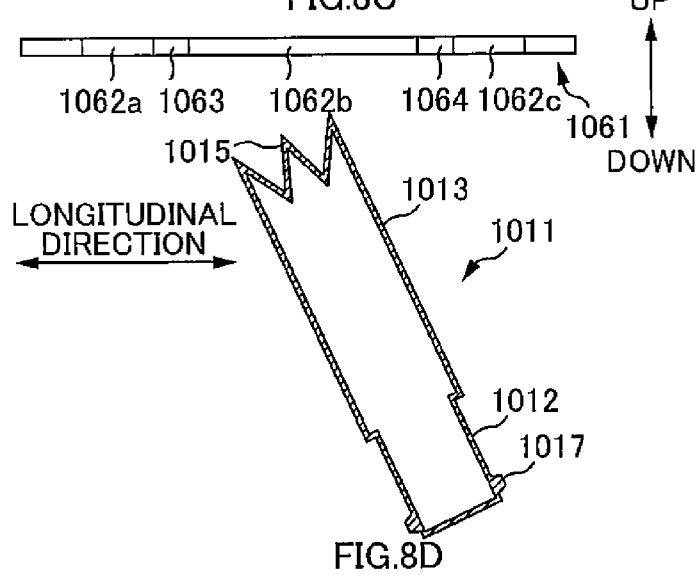

In this manner, the major diameter part 1013 completely passes through the central opening 1062c and the outer cylinder 1011 is discharged from the orienting plate 1061 as shown in FIG. 8D. The plurality of outer cylinders 1011 accumulated side-by-side in the accumulating part 1044 are sequentially inputted into the opening 1062 and each of the outer cylinders 1011 discharged from the opening 1062 is oriented in a manner described below. That is to say, as shown in FIG. 8D, the outer cylinder 1011 is oriented in such a manner that its major diameter part 1013 is at an upper position and the minor diameter part 1012 is at a lower position.

(In other words, it is oriented in such a manner that the minor diameter part 1012 drops first).

It is to be noted that also for the outer cylinder 1011 that is dropped in a manner shown in FIG. 7B, the outer cylinder 1011 is oriented by a similar mechanism. That is to say, the outer cylinder 1011 is oriented in such a manner that the minor diameter part 1012 drops first.

In this manner, the orienting mechanism 1060 discharges the minor diameter part 1012 of the outer cylinder 1011 prior to the major diameter part 1013 by allowing the minor diameter part 1012 of the outer cylinder 1011 that has been inputted to pass between one of the pair of first protruded parts 1063 and the pair of the second protruded parts 1064 while not allowing the major diameter part 1013 of the outer cylinder 1011 that has been inputted to pass between the other of the pair of first protruded parts 1063 and the pair of the second protruded parts 1064.

<<Effectiveness of Assembling Apparatus 1040 and Manufacturing Method of the Present Embodiment>>

As has been described above and as shown in FIG. 5, the orienting mechanism 1060 includes the opening 1062 through which the outer cylinder 1011 is inputted, the pair of first protruded parts 1063 and the pair of second protruded parts 1064 protruding inwardly into the opening 1062. The gap between the pair of first protruded parts 1063 and the gap between the pair of second protruded parts 1064 are each greater than the external diameter of the minor diameter part 1012 of the outer cylinder 1011 and smaller than the external diameter of the major diameter part 1013. Thus, the outer cylinder 1011 can be supplied properly and rapidly when manufacturing the tampon 1001.

In the following description, the effectiveness of the present embodiment will be described with reference to two comparison examples.

Firstly, in comparison example 1, the orientation of the outer cylinder 1011 that is being transported in the transport path is determined based on video signals obtained by imaging the outer cylinder 1011 using camera etc., having an image sensor. Then, the outer cylinder 1011 is oriented by using a turning device to change the orientation in such a manner that the outer cylinder 1011 is oriented in a predetermined orientation. However, in the case of comparison example 1, a complicated structure is required and it is likely that a longer time will be needed to orient the outer cylinder 1011.

In comparison example 2, the outer cylinder 1011 is sent to a device which fits with the major diameter part 1013 but does not fit with the minor diameter part 1012. Then, the outer cylinder 1011 is oriented by discharging only the outer cylinder 1011 that was sent in the orientation which does not fit. However, in the case of comparison example 2, since the major diameter part 1013 includes the petaloid parts 1015, it is difficult to fit the major diameter part 1013 in a proper manner. As a result, there is a possibility that the outer cylinder 1011 is falsely discharged. Also, since the outer cylinder 1011 is discharged, the supply efficiency of the outer cylinder 1011 is decreased.

On the other hand, in the present embodiment, since the above-mentioned relationship holds between the external diameter of the minor diameter part 1012, the external diameter of the major diameter part 1013, the gap between the first protruded parts 1063 and the gap between the second protruded parts 1064, it is easier for the minor diameter part 1012 to firstly pass through the gaps between one of the first protruded parts 1063 and the second protruded parts 1064. Specifically, as shown in FIGS. 8A to 8D, for example, the orienting mechanism 1060 allows the minor diameter part 1012 of the outer cylinder 1011 that has been inputted to pass between the pair of second protruded parts 1064 and does not allow the major diameter part 1013 to pass between the pair of first protruded parts 1063. Accordingly, the minor diameter part 1012 of the outer cylinder 1011 is discharged prior to the major diameter part 1013. Thus, the outer cylinder 1011 that drops in the drop chute 45 simply passes through the orienting plate 1061 and then the outer cylinder 1011 is oriented automatically. As a result, the outer cylinder 1011 can be supplied rapidly as compared to comparison example 1. Also, the structure can be simplified as compared to comparison example 1. Further, since the orientation of all outer cylinders 1011 that drops into the drop chute 1045 can be oriented, the supply efficiency can be raised as compared to comparison example 2.

Based on the above, according to the assembling apparatus 1040 and manufacturing method of the tampon 1001 of the present embodiment, upon manufacturing the tampon 1001, the outer cylinder 1011 can be supplied to the transport conveyor 1050 properly and rapidly.

—Second Embodiment—

A second embodiment that has a different structure from the above-described embodiment (first embodiment) will now be described. In the following description, the structure of a tampon 1001 of the second embodiment and the manufacturing method and assembling apparatus 1040 of the above-mentioned tampon 1001 will be described. It is to be noted that the structure whose description is omitted is similar to that of the first embodiment.

<<Structure of Tampon 1001>>

Figure 9A:
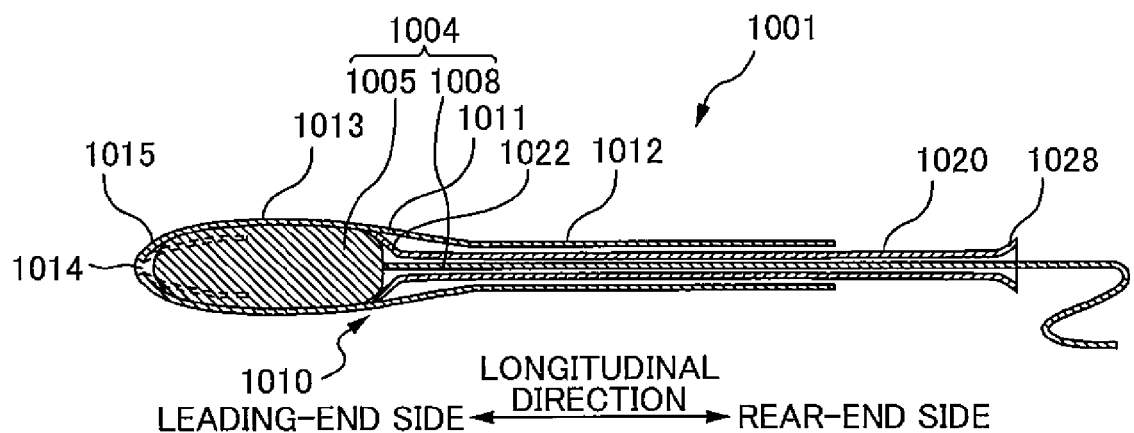
FIG. 9A is a cross-sectional view of a tampon 1001 of the second embodiment.
Figure 9B:
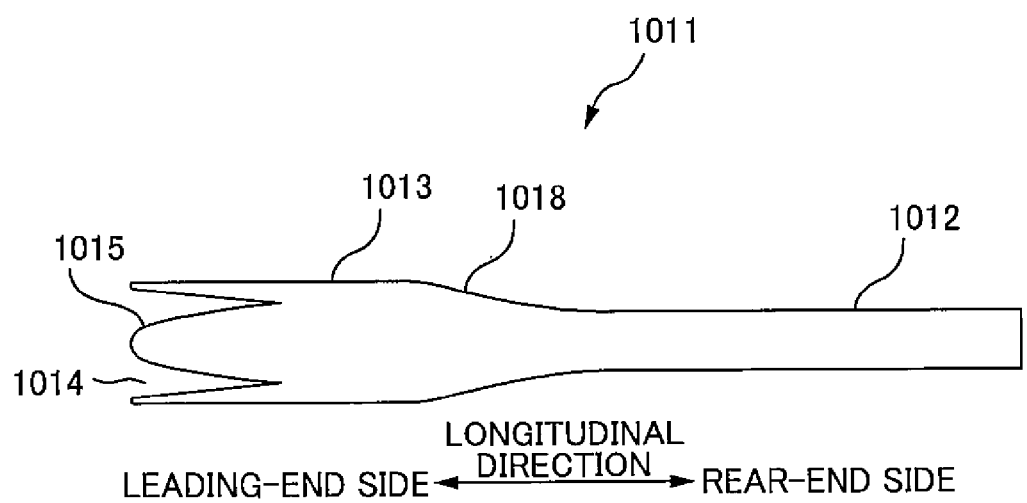
FIG. 9B is an elevation view of an outer cylinder 1011.

FIG. 9A is a cross-sectional view of a tampon 1001 of the second embodiment. FIG. 9B is an elevation view of an outer cylinder 1011. The tampon 1001 of the second embodiment has an external diameter smaller than that of the tampon 1001 of the first embodiment (FIG. 1A) and is designed to achieve an easier insertion into a vaginal cavity.

As shown in FIG. 9A, the tampon 1001 includes a tampon main body 1004 and an applicator 1010. The tampon main body 1004 has a structure that is similar to the tampon main body 1004 shown in FIG. 1A and includes an absorbent body 1005 and a cord 1008.

The applicator 1010 includes an outer cylinder 1011 and an inner cylinder 1020. As shown in FIG. 9B, the outer cylinder 1011 includes a minor diameter part 1012 and a major diameter part 1013. In a manner similar to the outer cylinder 1011 shown in FIG. 1A, the major diameter part 1013 includes a leading-end opening 1014 formed at the leading end and a plurality of petaloid parts 1015 surrounding the leading-end opening. On the other hand, the minor diameter part 1012 does not include an annular protrusion 1017 (FIG. 1A) formed thereon. The inner cylinder 1020 differs from the inner cylinder 1020 shown in FIG. 1A (the inner cylinder 1020 having the first inner cylinder 1021 and the second inner cylinder 1025) and includes a single inner cylinder only.

<<Manufacturing Method and Assembling Apparatus 1040 of Tampon 1001>>

The tampon 1001 of the above-mentioned structure is also manufactured in accordance with the manufacture flowchart shown in FIGS. 2A and 2B. However, since there is only one inner cylinder 1020, manufacturing is simplified as compared to the first embodiment. Also, when supplying the outer cylinder 1011 at the assembling apparatus 1040, the outer cylinder 1011 is oriented by the orienting mechanism 1060. The orienting mechanism 1060 of the second embodiment has a structure different from that of the first embodiment (FIG. 5). Therefore, in the following description, the structure of the orienting mechanism 1060 will be described.

Figure 10:
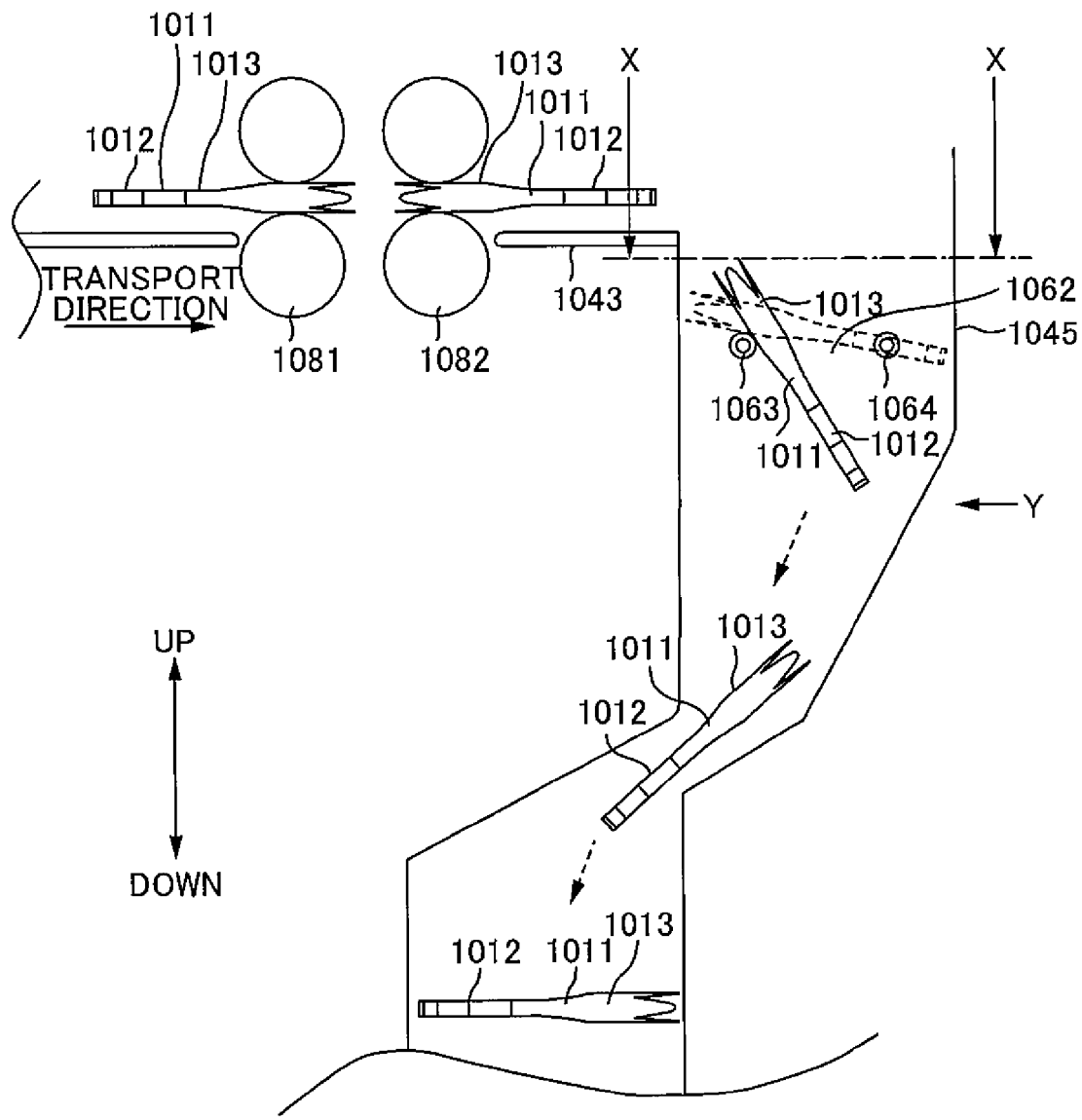
FIG. 10 is a diagram showing a drop chute 1045 of the second embodiment and a neighboring part thereof.
Figure 11A:
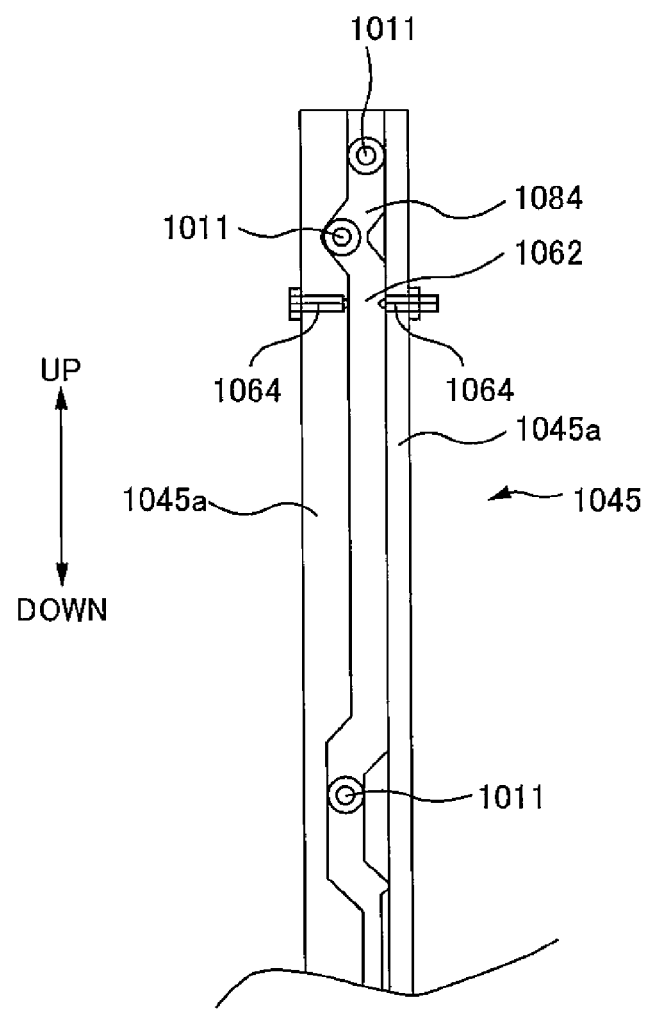
FIG. 11A is a partial cross-sectional view of the drop chute 1045 viewed in Y-direction shown in FIG. 10.
Figure 11B:
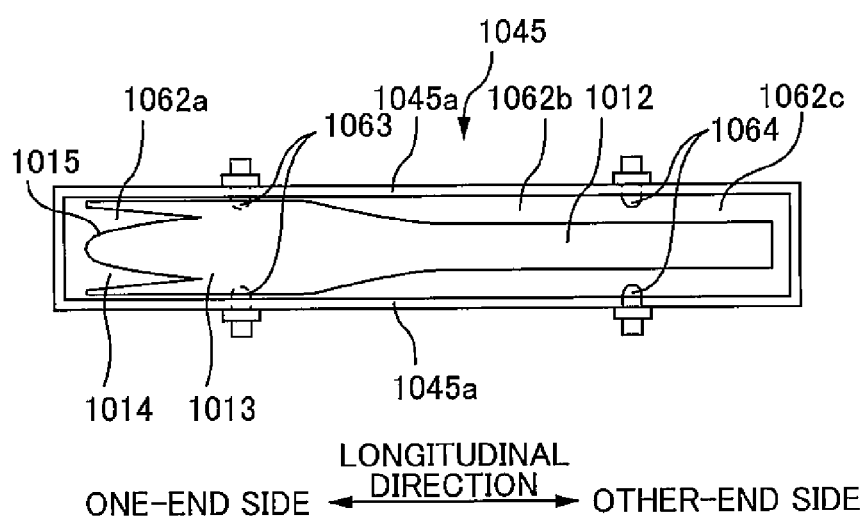
FIG. 11B is a cross-sectional view taken along line X-X in FIG. 10.

FIG. 10 is a diagram showing a drop chute 1045 of the second embodiment and the neighboring part thereof. FIG. 11A is a partial cross-sectional view of the drop chute 1045 viewed in Y-direction in FIG. 10. FIG. 11B is a cross-sectional view taken along line X-X in FIG. 10.

The drop chute 1045 does not include an orienting plate 1061 shown in FIG. 5. In stead, the first protruded parts 1063 and the second protruded parts 1064 are formed by pins protruding from a frame 1045a of the drop chute 1045. The first protruded parts 1063 and the second protruded parts 1064 are provided at the same level in a vertical direction. In the dropping path of the outer cylinder 1011 in the drop chute 1045, an opening 1062 corresponding to a plane passing through the first protruded parts 1063 and the second protruded parts 1064 is equivalent to the above-mentioned opening 1062. In a similar manner to the opening 1062 shown in FIG. 6, the opening 1062 is divided into a one-end opening 1062a, a central opening 1062b and an other-end opening 1062c (see FIG. 11B).

As shown in FIG. 11A, in the path of the drop chute 1045, a bent part 1084 is formed above the first protruded parts 1063 and the second protruded parts 1064. The outer cylinder 1011 that has proceeded into the drop chute 1045 (for example, the outer cylinder 1011 that has proceeded at an angle into the drop chute 1045) passes the bent part 1084 and thereby takes an attitude lying along the horizontal direction. Therefore, the minor diameter part 1012 and the major diameter part 1013 will be inputted into the opening 1062 at substantially the same time.

Two pairs of transport rollers 1081 and 1082 are provided on the transport path 1043 at the upstream side of the drop chute 1045 in the transport direction. The transport rollers 1081 and 1082 are pairs of rollers respectively that transport the outer cylinder 1011 while holding the outer cylinder 1011 between them. The outer cylinders 1011 transported through the transport path 1043 are arranged side-by-side and moves to the transport rollers 1081 and 1082. Here, the rotational speed of the transport rollers 1082 is greater than the rotational speed of the transport rollers 1081. Therefore, even if two outer cylinders 1011 that are supplied consecutively happen to join (for example, when the petaloid parts 1015 of the two consecutively supplied outer cylinders 1011 are in meshing engagement), the two outer cylinders 1011 can be separated by the transport rollers 1081 and 1082 and the outer cylinder 1011 can proceed into the drop chute 1045 one-by-one.

The orientation of the outer cylinder 1011 dropping in the drop chute 1045 of the above structure can be oriented in a manner described below.

As shown in FIG. 11B, when the outer cylinder 1011 is inputted into the opening 1062, since the external diameter of the major diameter part 1013 is greater than the gap between the first protruded parts 1063, the major diameter part 1013 comes into contact with the pair of first protruded parts 1063 and thus the major diameter part 1013 cannot pass between the pair of first protruded parts 1063. On the other hand, since the external diameter of the minor diameter part 1012 is smaller than the gap between the second protruded parts 1064, the minor diameter part 1012 starts passing between the pair of second protruded parts 1064. Thereafter, as shown in FIG. 10, with the major diameter part 1013 being in contact with the first protruded parts 1063, the minor diameter part 1012 completely passes between the second protruded parts 1064. Then, the major diameter part 1013 passes through the central opening 1062b to discharge the outer cylinder 1011 from the opening 1062 (that is to say, the minor diameter part 1012 is discharged first). In this manner, the outer cylinder 1011 is oriented in such a manner that its major diameter part 1013 is at an upper position and its minor diameter part 1012 is at a lower position.

It is to be noted that even if the outer cylinder 1011 is inputted in such a manner that the major diameter part 1013 comes into contact with the second protruded parts 1064, because the minor diameter part 1012 is discharged first, the outer cylinder 1011 will be oriented.

In this manner, also in the second embodiment, the outer cylinder 1011 can be supplied to the transport conveyor 1050 properly and rapidly because of the orienting mechanism 1060.

—Other Embodiments—

In the above-mentioned various embodiments, the manufacturing apparatus and the method of manufacturing the tampon of the present invention have been mainly discussed. However, the above-mentioned embodiments are provided for the purpose of facilitating the understanding of the present invention only and do not give any limitation to the present invention. It goes without saying that any modifications and improvements to the present invention can be made without departing from the spirit of the invention and the present invention includes its equivalents. Further, the above-mentioned configurations, etc., are merely examples to show effectiveness of the present invention and should not be understood as any limitation to the present invention.

In the above-mentioned embodiments, the inner cylinder 1020 of the tampon 1001 shown in FIG. 1A includes the first inner cylinder 1021 and the second inner cylinder 1025. However, the inner cylinder 1020 may include the first inner cylinder 1021 only.

Also, in the above-mentioned embodiments, the outer cylinder 1011 is oriented by dropping the outer cylinder 1011 shown in FIG. 9 onto the drop chute 1045 shown in FIG. 10, however, it is not limited thereto.

For example, the outer cylinder 1011 may be oriented by dropping the outer cylinder 1011 shown in FIG. 3A onto the drop chute 1045 shown in FIG. 10.

(Part Two)

First, a method of manufacturing a tampon including a tampon main body, an accommodating cylinder accommodating the tampon main body, the accommodating cylinder having an opening formed at a leading end and a plurality of petaloid parts surrounding the opening, and a pushing member that is movable in the accommodating member and pushes the tampon main body out of the accommodating cylinder through the opening, is provided, the method comprising:

performing a broadening process on the accommodating cylinder, the broadening process broadens the opening by outwardly bending each of the plurality of petaloid parts in the radial direction of the accommodating cylinder;

after performing the broadening process, inserting the pushing member into the accommodating cylinder through the opening; and after performing the broadening process, inserting the tampon main body into the accommodating cylinder through the opening. With such a method of manufacturing a tampon, the pushing member and the tampon main body can be smoothly inserted into the accommodating cylinder.

In the above method of manufacturing a tampon, the method may include: mounting the accommodating cylinder on a mounting jig that is placed on a transport conveyor and transported by the transport conveyor in the transport direction, and the broadening process is performed on the accommodating cylinder after mounting the accommodating cylinder on the mounting jig. With such a method of manufacturing a tampon, the broadening process is performed effectively.

In the above method of manufacturing a tampon, the broadening process may be a process of expanding the opening by inserting a tapered part of a jig provided at a leading-end part of the jig, the tapered part thickening from the leading-end side towards the rear end side, pressing the jig against each of the plurality of petaloid parts and bending the each of the plurality of petaloid parts outwardly in the radial direction. With such a method, the broadening process can be performed easily.

In the above method of manufacturing a tampon, in the performing of the broadening process, the jig is pressed against the each of the petaloid parts in such a manner that the each of the petaloid parts inclines outwardly in the radial direction at an angle of inclination between 1 degree and 45 degrees directly after the jig has been separated from each of the plurality of petaloid parts. With such a method, a disadvantage caused by an excessively large angle of inclination can be avoided.

In the above method of manufacturing a tampon, in mounting the accommodating cylinder onto the mounting jig, the accommodating cylinder is mounted on the mounting jig in such a manner that each of the plurality of petaloid parts is exposed from the leading end of the petaloid part to the rear end of the petaloid part. With such a method, since the jig can be properly pressed against each of the petaloid parts, the opening can be properly expanded.

In the above method of manufacturing a tampon, in the performing of the broadening process, the broadening process is performed a plurality of times on the accommodating cylinder. With such a method, the pushing member and the tampon main body can be inserted into the accommodating cylinder through the opening after securely broadening the opening.

In the above method of manufacturing a tampon, the performing of the broadening process includes:

performing the broadening process a plurality of times on the accommodating cylinder before inserting the pushing member into the accommodating cylinder; and performing the broadening process again on the accommodating cylinder during a period of after having inserted the pushing member into the accommodating cylinder and until the tampon main body is inserted into the accommodating cylinder. With such a method, upon insertion of each of the pushing member and the tampon main body into the accommodating cylinder, the opening can be more securely broadened.

Further, an apparatus for manufacturing a tampon including a tampon main body, an accommodating cylinder accommodating the tampon main body, the accommodating cylinder having an opening formed at a leading end and a plurality of petaloid parts surrounding the opening, and a pushing member that is movable in the accommodating member and pushes the tampon main body out of the accommodating cylinder through the opening, can be achieved, the apparatus including:

a broadening process mechanism that performs a broadening process on the accommodating cylinder, the broadening process broadens the opening by outwardly bending each of the plurality of petaloid parts in the radial direction of the accommodating cylinder;

a pushing member-inserting mechanism that, after performing the broadening process, inserts the pushing member into the accommodating cylinder through the opening; and a tampon main body-inserting mechanism that, after performing the broadening process, inserts the tampon main body into the accommodating cylinder through the opening. With such an apparatus for manufacturing a tampon, the pushing member and the tampon main body can be smoothly inserted into the accommodating cylinder.

In the above apparatus of manufacturing a tampon, the broadening process mechanism may include a jig that performs the broadening process;

the jig may include a tapered part that thickens from the leading end towards the rear end that is provided at the leading-end part of a jig and a projecting part that is provided at the rear-end part and projects outside of the outer edge of the rear end of the tapered part; and the broadening process mechanism may perform the broadening process that expands the opening by inserting the tapered part of the jig into the accommodating cylinder through the opening, pressing a surface that is located at the leading end of the projected part and that projects outside the outer edge against each of the plurality of petaloid parts and bending the each of the plurality of petaloid parts outwardly in the radial direction. With such a structure, the broadening process can be performed easily.

In the above apparatus of manufacturing a tampon, the broadening process mechanism may include another jig that has a configuration different from that of the jig;

the other jig including another tapered part broadening from the leading end towards the rear end and provided at the leading-end part;

the leading end of the tapered part provided on the jig being flat;

the leading end of the other tapered part provided on the other jig is more pointed than the leading end of the tapered part provided on the jig; and the broadening process mechanism performing, on the accommodating cylinder before performing the broadening process, other broadening process that expands the opening by inserting the other tapered part of the jig into the accommodating cylinder through the opening, pressing an outer peripheral surface against each of the plurality of petaloid parts and bending the each of the plurality of petaloid parts outwardly in the radial direction. With an above apparatus for manufacturing a tampon, by performing the other broadening process, the subsequent broadening process can be properly performed.

—Structure of a Tampon—

Before describing a method of manufacturing and a manufacturing apparatus of a tampon of the present invention, the structure of a tampon 2010 manufactured by the method of manufacturing and the manufacturing apparatus will be described with reference to FIGS. 12 to 17.

Figure 12:
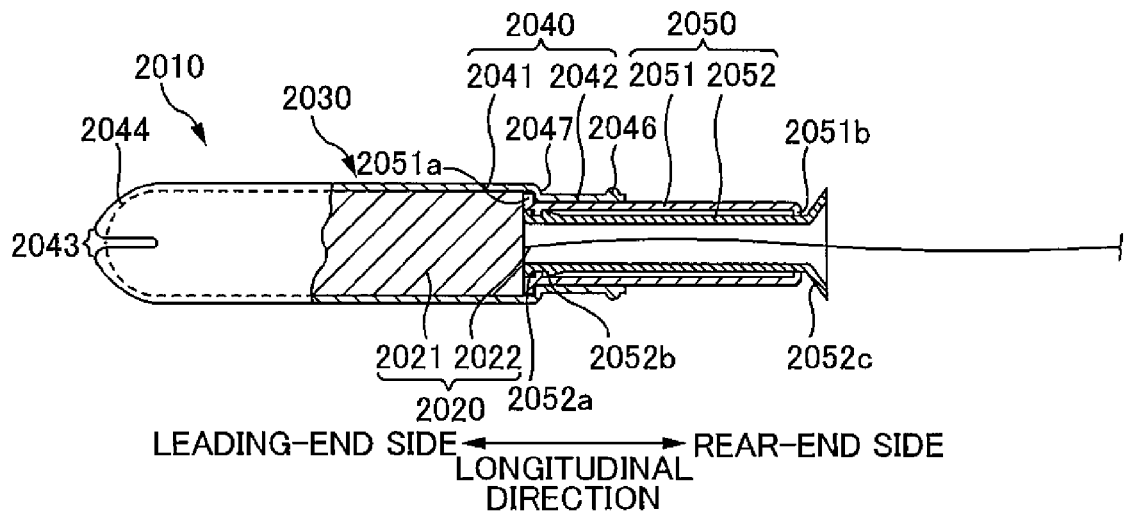
FIG. 12 is a cross-sectional view showing components of a tampon 2010.
Figure 13:
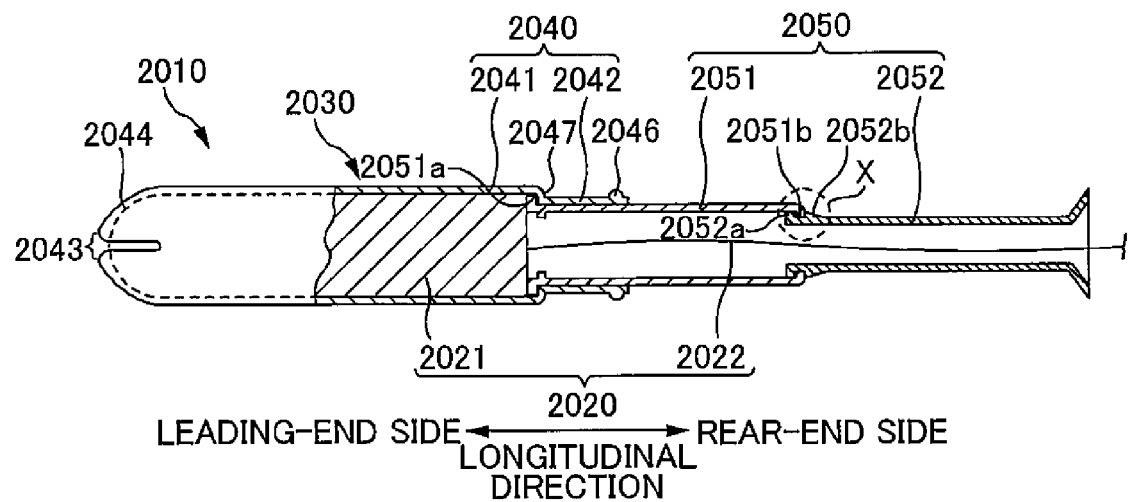
FIG. 13 is a cross-sectional view showing components of a tampon 2010.
Figure 14:
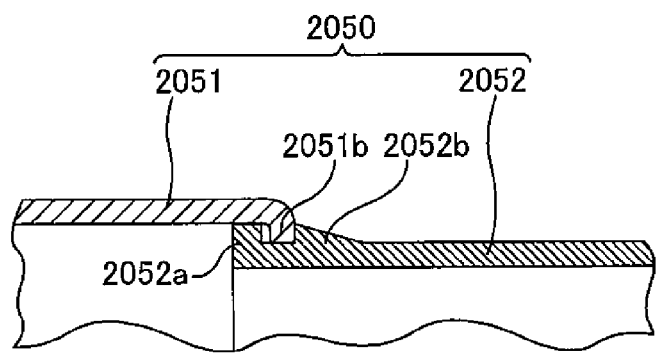
FIG. 14 is a diagram showing how a first inner cylinder 2051 and a second inner cylinder 2052 are joined.
Figure 15A:
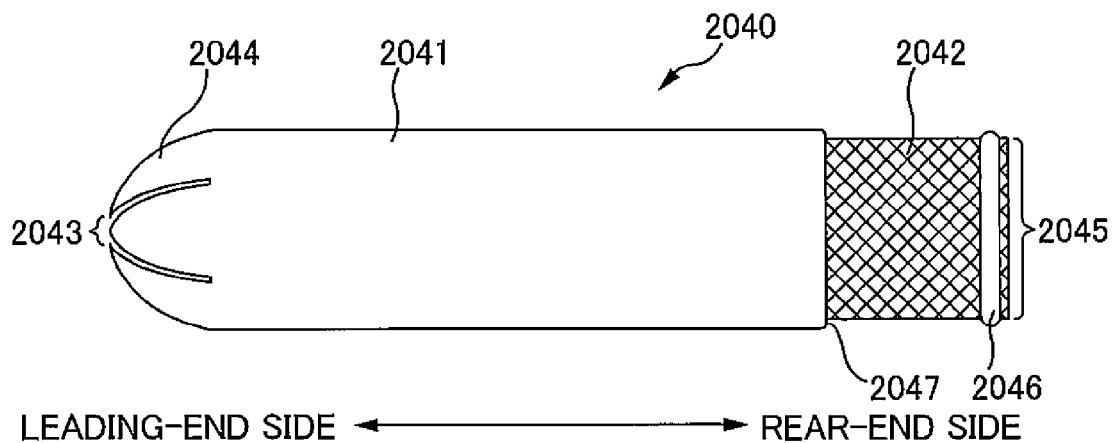
FIG. 15A is an external view of an outer cylinder 2040.
Figure 15B:
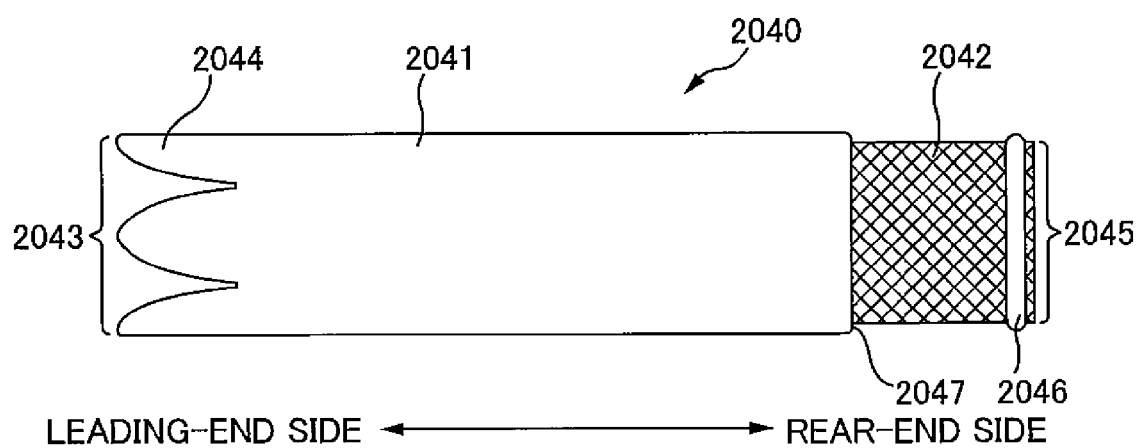
FIG. 15B is an external view of an outer cylinder 2040.
Figure 15C:
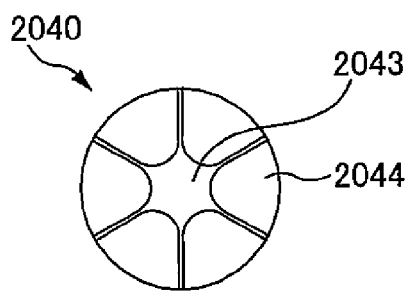
FIG. 15C is a diagram showing the outer cylinder 2040 shown in FIG. 15A from its leading-end side.
Figure 16:
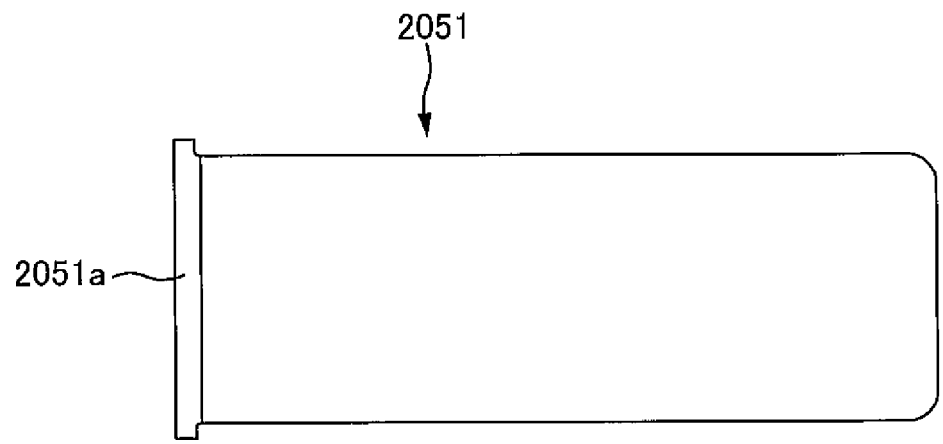
FIG. 16 is an external view of the first inner cylinder 2051.
Figure 17:
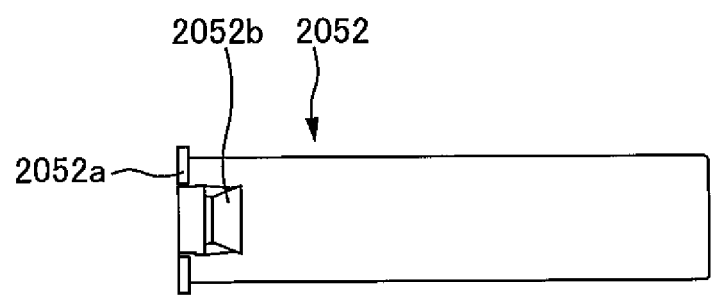
FIG. 17 is an external view of the second inner cylinder 2052.

FIGS. 12 and 13 are cross-sectional views showing the components of the tampon 2010. FIG. 12 shows the tampon 2010 in a state where an inner cylinder 2050 is contracted and FIG. 13 shows the tampon 2010 in a state where the inner cylinder 2050 is extended. FIG. 14 is a diagram showing how a first inner cylinder 2051 and a second inner cylinder 2052 are joined and is an enlarged view of the area labeled "X" in FIG. 13. FIGS. 15A and 15B are external views of an outer cylinder 2040. FIG. 15C is a diagram showing the outer cylinder 2040 shown in FIG. 15A from its leading-end side. FIG. 16 is an external view of the first inner cylinder 2051. FIG. 17 is an external view of the second inner cylinder 2052. In the following description, among the two end parts in the longitudinal direction of the tampon 2010, the side that is inserted in to the vaginal cavity is referred to as a leading-end side and the opposite side is referred to as a rear-end side.

As shown in FIG. 12, the tampon 2010 of the present embodiment is a sanitary product including a tampon main body 2020 and an applicator 2030. As shown in the same diagram, the tampon main body 2020 includes a cotton body 2021 and a cord 2022. The cotton body 2021 is an absorbent body that blocks the vaginal cavity and absorbs menstrual blood etc, and is formed by cutting a cotton strip covered with non-woven fabric on both sides and by shaping into a substantially bullet like shape by heat forming. The cord 2022 extends through the rear-end side of the cotton body 2021 and is then held by a user when the cotton body 2021 inside the vaginal cavity is pulled out of the vaginal cavity. As shown in FIG. 12, the cord 2022 extends through the applicator 2030 and somewhat extends out of the rear end of the applicator.

The applicator 2030 is an aid device for guiding the tampon main body 2020 (specifically, the cotton body 2021) into a vaginal cavity. As shown in FIG. 12, the applicator 2030 includes an outer cylinder 2040 which is an example of an accommodating cylinder that accommodates the tampon main body 2020 and an inner cylinder 2050 which is an example of a pushing member that pushes the tampon main body 2020 out of the outer cylinder 2040.

The outer cylinder 2040 is a cylindrical body formed by injection molding a thermoplastic resin and has an appropriate flexibility. The outer cylinder 2040 includes a major diameter part 2041 provided on the leading-end part and a minor diameter part 2042 provided at the rear-end part and having an external diameter that is smaller than that of the major diameter part 2041. The major diameter part 2041 is a part that has a slightly greater internal diameter than the diameter of the tampon main body 2020 and accommodates the tampon making body 2020 therein. The major diameter part 2041 is inserted into the vaginal cavity upon usage of the tampon 2010 with the tampon main body 2020 being accommodated therein. The tampon main body 2020 is accommodated in the major diameter part 2041 with its outer peripheral surface being in contact with the inner peripheral surface of the major diameter part 2041. The minor diameter part 2042 is a part held by a user when using the tampon 2010. It is to be noted that it is not necessary to provide the minor diameter part 2042 on the outer cylinder 2040.

As shown in FIGS. 15A and 15B, the outer cylinder 2040 includes an opening formed at its leading end (hereinafter referred to as a leading-end opening 2043) and a plurality of petaloid parts 2044 (in this embodiment, six petaloid parts) surrounding the leading edge opening 2043. When shipping the tampon 2010, each of the plurality of petaloid parts 2044 is inwardly bent in an arc in the radial direction of the outer cylinder 2040 as shown in FIG. 15A. Therefore, when the outer cylinder 2040 is inserted into the vaginal cavity, the leading-end part of the outer cylinder 2040 is substantially hemispherical as shown in FIGS. 12 and 13 and the leading-end opening 2043 is substantially in a closed state as shown in FIG. 15C. On the other hand, as for the outer cylinder 2040 shortly after being injection molded, each of the plurality of petaloid parts 2044 is open (i.e., along the central axis of the outer cylinder 2040, as shown in FIG. 15B), and the leading-end opening 2043 is in an open state.

Further, as shown in FIG. 15A, the outer cylinder 2040 includes an opening formed at its rear end (hereinafter, referred to as a rear-end opening 2045) and an annular rib 2046 provided at a position slightly towards the leading-end side than the rear-end opening 2045. Further, an annular stepped part 2047 is formed between the major diameter part 2041 and the minor diameter part 2042.

The inner cylinder 2050 is a cylindrical body inserted into the minor diameter part 2042 of the outer cylinder 2040. The inner cylinder 2050 is located at a position nearer to the rear end-side than the tampon main body 2020 in the outer cylinder 2040 and moves along the central axis of the outer cylinder 2040 to pushes the tampon main body 2020 from the rear towards the leading-end opening 2043. Thereby, the tampon main body 2020 pushes each of the plurality of petaloid parts 2044 outwardly in the radial direction of the outer cylinder 2040 (in other words, opens the leading-end opening 2043) and is pushed out of the outer cylinder 2040. That is to say, the inner cylinder 2050 is movable in the outer cylinder 2040 and has a push-out function to push the tampon main body 2020 out of the outer cylinder 2040 through the leading-end opening 2043.

It is to be noted that the inner cylinder 2050 of the present embodiment has an extendable structure to make the over all length of the tampon 2010 compact. In detail, when the inner cylinder 2050 is contracted as shown in FIG. 12, the length of the inner cylinder 2050 is shorter than the outer cylinder 2040 and becomes a length suitable for carrying the tampon 2010. On the other hand, when the inner cylinder 2050 extends as shown in FIG. 13, the length of the inner cylinder 2050 will become a length sufficient to push the tampon main body 2020 out of the outer cylinder 2040. As has been described above, in order to make the inner cylinder 2050 extendable, in this embodiment, the inner cylinder 2050 has a two-tier structure. In detail, as shown in FIG. 12, the inner cylinder 2050 of the present embodiment includes a first inner cylinder 2051 and a second inner cylinder 2052 that is slidably inserted into the first inner cylinder 2051.

The first inner cylinder 2051 is a cylindrical body formed by injection molding plastics. The first inner cylinder 2051 has an external diameter that is slightly smaller than the internal diameter of the minor diameter part 2042. As shown in FIG. 12, The first inner cylinder 2051 is slidably inserted in the minor diameter part 2042. As shown in FIG. 16, an annular flange part 2051a is formed on an outer peripheral surface of the leading-end part of the first inner cylinder 2051. The flange part 2051a has an external diameter that is slightly smaller than the major diameter part 2041 of the outer cylinder 2040 and engages an inner surface of the stepped part 2047, thereby preventing the inner cylinder 2050 from falling off from the rear-end opening 2045 of the outer cylinder 2040. When the inner cylinder 2050 pushes the tampon main body 2020 out of the outer cylinder 2040, the inner cylinder 2050 moves in such a manner that the outer peripheral surface of the flange part 2051a is in contact with the inner peripheral surface of the major diameter part 2041. Further, as shown in FIGS. 12 and 13, at the rear-end side on an inner peripheral surface of the first inner cylinder 2051, an annular protrusion 2051b extending inwardly in the radial direction of the first inner cylinder 2051 is provided.

The second inner cylinder 2052 is a cylindrical body formed by injection molding a thermoplastic resin. The second inner cylinder 2052 has an external diameter that is slightly smaller than the internal diameter of the first inner cylinder 2051. The second inner cylinder 2052 is, when the inner cylinder 2050 is in a contracted state, inserted in the first inner cylinder 2051 as shown in FIG. 12 and, when the inner cylinder 2050 is in an extended position, connected to the rear-end part of the first inner cylinder 2051 at the leading-end part of the second inner cylinder 2052 as shown in FIG. 13. Further, as shown in FIG. 17, on the outer peripheral surface of the leading-end part of the second inner cylinder 2052, an arcuate flange part 2052a and a protruded part 2052b located nearer to the rear-end side than the flange part 2052a is formed. As shown in FIG. 14, the height of the protruded part 2052b becomes lower at the rear-end. It is to be noted that the gap between the flange part 2052a and the protruded part 2052b of the second inner cylinder 2052 is thicker than the thickness of the annular protrusion 2051b of the first inner cylinder 2051.

When the second inner cylinder 2052 is pulled towards the rear-end part, the annular protrusion 2051b of the first inner cylinder 2051 will be located between the flange part 2052a of the second inner cylinder 2052 and the protruded part 2052b. In such a state, as shown in FIG. 14, the annular protrusion 2051b engages the flange part 2052a and the protruded part 2052b and thereby the first inner cylinder 2051 and the second inner cylinder 2052 are joined.

Further, as shown in FIGS. 12 and 13, a flared part 2052c is formed at the rear end of the second inner cylinder 2052. Preferably, the external diameter of the flared part 2052c is greater than the internal diameter of the first inner cylinder 2051 and greater than the internal diameter of the minor diameter part 2042 of the outer cylinder 2040.

—Method of Manufacturing a Tampon 2010—

<<Outline of a Method of Manufacturing the Tampon 2010>>

Figure 18:
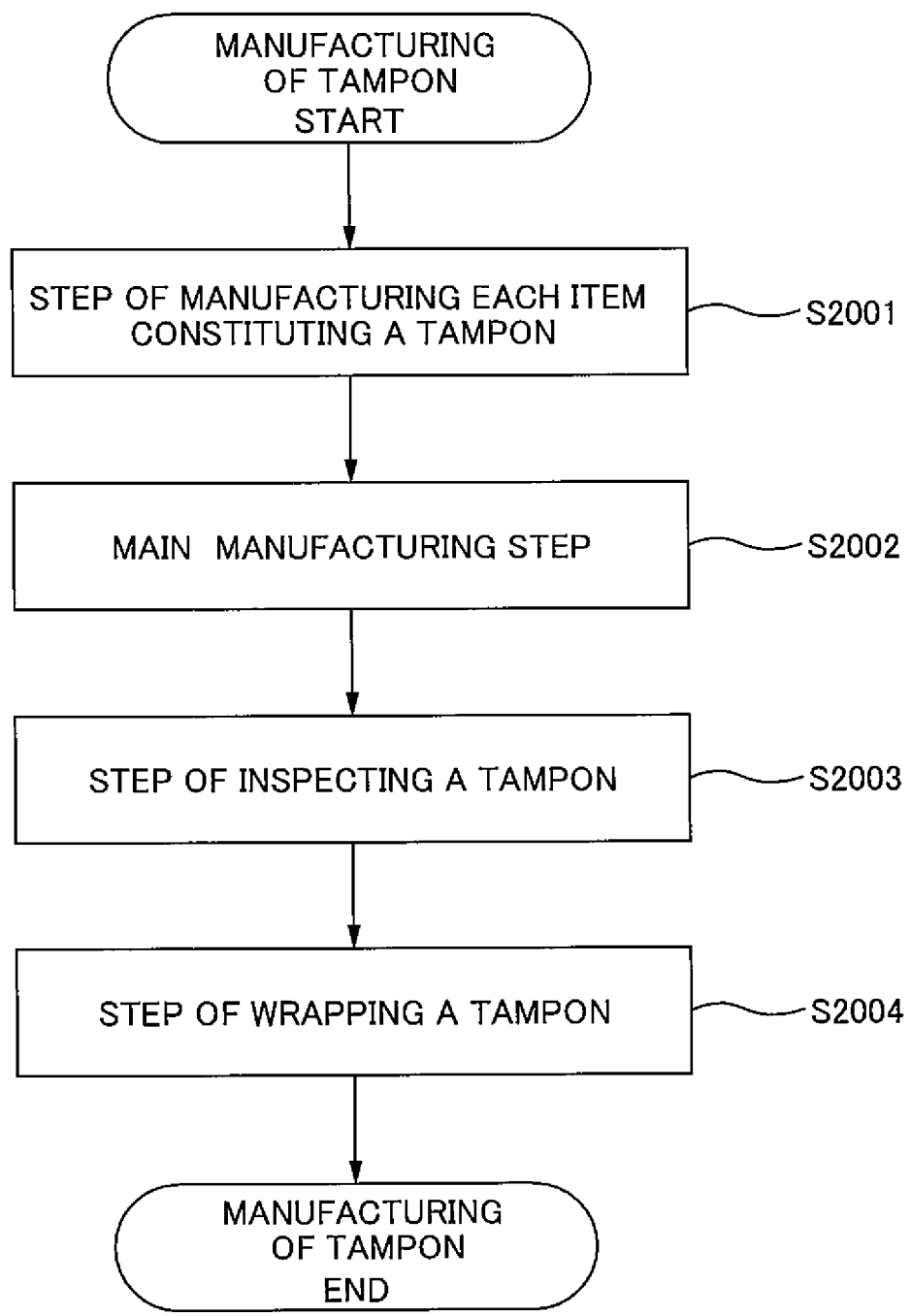
FIG. 18 is a flow chart of the manufacturing of the tampon 2010.

Next, a method of manufacturing the tampon 2010 of the present embodiment will be described with reference to FIG. 18 and FIGS. 19A to 19D. FIG. 18 is a flowchart showing how the tampon 2010 is manufactured.

FIGS. 19A to 19D are diagrams in a series showing how the tampon 2010 is manufactured.

As shown in FIG. 18, the method of manufacturing the tampon 2010 includes a step of manufacturing each item constituting the tampon 2010 (S2001), a step of supplying the manufactured items to an assembly apparatus 2100 to be described later and to manufacture the tampon 2010 by assembling the tampon 2010 (S2002), a step of inspecting the manufactured tampon 2010 (S2003) and a step of wrapping the tampon 2010 (S2004).

Figure 19A:
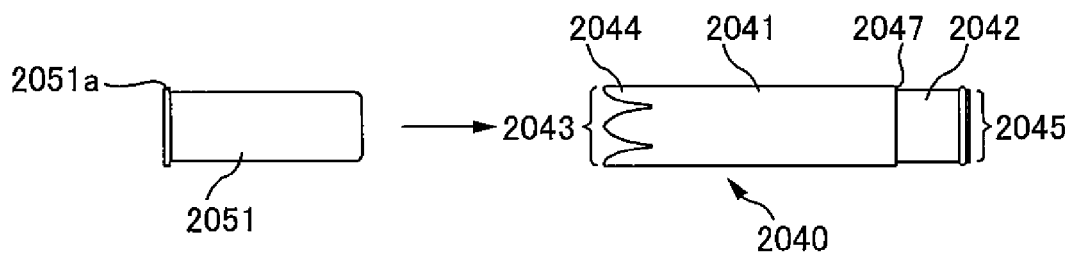
FIGS. 19A to 19D are diagrams in a series showing how the tampon 2010 is manufactured.

In the main manufacturing step S2002, firstly, each of the items constituting the tampon 2010 is supplied to the assembling apparatus 2100. As shown in FIG. 19A, at the time supplied to the assembling apparatus 2100, the outer cylinder 2040 is in a state where the plurality of petaloid part 2044 are each in an open state (in other words, the leading-end opening 2043 is open). Then, as shown in FIG. 19A, the first inner cylinder 2051 is inserted into the outer cylinder 2040 through the leading-end opening 2043 of the outer cylinder 2040. The first inner cylinder 2051 inserted in the outer cylinder 2040 will be in a state where its rear-end part protrudes through the rear-end opening 2045 of the outer cylinder 2040 and the flange part 2051a engages with the inner wall of the stepped part 2047 of the outer cylinder 2040 (see FIG. 19B).

Figure 19B:
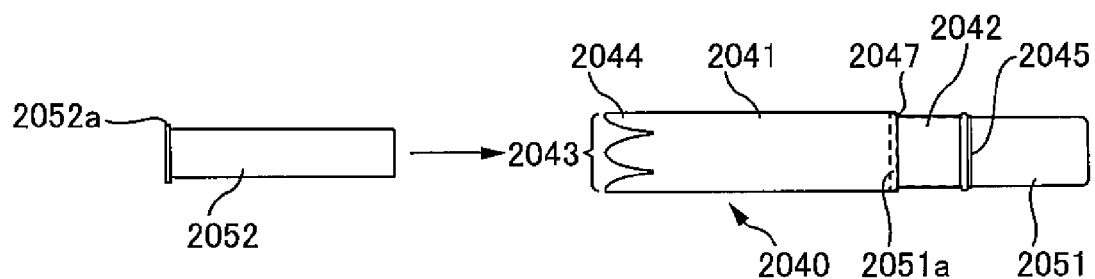

Then, as shown in FIG. 19B, the second inner cylinder 2052 is inserted into the outer cylinder 2040 through the leading-end opening 2043. The second inner cylinder 2052 inserted into the outer cylinder 2040 will be in a state where its rear-end part protrudes through the opening on the rear-end side of the first inner cylinder 2051 and the flange part 2052a engages with the inner peripheral surface of the first inner cylinder 2051 (see FIG. 19C). It is to be noted that, as shown in FIG. 19B, at the time the second inner cylinder 2052 is supplied to the assembling apparatus 2100, a flared part 2052c is not yet formed on the second inner cylinder 2052. After the second inner cylinder 2052 has been inserted into the outer cylinder 2040, the flared part 2052c is formed by heat forming the rear-end part of the second inner cylinder 2052. When the above-described steps are terminated, the assembly of the applicator 2030 is complete.

Figure 19C:
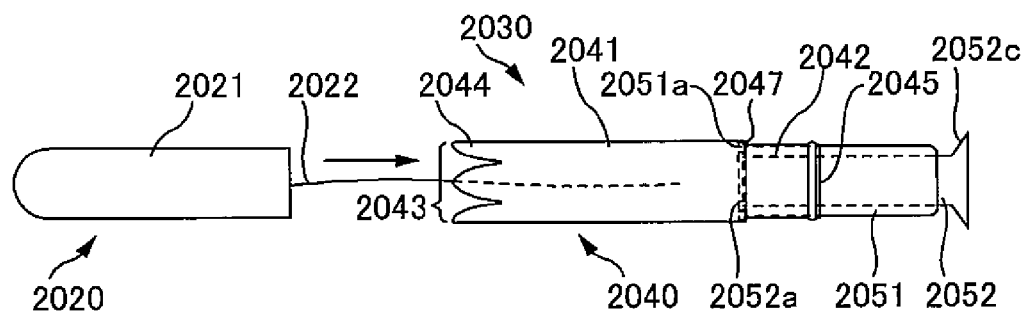

Then, as shown in FIG. 19C, the tampon main body 2020 is inserted into outer cylinder 2040 through the leading-end opening 2043. Here, as shown in FIG. 19C, the tampon main body 2020 is inserted from its cord 2022 side. When the tampon main body 2020 is inserted in the outer cylinder 2040, the cotton body 2021 is accommodated in the major diameter part 2041 of the outer cylinder 2040 and the cord 2022 extends out of the rear end of the applicator 2030 (specifically, out of the opening on the rear-end of the second inner cylinder 2052.) When insertion of the tampon main body 2020 is terminated, the assembly of the tampon 2010 is complete.

Figure 19D:
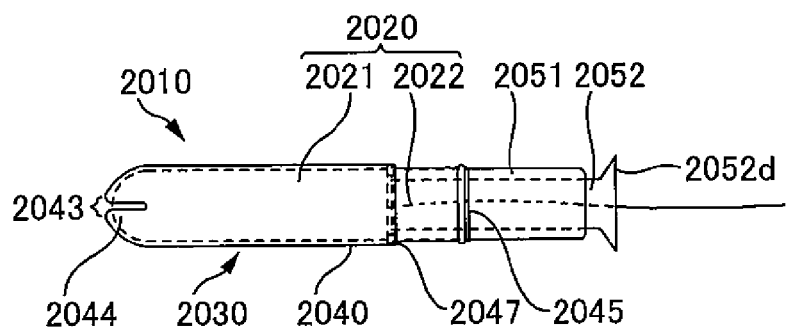

After assembling the tampon 2010, as shown in FIG. 19D, a process of heat forming is performed in which the leading-end part of the outer cylinder 2040 is formed into a substantially hemispherical shape by bending each of the plurality of petaloid parts 2044 in such a manner that it is inclined inwardly in the radial direction of the outer cylinder 2040 (hereinafter referred to as a leading-end processing). When the leading-end processing is terminated, the main manufacturing step S2002 is complete.

It is to be noted that, as described below, the assembling apparatus 2100 includes a transport conveyor 2110 (see FIG. 20). This transport conveyor 2110 intermittently carries out motions of transporting the assembled products in the transport direction (transport motions). Between the transport motions, i.e., when the assembled item is in a rest, each of the above-mentioned steps is sequentially performed.

<<Assembling Step of the Tampon 2010>>

Next, regarding the above-mentioned main manufacturing step S2002, a step of assembling the tampon 2010 will be described in detail with reference to FIG. 20. FIG. 20 is a diagram showing the assembling apparatus 2100 of the tampon 2010.

<Assembling Apparatus 2100 of Tampon 2010>

Figure 20:
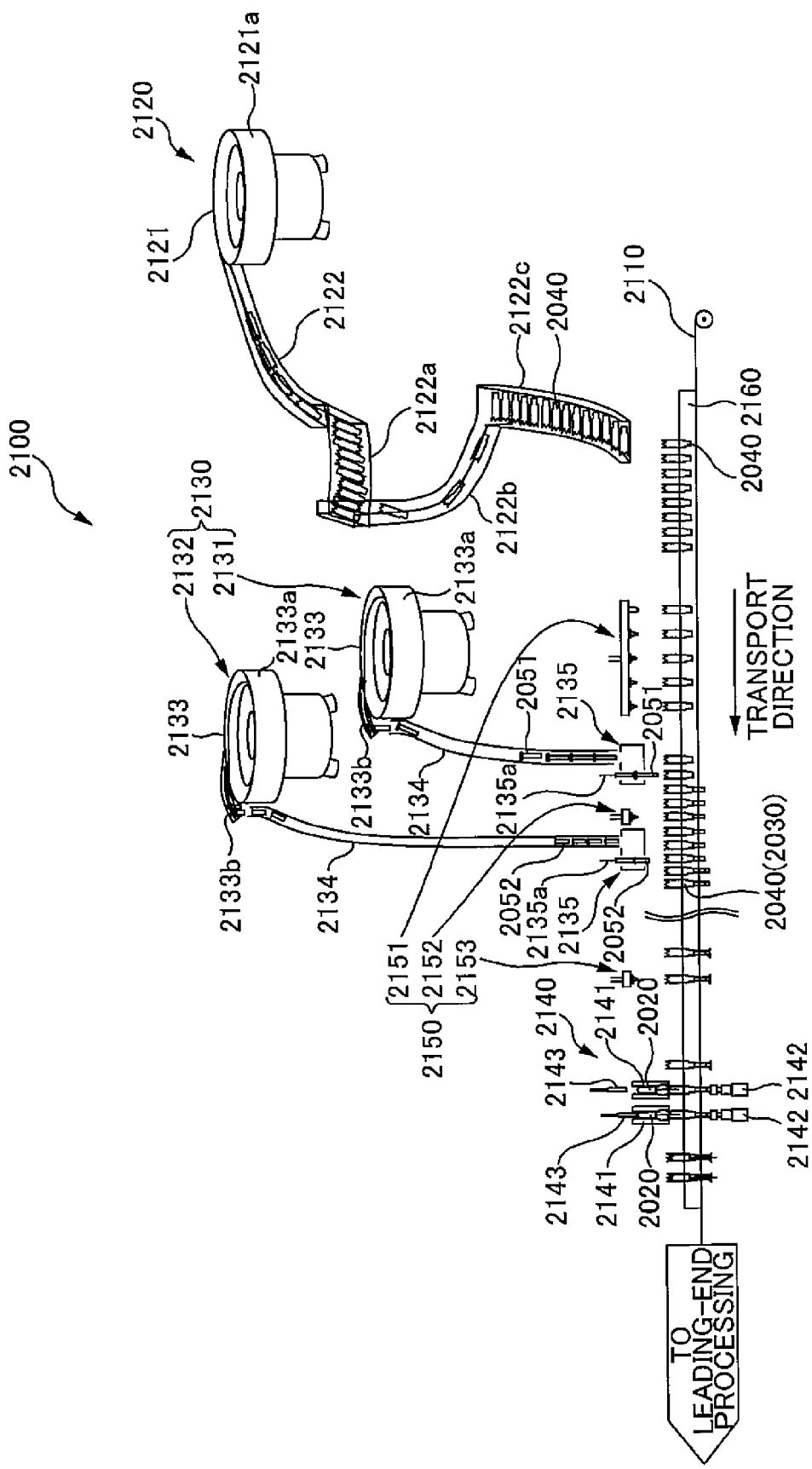
FIG. 20 is a diagram showing an assembling apparatus 2100 of the tampon 2010.

The step of assembling the tampon 2010 is performed by the assembling apparatus 2100 shown in FIG. 20. This assembling apparatus 2100 is an example of an apparatus for manufacturing the tampon 2010. As shown in FIG. 20, the assembling apparatus 2100 includes a transport conveyor 2110, an outer cylinder supplying mechanism 2120, an inner cylinder inserting mechanism 2130 as an example of the pushing-member inserting mechanism, a tampon main body inserting mechanism 2140 and a broadening mechanism 2150. Hereinafter, each device constituting the assembling apparatus 2100 will be described.

(1) Transport Conveyor 2110

The transport conveyor 2110 is a device that transports the outer cylinder 2040 and items inserted in the outer cylinder 2040 (first inner cylinder 2051, second inner cylinder 2052 and tampon main body 2020) in the transport direction (direction shown by an arrow in FIG. 20). A mount 2160 that mounts the outer cylinder 2040 thereon is placed on the transport conveyor 2110 and the mount 2160 is transported in the transport direction by the transport conveyor 2110. Thereby, the outer cylinder 2040 mounted on the mount 2160 and the items inserted in the outer cylinder 2040 are transported in the transport direction together with the mount 2160.

The mount 2160 is an example of a mounting jig and, as shown in FIG. 20, the outer cylinder 2040 is mounted thereon with the central axis of the outer cylinder 2040 lying along the vertical direction and the leading-end opening 2043 being facing substantially directly upwards. Circular holes (not shown) are formed in the mount 2160 in the vertical direction. The outer cylinder 2040 is mounted on the mount 2160 by being fitted into the circular hole from the minor diameter part 2042 side.

Figure 21:
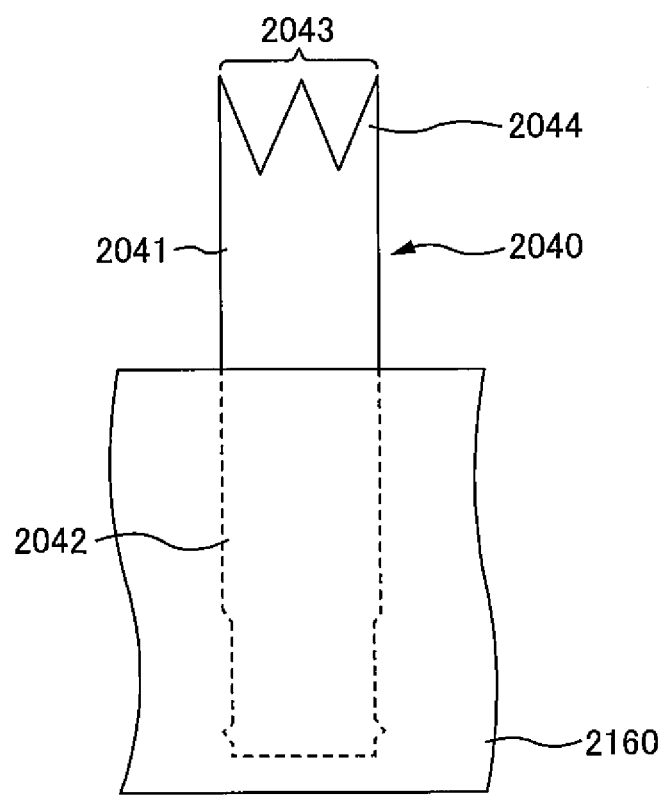
FIG. 21 is a diagram showing a state where the outer cylinder 2040 is mounted on a mount 2160.

In this embodiment, as shown in FIG. 21, in a state where the outer cylinder 2040 is mounted on the mount 2160, substantially half of the leading-end side of the outer cylinder 2040 is exposed. Therefore, in the state where the outer cylinder 2040 is mounted on the mount 2160, each of the plurality of the petaloid parts 2044 is exposed from the leading end of the petaloid part 2044 to the rear end of the petaloid part 2044. FIG. 21 is a diagram showing the outer cylinder 2040 that is mounted on the mount 2160.

(2) Outer Cylinder Supplying Mechanism 2120

The outer cylinder supplying mechanism 2120 is a mechanism that supplies the outer cylinder 2040 to the transport conveyor 2110. As shown in FIG. 20, the outer cylinder supplying mechanism 2120 includes an outer cylinder transport feeder 2121, a supplying path 2122 connected to the end of the transport path included in the outer cylinder transport feeder 2121, and an outer cylinder setting part (not shown) that sets the outer cylinder 2040 that has passed through the supplying path 2122 to the mount 2160.

The outer cylinder transport feeder 2121 is a parts feeder having a bowl-shaped vibratory table 2121a and transports the outer cylinder 2040 by vibrating the vibratory table 2121a. In detail, the vibratory table 2121a forms a spiral transport path. By vibrating the vibratory table 2121a, the outer cylinder transport feeder 2121 moves the outer cylinders 2040 accumulated at the base of the vibratory table 2121a sequentially from the base and along the transport path. The outer cylinder 2040 that has reached the end of the transport path is passed to the supplying path 2122 and travels on the supplying path 2122.

As shown in FIG. 20, at the middle part and the end part of the supplying path 2122, accumulating parts 2122a and 2122c that temporarily accumulate the outer cylinders 2040 are provided. A drop chute 2122b is formed between the accumulating parts 2122a and 2122c. The outer cylinders 2040 accumulated in the accumulating part 2122a provided at the middle part of the supplying path 2122 sequentially drop in the drop chute 2122b. It is to be noted that in the drop chute 2122b, a restriction mechanism (not shown) that restricts the orientation of the outer cylinder 2040 into a predetermined orientation is provided. While passing through the drop chute 2122b, the outer cylinder 2040 is subjected to the action of the restriction mechanism and its orientation is restricted in such a manner that its leading-end comes out of the drop chute 2122b first.

Then, the outer cylinders 2040 that came out of the drop chute 2122b are accumulated in the accumulating part 2122c provided at the end part of the supplying path 2122 in such a manner that the outer cylinders 2040 are oriented in the same orientation. The accumulating part 2122c provided at the end of the supplying path 2122 is inclined with a downward slope. The outer cylinder 2040 that has slid down the accumulating part 2122c and reached the end of the supplying path 2122 is captured at the above-mentioned outer cylinder setting part. Then, the outer cylinder setting part mounts the caught outer cylinder 2040 onto the mount 2160 placed on the transport conveyor 2110.

(3) Inner Cylinder Inserting Mechanism 2130

The inner cylinder inserting mechanism 2130 is a mechanism that inserts the inner cylinder 2050 into the outer cylinder 2040. In the present embodiment, after the broadening mechanism 2150 has performed the broadening process which is to be described later, the inner cylinder inserting mechanism 2130 inserts the inner cylinder 2050 through the leading-end opening 2043 of the outer cylinder 2040 into the outer cylinder 2040 that is mounted on the mount 2160. Further, the inner cylinder inserting mechanism 2130 each includes a mechanism that inserts the first inner cylinder 2051 constituting the inner cylinder 2050 into the outer cylinder 2040 (hereinafter referred to as the first inner cylinder inserting mechanism 2131) and a mechanism that inserts the second inner cylinder 2052 also constituting the inner cylinder 2050 into the outer cylinder 2040 (hereinafter referred to as the second inner cylinder inserting mechanism 2132).

As shown in FIG. 20, the first inner cylinder inserting mechanism 2131 includes an inner cylinder transport feeder 2133, an inner cylinder inserting part 2135 that inserts the first inner cylinder 2051 into the outer cylinder 2040 and a supplying tube 2134 provided between the inner cylinder transport feeder 2133 and the inner cylinder inserting part 2135.

The inner cylinder transport feeder 2133 is a parts feeder having a structure substantially similar to the outer cylinder transport feeder 2121 and moves the first inner cylinders 2051 sequentially from the base of the bowl-shaped vibratory table 2133a and along the spiral transport path formed by the vibratory table 2133a. In the present embodiment, as shown in FIG. 20, the terminal end part of the transport path is constructed by a pair of rails 2133b. The pair of rails 2133b is a part of the vibratory table 2133a.

Between the pair of rails 2133b, a gap that is slightly longer than the external diameter of the first inner cylinder 2051 is formed. The first inner cylinder 2051 is held between the pair of rails 2133b and travels along the rails 2133b. During this, the flange part 2051a of the first inner cylinder 2051 hangs at the top part of the rails 2133b and the first inner cylinder 2051 is suspended from the rails 2133b. That is to say, when the first inner cylinder 2051 travels along the rails 2133b, the leading-end of the first inner cylinder 2051 is situated above the rear end. Then, after passing the leading end of the rails 2133b, the first inner cylinder 2051 drops with its leading-end being located above the rear-end and is supplied to the inner cylinder inserting part 2135 through the supplying tube 2134.

The inner cylinder inserting part 2135 receives the first inner cylinder 2051 that has dropped through the supplying tube 2134 and, when the outer cylinder 2040 is at a position below the inner cylinder inserting part 2135, presses down the first inner cylinder 2051 it has received and inserts the first inner cylinder 2051 into the outer cylinder 2040. In detail, as shown in FIG. 20, the inner cylinder inserting part 2135 includes a pressing member 2135a that is movable in the vertical direction. By moving the pressing member 2135a downwards when situated above the first inner cylinder 2051, the first inner cylinder 2051 is pressed downwards. The inner cylinder inserting part 2135 inserts the first inner cylinder 2051 into the outer cylinder 2040 through the leading-end with the leading-end of the first inner cylinder 2051 being situated above the rear-end.

Detailed description of the structure of the second inner cylinder inserting mechanism 2132 will be omitted since the second inner cylinder inserting mechanism 2132 has a structure substantially similar to that of the first inner cylinder inserting mechanism 2131. As shown in FIG. 20, the inner cylinder inserting part 2135 provided in the second inner cylinder inserting mechanism 2132 to insert the second inner cylinder 2052 into the outer cylinder 2040 is provided downstream in the transport direction of the transport conveyor 2110 of the inner cylinder inserting part 2135 provided in the first inner cylinder inserting mechanism. 2131. That is to say, after the first inner cylinder inserting mechanism 2131 has inserted the first inner cylinder 2051 into the outer cylinder 2040, the second inner cylinder inserting mechanism 2132 inserts the second inner cylinder 2052 into the outer cylinder 2040.

(4) Tampon Main Body Inserting Mechanism 2140

The tampon main body inserting mechanism 2140 is a mechanism that inserts the tampon main body 2020 into the outer cylinder 2040 in which the first inner cylinder 2051 and the second inner cylinder 2052 have been inserted (in other words, the assembled applicator 2030). It is to be noted that, after the broadening mechanism 2150 has performed the broadening process described below, the tampon main body inserting mechanism 2140 of the present embodiment inserts the tampon main body 2020 through the leading-end opening 2043 into the outer cylinder 2040 mounted on the mount 2160.

As shown in FIG. 20, the tampon main body inserting mechanism 2140 includes a guide tube 2141, a suction device 2142 and a pressing member 2143. As shown in FIG. 20, the guide tube 2141 is a cylindrical body that covers the leading-end part of the outer cylinder 2040. The guide tube 2141 is movable in the vertical direction with its central axis lying along the vertical direction. Further, the guide tube 2141 holds the tampon main body 2020 in its inner space. It is to be noted that the tampon main body 2020 is inserted into the guide tube 2141 by an inserting mechanism (not shown) and, as shown in FIG. 20, held within the guide tube 2141 with the cord 2022 being situated below the cotton body 2021.

The suction device 2142 takes the air in from the rear-end side of the outer cylinder 2040 (specifically, from an opening at the rear-end side of the second inner cylinder 2052 inserted in the outer cylinder 2040) when the guide tube 2141 covers the leading-end of the outer cylinder 2040. The pressing member 2143 is situated directly above the upper-end opening of the guide tube 2141 and is held in a vertically movable manner. When the lower-end part of the guide tube 2141 covers the leading-end part of the outer cylinder 2040, the pressing member 2143 is inserted into the guide tube 2141 through the upper-end opening of the guide tube 2141. Thus, the pressing member 2143 presses down the tampon main body 2020 held in the guide tube 2141 and inserts the tampon main body 2020 into the outer cylinder 2040 through the leading-end opening 2043 of the outer cylinder 2040.

When the outer cylinder 2040 is situated at a position where the leading-end opening 2043 opposes the lower-end opening of the guide tube 2141, the tampon main body inserting mechanism 2140 of the above-mentioned structure moves the guide tube 2141 downwards. Thus the lower-end part of the guide tube 2141 covers the leading-end of the outer cylinder 2040. The tampon main body inserting mechanism 2140 presses down the tampon main body 2020 held in the guide tube 2141 by the pressing member 2143. As a result, the tampon main body 2020 is pushed out from the guide tube 2141 and is inserted into the outer cylinder 2040 through the leading-end opening 2043 of the outer cylinder 2040.

It is to be noted that the tampon main body inserting mechanism 2140 operates the suction device 2142 when pushing the tampon main body 2020 out of the guide tube 2141. Accordingly, when the tampon main body 2020 is inserted into the outer cylinder 2040, the cord 2022 of the tampon main body 2020 is pulled downwards. As a result, the cord 2022 extends through the outer cylinder 2040 and is pulled out of the opening at the rear-end side of the second inner cylinder 2052 inserted in the outer cylinder 2040 (in other words, pulled out from the rear-end of the assembled applicator 2030).

(5) Broadening Mechanism 2150

A broadening process is performed as a pre-process before inserting the inner cylinder 2050 and tampon main body 2020 into the outer cylinder 2040 and the broadening mechanism 2150 is a mechanism that performs the broadening process on the outer cylinder 2040. The broadening process is a process that broadens the leading-end opening 2043 by bending each of the plurality of petaloid parts 2044 surrounding the leading-end opening 2043 of the outer cylinder 2040 outwardly in the radial direction. In this embodiment, as shown in FIG. 20, the broadening mechanism 2150 includes a first pusher unit 2151, a second pusher unit 2152 and a third pusher unit 2153.

Figure 22A:
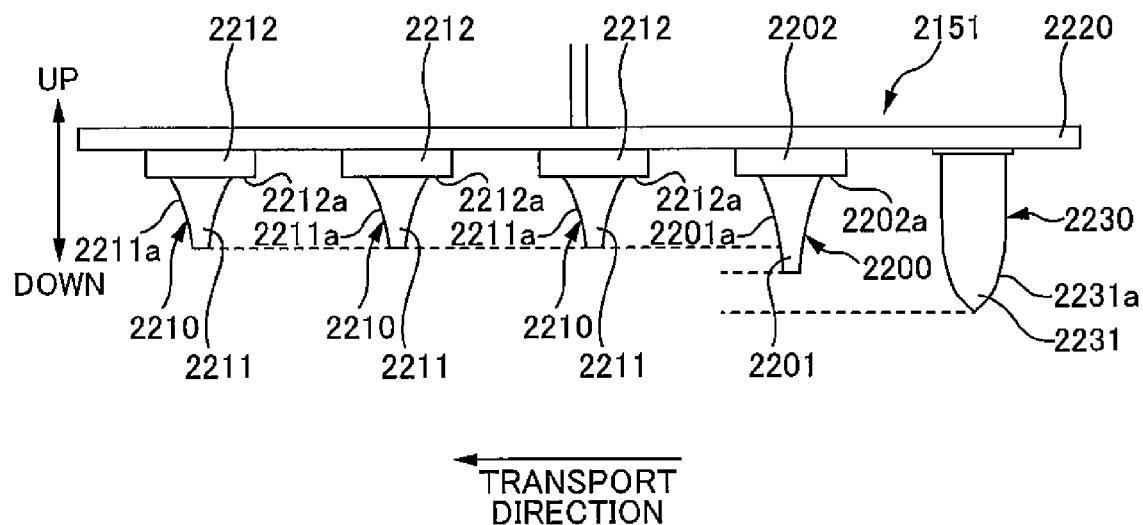
FIG. 22A is a diagram showing a first pusher unit 2151.

The first pusher unit 2151 performs the broadening process on the outer cylinder 2040 before the first inner cylinder 2051 is inserted into the outer cylinder 2040. The first inner cylinder 2051 is located on the upstream side than the first inner cylinder inserting mechanism 2131 in the transport direction of the transport conveyor 2110. As shown in FIG. 22A, the first pusher unit 2151 includes a plurality of pushers 2200 and 2210 (in this embodiment, four pushers), an attachment plate 2220 on which the plurality of pushers 2200 and 2210 are mounted and a driving mechanism (not shown) that reciprocates the attachment plate 2220 in the vertical direction. FIG. 22A is a diagram showing the first pusher unit 2151.

The pushers 2200 and 2210 are an example of a jig for the first pusher unit 2151 to perform the broadening process on the outer cylinder 2040 and, in the present embodiment, made of metal. As shown in FIG. 22A, the plurality of pushers 2200 and 2210 are provided in a line in the transport direction.

When the outer cylinder 2040 comes into a position directly below one of the pushers 2200 and 2210 of the plurality of pushers 2200 and 2210, the first pusher unit 2151 moves the plurality of pushers 2200 and 2210 downwardly together with the attachment plate 2220 by the driving mechanism. Thus, the leading-end parts of the pushers 2200 and 2210 are inserted into the outer cylinder 2040 through the leading-end opening 2043 of the outer cylinder 2040 and the pushers 2200 and 2210 are pushed against each of the inner surfaces of the plurality of petaloid parts 2044. As a result, each of the plurality of petaloid parts 2044 is bent outwards in the radial direction of the outer cylinder 2040 by the pushers 2200 and 2210 and thus the leading-end opening 2043 is expanded.

As has been described above, the broadening process of the present embodiment is a process that inserts the leading-end parts of the pushers 2200 and 2210 into the outer cylinders 2040 through the leading-end opening 2043, presses the pushers 2200 and 2210 against each of the plurality of petaloid parts 2044 and mechanically expands the leading-end openings 2043 by outwardly bending each of the petaloid parts 2044 by the pressure force that is applied to each of the petaloid parts 2044.

Figure 23:
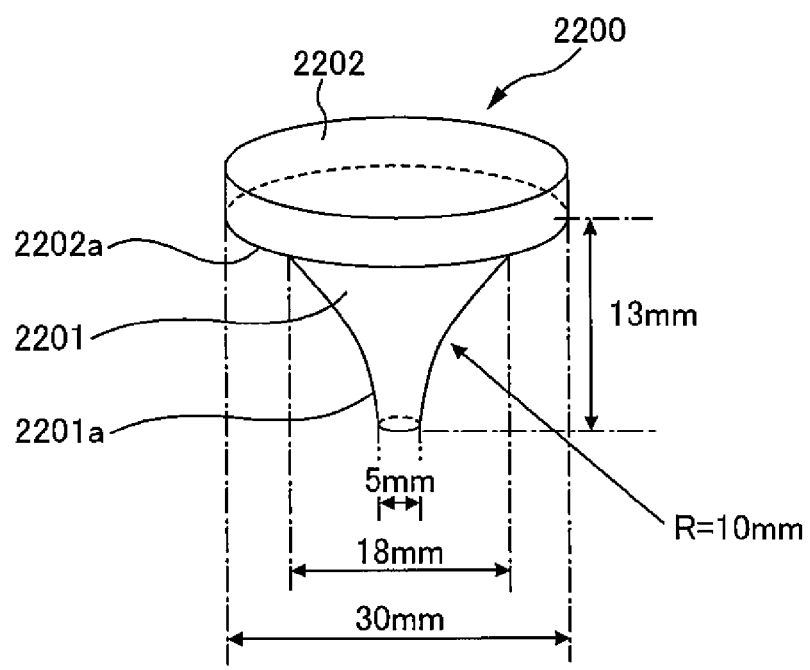
FIG. 23 is an external view of a pusher 2200.
Figure 24:
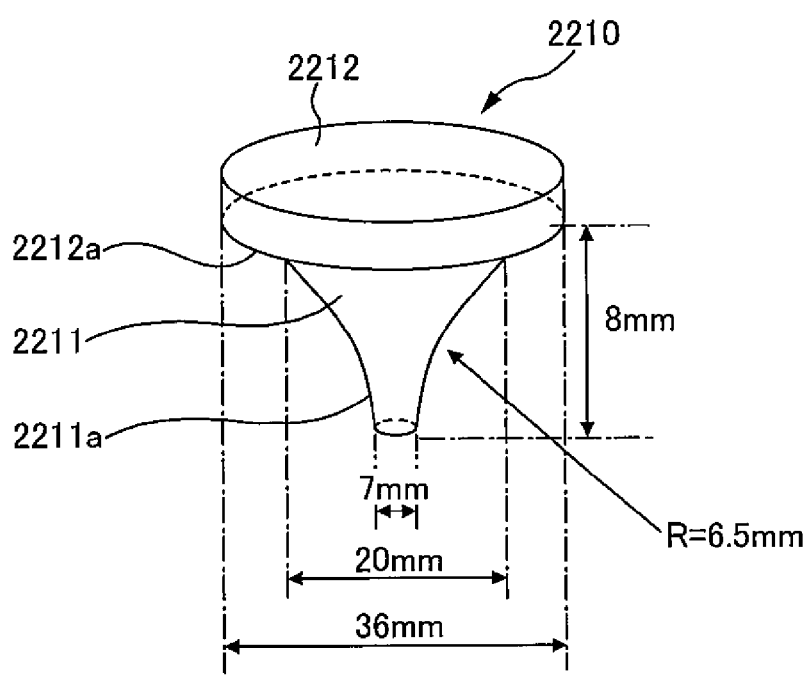
FIG. 24 is an external view of a pusher 2210.

The configuration of the pushers 2200 and 2210 will be described with reference to FIGS. 23 and 24. FIGS. 23 and 24 are external views of each of the pushers 2200 and 2210.

The plurality of pushers 2200 and 2210 has substantially the same shape. In detail, as shown in FIGS. 23 and 24, each of the plurality of pushers 2200 and 2210 is substantially funnel-shaped. Further in detail, each of the pushers 2200 and 2210 includes a tapered part 2201, 2211 that is provided at the leading-end part and that gradually thickens from the leading-end part towards the read-end part and a projected part 2202, 2212 that is provided at the rear-end and protrudes outside the outer edge of the rear-end of the tapered part 2201, 2211.

The tapered part 2201, 2211 is a part that has substantially a shape of a frustum of a cone. As shown in FIGS. 23 and 24, the leading-end part of the tapered part 2201, 2211 is a circular flat surface. The diameter of the leading-end of the tapered part 2201, 2211 is shorter than the external diameter of the outer cylinder 2040 (specifically, the external diameter of the major diameter part 2041). In the present embodiment, the diameter of the leading-end of the tapered part 2201 provided on the most upstream side pusher 2200 is approximately 5 mm and the diameter of the leading-end of the tapered part 2211 provided on the remaining pushers 2100 is approximately 7 mm. It is to be noted that the external diameter of the outer cylinder 2040 of the present embodiment is approximately 13.5 mm (see FIG. 25A).

The diameter of the rear end of the tapered part 2201, 2211 is greater than the external diameter of the outer cylinder 2040 (specifically, greater than the external diameter of the major diameter part 2041). In the present embodiment, the diameter of the rear end of the tapered part 2201 provided on the most upstream side pusher 2200 is approximately 18 mm and the diameter of the rear end of the tapered part 2211 provided on the remaining pushers 2100 is approximately 20 mm.

As for the tapered part 2201 provided on the most upstream side pusher 2200, a length from its leading-end to its rear end (in this embodiment, approximately 13 mm) is longer than a length from the leading-end to the rear end of the open petaloid part 2044 (in this embodiment, approximately 8.5 mm). It is to be noted that in this embodiment, a length from the leading-end to the rear end of the tapered part 2211 provided on the remaining pushers 2210 is approximately 8 mm.

Outer peripheral surfaces 2201a and 2211a of the tapered parts 2201 and 2202 are, as shown in FIGS. 23 and 24, curved surfaces that curves concavely and inwardly. In other words, a line of intersection between the outer peripheral surfaces 2201a and 2211a of the tapered parts 2211 and 2211 and a virtual plane lying through the central axis of the tapered parts 2211 and 2211 is an inwardly curved surface (see FIG. 22A). In the present embodiment, a radius of curvature R of the outer peripheral surface 2201a of the tapered part 2201 provided on the most upstream pusher 2200 is approximately 10 mm and the radius of curvature R of the outer peripheral surface 2211a of the tapered part 2211 provided on the remaining pushers 2210 is approximately 6.5 mm.

The projected parts 2202 and 2212 are disk-like parts. The projected parts 2202 and 2212 include projected surfaces 2202a, 2212a that are located at the leading-end of the projected parts 2202 and 2212 and project outside than the outer edge of the rear end of the tapered parts 2201 and 2211. The diameters of the projected parts 2202 and 2212 are greater than the external diameter of the outer cylinder 2040. In the present embodiment, the diameter of the projected part 2202 provided on the most upstream pusher 2200 is approximately 30 mm and the diameter of the projected parts 2212 of the remaining pushers 2210 are approximately 36 mm. It is to be noted that other dimensions are as shown in FIGS. 23 and 24.

Further, in the present embodiment, a part of the outer surface of each pusher 2200 and 2100 pressed against the inner wall surface of the petaloid part 2044 is subject to a surface finishing process so as to prevent damages on the inner wall surface. In detail, the surface finishing process is performed in such a manner that the center line average roughness Ra of the part pressed against the inner surface of the petaloid part 2044 is within a predetermined numerical range (preferably, Ra=3.2 to 6.3 and a maximum of Ra=12.5 to 25).

Using the pushers 2200 and 2210 described above, the first pusher unit 2151 is capable of performing the above-mentioned broadening process in a simple manner. Now, referring to FIGS. 25A to 25D, the broadening process by the first pusher unit 2151 will be described. FIGS. 25A to 25D are diagrams showing the broadening process. It is to be noted that FIGS. 25A to 25D illustrates a case in which the broadening process is performed using the most upstream pusher 2200 among the plurality of pushers 2200 and 2210.

As shown in FIG. 25A, when the outer cylinder 2040 comes to a position directly below one of the pushers 2200 and 2210 of the plurality of pushers 2200 and 2210, the first pusher unit 2151 moves the plurality of pushers 2200 and 2210 downwardly. At this time, the outer cylinder 2040 is in a state where its leading-end opening 2043 is facing substantially upwards. Thereby, the tapered parts 2201 and 2211 provided on the pushers 2200 and 2210 are inserted into the outer cylinder 2040 through the leading-end opening 2043. Then, the outer peripheral surfaces 2201a and 2211a of the tapered parts 2201 and 2211 come into contact with each of the inner wall surfaces of the plurality of petaloid parts 44. As a result, as shown in FIG. 25B, each of the petaloid parts 2044 bends in such a manner that it inclines outwardly in the radial direction of the outer cylinder 2040 along the outer surfaces 2201a and 2211a of the tapered parts 2201 and 2211.

As has been described above, the outer peripheral surfaces 2201a and 2211a of the tapered parts 2201 and 2211 are curved surfaces. Therefore, when the outer peripheral surfaces 2201a and 2211a of the tapered parts 2201 and 2211 come into contact with the inner wall surface of each of the plurality of petaloid parts 2044, each petaloid part will smoothly bend along the outer peripheral surfaces 2201a and 2211a of the tapered parts 2201 and 2211.

When the tapered parts 2201 and 2211 are further inserted into the outer cylinder 2040, as shown in FIG. 25C, the projected surfaces 2202a and 2212a of the projected parts 2202 and 2212 provided on the pushers 2200 and 2210 come into contact with the inner wall surface of each of the plurality of petaloid parts 2044. Thus, each of the plurality of the petaloid parts 2044 will bend until it bends substantially at right angles outwardly in the radial direction. At this time, as shown in FIG. 25C, the first pusher unit 2151 pushes down the projected surfaces 2202a and 2212a in such a manner that the projected surfaces 2202a and 2212a are at a position of about 5 mm downwards from the leading-end position of the outer cylinder 2040 before the broadening process (leading-end position of the petaloid part 2044).

Thereafter, as shown in FIG. 25D, the first pusher unit 2151 pulls out the pushers 2200 and 2210 from the outer cylinder 2040 by moving the pushers 2200 and 2210 upwardly. (In other words, separates the pushers 2200 and 2210 from each of the plurality of petaloid parts 2044.)

According to the above-described procedure, when the first pusher unit 2151 performs the broadening process to the outer cylinder 2040, the leading-end opening 2043 will be broadened as compared to the time before the broadening process. That is to say, in the present embodiment, the broadening process is performed that expands the leading-end opening 2043 by inserting the pushers 2200 and 2210 into the outer cylinder 2040 through the leading-end opening 2043, pressing the projected surfaces 2202a and 2212a of the projected parts 2202 and 2212 of the pushers 2200 and 2210 to each of the plurality of the petaloid parts 2044, and bending each of the petaloid outwardly in the radial direction of the outer cylinder 2040.

After the above-mentioned broadening process, the outer cylinder 2040 is kept in a bent shape (specifically, the rear end of each of the petaloid parts 2044 is kept in a bent shape). In detail, as shown in FIG. 25D, after the broadening process, each of the plurality of petaloid parts 2044 are in an outwardly bent state in the radial direction of the outer cylinder 2040. It is to be noted that the angle of inclination of the petaloid part 2044 (angle θ in FIG. 25D) may be greater than or equal to one degree.

It is to be noted that if the petaloid part 2044 inclines outwardly in the radial direction with an angle of 45 degrees or more, it will be disadvantageous for the leading-end process that processes the leading-end part of the outer cylinder 2040 into a substantially hemispherical form. Further, if the petaloid part 2044 is bent too much, it might damage the outer cylinder 2040. Therefore, in the present embodiment, the above-mentioned bent shape is formed in such a manner that each of the plurality of the petaloid parts 2044 is inclined at an angle of inclination between one degree and 45 degrees outwardly in the radial direction. In other words, according to the broadening process of the present embodiment, directly after separating the pushers 2200 and 2210 from each of the plurality of petaloid parts 2044, the pushers 2200 and 2210 are pressed against the each petaloid part 2044 in such a manner that the each petaloid part 2044 is inclined at an angle of inclination between one degree and 45 degrees outwardly in the radial direction.

In the present embodiment, the first pusher unit 2151 performs the broadening process on the outer cylinder 2040 that is mounted on the mount 2160. As has been described above, the outer cylinder 2040 mounted on the mount 2160 is in a state where each of the plurality of the petaloid part 2044 is exposed from the leading-end of the petaloid part 2044 to the rear end of the petaloid part 2044. Therefore, it facilitates the pressing of the pushers 2200 and 2210 against the inner wall surface of each of the petaloid parts 2044 and the bending of the each petaloid part 2044 outwardly in the radial direction. Further, since the pushers 2200 and 2210 are pressed against the inner wall surface of each of the plurality of the petaloid parts 2044 with the outer cylinder 2040 being mounted on the mount 2160, a pressure force exerted on each petaloid part 2044 is substantially even between the petaloid parts 2044.

The first pusher unit 2151 includes the plurality of pusher units 2200 and 2210 and performs the broadening process on the outer cylinder 2040, every time the outer cylinder 2040 is positioned directly below each of the pushers 2200 and 2210. That is to say, in this embodiment, the broadening process is performed a plurality of times (in this embodiment, four times) on the outer cylinder 2040 before inserting the first inner cylinder 2051 into the outer cylinder 2040. Thus, with the leading-end opening 2043 being securely expanded, every item such as the first inner cylinder 2051 can be inserted into the outer cylinder 2040 through the leading-end opening 2043.

Further, the first pusher unit 2151 of the present embodiment includes, in addition to the plurality of pushers 2200 and 2210, other pushers (hereinafter, referred to as an auxiliary pusher 2230) having a shape different from the plurality of the pushers 2200 and 2210. Before performing the broadening process using each of the plurality of pushers 2200 and 2210, the first pusher unit 2151 performs an auxiliary process on the outer cylinder 2040 using the auxiliary pusher 2230. The auxiliary process is a process broadens the leading-end opening 2043 of the outer cylinder 2040 by inserting the auxiliary pusher 2230 into the outer cylinder 2040 through the leading-end opening 2043 of the outer cylinder 2040, pressing the auxiliary pusher 2230 against the inner wall surface of each of the plurality of the petaloid parts 2044 and bending outwardly in the radial direction each of the plurality of petaloid parts 2044. The auxiliary process corresponds to the other broadening process. Hereinafter, the auxiliary pusher 2230 will be described.

Figure 26:
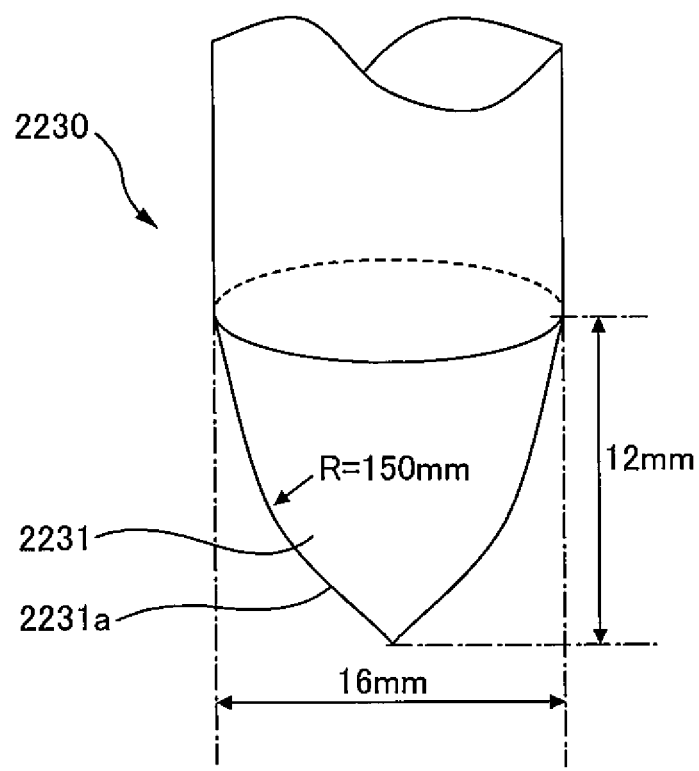
FIG. 26 is an external view of an auxiliary pusher 2230.

The auxiliary pusher 2230 is an example of the other jig and is made of a resin material such as plastics. Similarly to the plurality of pushers 2200 and 2210, the auxiliary pusher 2230 is attached to the attachment plate 2220. As shown in FIG. 22A, the auxiliary pusher 2230 is placed at a position upstream of the most upstream pusher 2200 in the transport direction. Further, as shown in FIG. 26, the auxiliary pusher 2230 includes other tapered part 2231 at the leading-end side of the auxiliary pusher 2230 that thickens from the leading-end towards the rear end. FIG. 26 is an external view of the auxiliary pusher 2230.

The other tapered part 2231 is a part that has substantially conical and has a leading-end that is more pointed than the leading-end of the tapered parts 2201 and 2211 provided on the pushers 2200 and 2210. As shown in FIG. 26, in the present embodiment, the length between the leading-end to the rear end of the other tapered part 2231 is approximately 12 mm and the diameter of the rear end of the other tapered part 2231 is approximately 16 mm.

When the outer cylinder 2040 comes to a position directly below the auxiliary pusher 2230, the first pusher unit 2151 having the auxiliary pusher 2230 of the above configuration moves the auxiliary pusher 2230 downwards. Thus, the other tapered part 2231 that is provided on the auxiliary pusher 2230 is inserted into the outer cylinder 2040 through the leading-end opening 2043 of the outer cylinder 2040. When the other tapered part 2231 is inserted into the outer cylinder 2040, an outer peripheral surface 2231a of the other tapered part 2231 comes into contact with the inner wall surface of each of the plurality of petaloid parts 2044. Thus, each of the plurality of the petaloid parts 2044 bends along the outer peripheral surface 2231a of the other tapered part 2231 in the radial direction of the outer cylinder 2040 and thus the leading-end opening 2043 is expanded.

As has been described above, the auxiliary process is a process that inserts the other tapered part 2231 provided on the auxiliary pusher 2230 into the outer cylinders 2040 through the leading-end opening 2043, presses the outer peripheral surface 2231a of the other tapered part 2231 against each of the plurality of petaloid parts 2044 and expands the leading-end openings 2043 by outwardly bending each of the petaloid parts 2044 in the radial direction. The first pusher unit 2151 performs the above-mentioned auxiliary process on the outer cylinder 2040 before performing the broadening process. The reason for performing the auxiliary process before the broadening process will be described below.

As has been described above, the leading-ends of the tapered parts 2201 and 2211 provided on the pushers 2200 and 2210 of the present embodiment are flat surfaces. On the other hand, there are some cases where the outer cylinder 2040 has petaloid parts 2044 that are slightly inclining inwards at a step before performing the broadening process. If the tapered parts 2201 and 2211 of the pushers 2200 and 2210 are inserted into the outer cylinder 2040 whose petaloid parts 2044 are inclined inwards, the leading-ends of the tapered parts 2201 and 2211 might get caught at the petaloid parts 2044. As a result, the petaloid parts 2044 will be rolled inward and it becomes difficult to insert the inner cylinder 2050 and the tampon main body 2020 into the outer cylinder 2040. That is to say, when the broadening process of the present embodiment is performed on the outer cylinder 2040 whose petaloid parts 2044 are inclined inwards, it will be even more difficult to insert each item into the outer cylinder 2040.

In contrast, the leading-end of the other tapered part 2231 of the auxiliary pusher 2230 is more pointed than the leading-end of the tapered parts 2201 and 2211 of the pushers 2200 and 2210. Therefore, even if the auxiliary pusher 2230 is inserted into the outer cylinder 2040 whose petaloid parts 2044 are inclined inwards, the leading-end of the auxiliary pusher 2230 will not catch the petaloid parts 2044 inward and roll the petaloid part 2044 inwards.

When the other tapered part 2231 of the auxiliary pusher 2230 is inserted into the outer cylinder 2040 and the outer peripheral surface 2231a of the other tapered part 2231 is pressed against the inner wall surface of the petaloid parts 2044 inclined inwards, the petaloid parts 2044 will open by bending outwards in the radial direction of the outer cylinder 2040. That is to say, by performing the auxiliary process prior to the broadening process, it will be possible to keep the petaloid parts 2044 open in such a manner that the leading-ends of the tapered parts 2201 and 2211 of the pushers 2200 and 2210 do not catch the petaloid parts 2044 while performing the broadening process. As a result, the first pusher unit 2151 can properly perform the broadening process later on the outer cylinder 2040.

The second pusher unit 2152 performs a broadening process on the outer cylinder 2040 from the time at which the first inner cylinder 2051 is inserted into the outer cylinder 2040 until the time at which the second inner cylinder 2052 is inserted into the outer cylinder 2040. The second pusher unit 2152 is located between the first inner cylinder inserting mechanism 2131 and the second inner cylinder inserting mechanism 2132 in the transport direction. The third pusher unit 2153 performs a broadening process on the outer cylinder 2040 from the time at which the second inner cylinder 2052 is inserted into the outer cylinder 2040 until the time at which the tampon main body 2020 is inserted into the outer cylinder 2040. The third pusher unit 2153 is located between the second inner cylinder inserting mechanism 2132 and the tampon main body inserting mechanism 2140 in the transport direction.

Figure 22B:
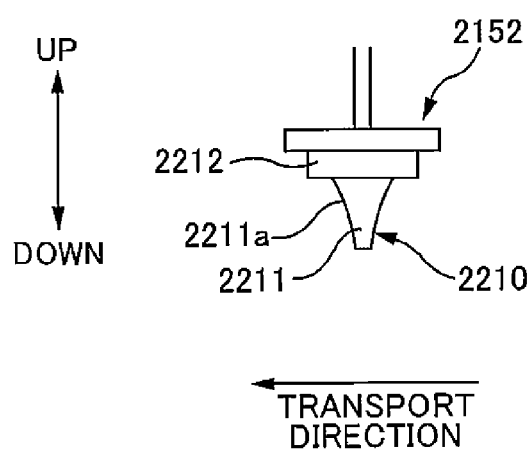
FIG. 22B is a diagram showing a second pusher unit 2152.

As shown in FIG. 22B, the second pusher unit 2152 and the third pusher unit 2153 are of substantially similar structure as the first pusher unit 2151 except that the number of pushers 2210 provided is different. FIG. 22B is a diagram showing the second pusher unit 2152. It is to be noted that the third pusher unit 2153 is not indicated in the drawings since it has the same structure as the second pusher unit 2152.

As shown in FIG. 22B, each unit of the second pusher unit 2152 and the third pusher unit 2153 includes a pusher 2210 which is an example of the jig that performs the broadening process. This pusher 2210 is the same as the pusher 2210 that is located on the downstream side of the most upstream pusher 2200, among the plurality of pushers 2200 and 2210 provided on the first pusher unit 2151. That is to say, the broadening process can also be performed using a simple method on the second pusher unit 2152 and the third pusher unit 2153.

The second pusher unit 2152 and the third pusher unit 2153 perform the broadening process with the substantially similar procedure as the broadening process performed by the first pusher unit 2151. The second pusher unit 2152 performs the broadening process once on the outer cylinder 2040 from the time at which the first inner cylinder 2051 is inserted into the outer cylinder 2040 until the time at which the second inner cylinder 2052 is inserted into the outer cylinder 2040. The third pusher unit 2153 performs the broadening process once on the outer cylinder 2040 from the time at which the second inner cylinder 2052 is inserted into the outer cylinder 2040 until the time at which the tampon main body 2020 is inserted into the outer cylinder 2040.

It is to be noted that the second pusher unit 2152 and the third pusher unit 2153 do not perform the above-mentioned auxiliary process before performing the broadening process. (In other words, it does not include the auxiliary pusher 2230.) This is because, at the step of performing the broadening process, each of the second pusher unit 2152 and the third pusher unit 2153 are at least inclined outwards in the radial direction and therefore it is not necessary to perform the auxiliary process again.

As has been described above, the broadening mechanism 2150 of the present embodiment performs the broadening process on the outer cylinder 2040 each time at a step before inserting each of the first pusher unit 2151, the second pusher unit 2152 and the tampon main body 2020 into the outer cylinder 2040. However, it is not limited to this and it is sufficient if the broadening process is performed at least from the time at which the outer cylinder 2040 is mounted on the mount 2160 until the time at which the inner cylinder 2050 (in this embodiment, the first inner cylinder 2051) is inserted into the outer cylinder 2040.

It is to be noted that in this embodiment, the broadening mechanism 2150 performs the broadening process on the outer cylinder 2040 in a state where the temperature of the pushers 2200 and 2210 is maintained at a temperature that is 50° C. below the melting point of the thermoplastic resin forming the outer cylinder 2040. That is to say, the leading-end opening 2043 is not pushed and expanded by heating and softening the outer cylinder 2040 as in the case of heat forming but the leading-end opening 2043 is pushed and expanded only with the pressure force applied by the pushers 2200 and 2210. Therefore, in the present embodiment, each of the petaloid parts 2044 will not be deformed by heat as in the case of heat forming. The temperature of the pusher 2210 may be within a range between the glass transition point of the thermoplastic resin and the temperature that is 50° C. below the melting point of the thermoplastic resin forming the outer cylinder 2040 and is preferably room temperature.

<Assembling Procedure of Tampon 2010>

Figure 27:
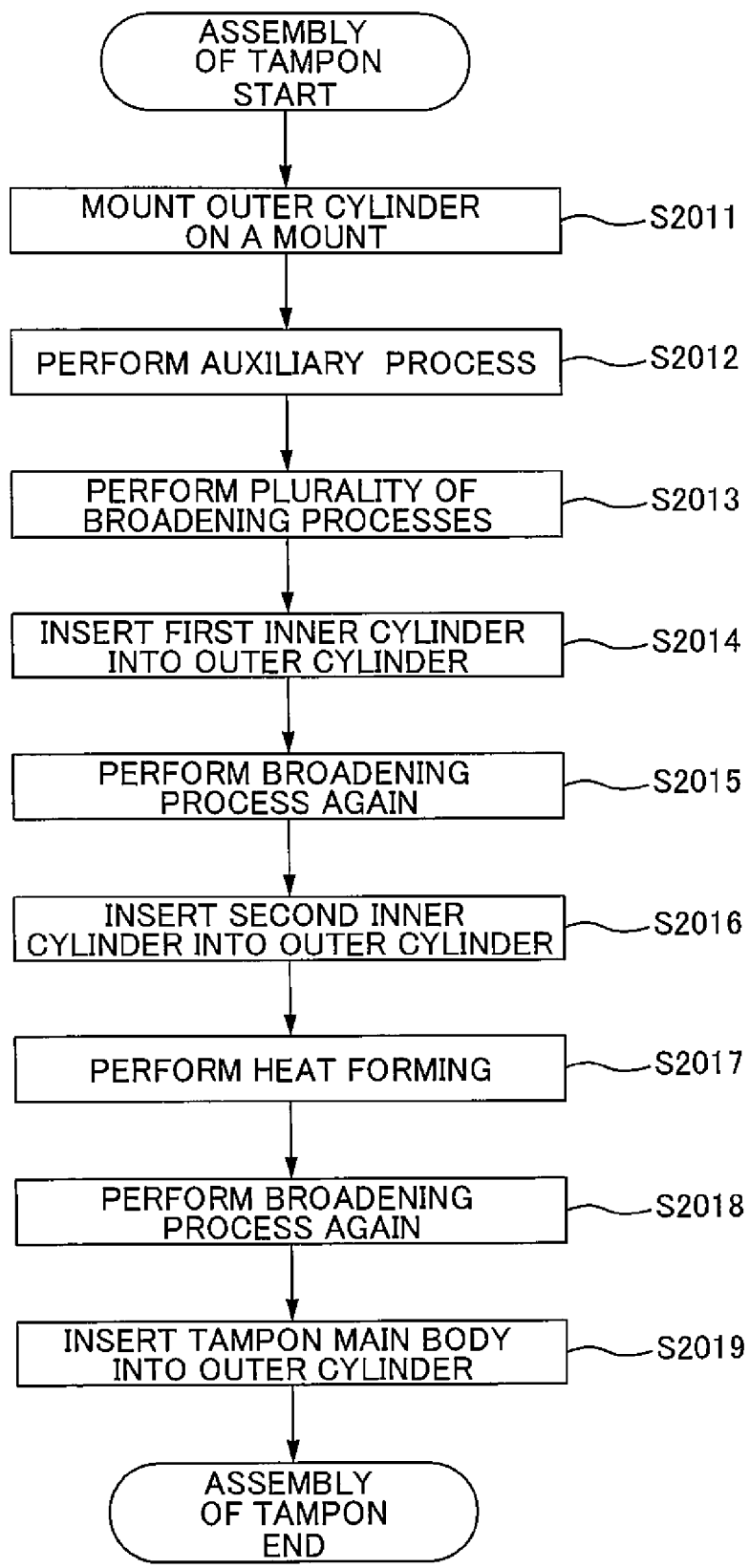
FIG. 27 is a flowchart showing the assembling of the tampon 2010.

Next, the assembling procedure of the tampon 2010 by the assembling apparatus 2100 will be described with reference to FIG. 27. FIG. 27 is a flowchart showing the assembling of the tampon 2010.

As shown in FIG. 27, the assembling of the tampon 2010 starts with a step of mounting, by the outer cylinder supplying mechanism 2120, the outer cylinder 2040 on the mount 2160 placed on the transport conveyor 2110 (S2011). The transport conveyor 2110 intermittently carries out motions of transporting the mount 2160 each time with a predetermined distance. On the other hand, the outer cylinder supplying mechanism 2120 is synchronized with the transport conveyor 2110 and mounts the outer cylinder 2040 on the mount 2160 between the transport motions (while the mount 2160 is at rest). In the present embodiment, as has been described above, the outer cylinder 2040 is mounted on the mount 2160 in such a manner that each of the plurality of the petaloid parts 2044 is exposed from the leading-end of the petaloid part 2044 to the rear end of the petaloid part 2044.

Thereafter, by repeating the transport motions intermittently, the outer cylinder 2040 mounted on the mount 2160 is transported together with the mount 2160 to the downstream side in the transport direction. Then, at the time when the outer cylinder 2040 is located directly below the auxiliary pusher 2230 in the transport direction, the auxiliary process is performed on the outer cylinder 2040 mounted on the mount 2160 by the broadening mechanism 2150 (specifically, the first pusher unit 2151) (S2012). The broadening mechanism 2150 is synchronized with the transport conveyor 2110 and performs the auxiliary process on the outer cylinder 2040 while the outer cylinder 2040 is at rest at a position directly below the auxiliary pusher 2230.

After performing the auxiliary process, when the transport operation is performed once, the outer cylinder 2040 will be positioned directly under the most upstream side pusher 2200, which is among the plurality of pushers 2200 and 2210 provided at the most upstream side. When the outer cylinder 2040 is at rest at such a position, the broadening mechanism 2150 (specifically, the first pusher unit 2151) performs the broadening process on the outer cylinder 2040 (the outer cylinder 2040 mounted on the mount 2160) (S2013).

In the present embodiment, as has been described above, in the broadening process, the projected surface 2202a of the projected part 2202 of the most upstream-side pushers 2200 is pressed against the inner wall surface of each of the plurality of the petaloid parts 2044. As a result, each of the plurality of the petaloid parts 2044 will be bent substantially at right angles outwardly in the radial direction of the outer cylinder 2040. At the time when the most upstream-side pusher 2200 is pulled out of the outer cylinder 2040 (separate from each of the plurality of petaloid parts 2044), the first broadening process terminates. Directly after the first broadening process, the outer cylinder 2040 is kept bent and each of the plurality of petaloid parts 2044 is in a state where it is inclined outwardly in the radial direction at an angle of inclination between 1 degree and 45 degrees.

After the first broadening process, when the transport operation is performed once, the outer cylinder 2040 comes to a position directly under the pusher 2210 that is adjacent to the most upstream-side pusher 2200 (in other words, the second pusher 2210). At this position, when the outer cylinder 2040 is at rest, a second broadening process is performed on the outer cylinder 2040. Thereafter, the transport operation and the broadening process are repeated in turns and four broadening processes are performed. As the number of implementation of the broadening process increases, the angle of inclination of the petaloid part 2044 directly after the broadening process will gradually increase. It is to be noted that, directly after the fourth broadening process, the angle of inclination of the petaloid part 2044 is between 1 degree and 45 degrees.

After having performed the broadening process on the outer cylinder 2040 for a plurality of times, the transport motion is repeated and the outer cylinder 2040 on which the broadening process is performed is transported towards the downstream side in the transport direction with the mount 2160. Then, when the outer cylinder 2040 is located at a position below the first inner cylinder inserting mechanism 2131, the first inner cylinder 2051 is inserted into the outer cylinder 2040 through the leading-end opening 2043 by the first inner cylinder inserting mechanism 2131 (S2014). That is to say, in the present embodiment, after transporting the outer cylinder 2040 subjected to the broadening process is transported together with the mount 2160 by the transport conveyor 2110 to the downstream side in the transport direction, the first inner cylinder 2051 is inserted into the outer cylinder 2040. The first inner cylinder inserting mechanism 2131 synchronizes with the transport conveyor 2110 and the first inner cylinder inserting mechanism 2131 inserts the first inner cylinder 2051 into the outer cylinder 2040 while the outer cylinder 2040 is at rest below the first inner cylinder inserting mechanism 2131.

After inserting the first inner cylinder 2051 into the outer cylinder 2040, the transport motion is repeated. Then, while the outer cylinder 2040 is located directly below the pusher 2210 of the second pusher unit 2152 and the outer cylinder 2040 is at rest at that position, the broadening process is performed again on the outer cylinder 2040 (S2015). It is to be noted that, directly after the broadening process, the angle of inclination of the petaloid part 2044 is in a range from 1 degree to 45 degrees.

Thereafter, the transport motion is repeated and the second inner cylinder 2052 is inserted into the outer cylinder 2040 through the leading-end opening 2043 by the second inner cylinder inserting mechanism 2132, while the outer cylinder 2040 is located at a position below the second inner cylinder inserting mechanism 2132 and is at rest at such a position (S2016). That is to say, the outer cylinder 2040 on which the broadening process was performed again after insertion of the first inner cylinder 2051 is transported together with the mount 2160 to the downstream side in the transport direction by the transport conveyor 2110 and then the second inner cylinder 2052 is inserted into the outer cylinder 2040.

After inserting the second inner cylinder 2052 into the outer cylinder 2040, the transport motion is repeated. Then, at the time when the outer cylinder 2040 (the first inner cylinder 2051 and the second inner cylinder 2052) has reached in the transport direction at a position where a heat forming part (not shown) is provided, heat forming is performed that forms the flared part 2052c at the rear-end part of the second inner cylinder 2052 (S2017). When the heat forming is terminated, the assembling of the applicator 2030 is complete.

After performing the heat forming, the transport motion is further repeated. Then, while the outer cylinder 2040 (in other words, the assembled applicator 2030) is located at the position directly below the pusher 2210 of the third pusher unit 2153 and the outer cylinder 2040 is at rest at such a position, the broadening process is performed on the outer cylinder 2040 once more (S2018). It is to be noted that, directly after the broadening process, the angle of inclination of the petaloid part 2044 is in a range between 1 degree and 45 degrees.

Then, the transport operation is repeated and, when the outer cylinder 2040 (in other words, the assembled applicator 2030) is located at a position below the tampon main body inserting mechanism 2140, the tampon main body 2020 is inserted into the outer cylinder 2040 through the leading-end opening 2043 by the tampon main body inserting mechanism 2140 (S2019). That is to say, the outer cylinder 2040 subjected to the broadening process again after insertion of the inner cylinder 2050 (the first inner cylinder 2051 and the second inner cylinder 2052) is transported together with the mount 2160 to the downstream side in the transport direction by the transport conveyor 2110, and then the tampon main body 2020 is inserted into the outer cylinder 2040. It is to be noted that the tampon main body inserting mechanism 2140 is also synchronized with the transport conveyor 2110 and, while the outer cylinder 2040 is at rest with the leading-end opening 2043 opposing the rear-end opening of the guide tube 2141, inserts the tampon main body 2020 held in the guide tube 2141 into the outer cylinder 2040 through the leading-end opening 2043.

According the above-described series of steps, the assembling of the tampon 2010 is completed. The assembled tampon 2010 is transported together with the mount 2160, while being mounted on the mount, towards the step of processing the leading-end of the outer cylinder 2040 into a substantially hemispherical shape.

As has been described above, the manufacturing method of the tampon 2010 of the present embodiment includes mounting the outer cylinder 2040 on the mount 2160 (S2011), broadening the outer cylinder 2040 (S2013, S2015 and S2018), inserting the inner cylinder 2050 into the outer cylinder 2040 through the leading-end opening 2043 after performing the broadening process (S2014 and S2016), and inserting the tampon main body 2020 into the outer cylinder 2040 through the leading-end opening 2043 after performing the broadening process (S2019). Further, the broadening includes performing broadening process a plurality of times to the outer cylinder 2040 before inserting the first inner cylinder 2051 to the outer cylinder 2040 (S2013), performing a broadening process again to the outer cylinder 2040 during the time between insertion of the first inner cylinder 2051 into the outer cylinder 2040 and insertion of the inner cylinder 2050 into the outer cylinder 2040 (S2015) and performing a broadening process again on the outer cylinder 2040 during the time between insertion of the second inner cylinder 2052 into the outer cylinder 2040 and the insertion of the tampon main body 2020 into the outer cylinder 2040 (S2018).

—Effectiveness of Manufacturing Method of the Tampon 2010 of the Present Embodiment—

According to the manufacturing method of a tampon of the present embodiment, a broadening process is performed on the outer cylinder 2040 in which each of the plurality of the petaloid parts 2044 surrounding the leading-end opening 2043 of the outer cylinder 2040 is bent outwardly in the radial direction of the outer cylinder 2040 to broaden the leading-end opening 2043. Then, after performing the broadening process, the inner cylinder 2050 (specifically, the first inner cylinder 2051 and the second inner cylinder 2052) and the tampon main body 2020 are inserted into the outer cylinder 2040 through the leading-end opening 2043. Thus, the inner cylinder 2050 and the tampon main body 2020 can be smoothly inserted into the outer cylinder 2040. Hereinafter, the effectiveness of the manufacturing method of the tampon 2010 of the present embodiment will be described in detail.

When manufacturing the tampon 2010 of the present embodiment, since each of the outer cylinder 2040, the inner cylinder 2050 and the tampon main body 2020 has the above-mentioned shape, the inner cylinder 2050 and the tampon main body 2020 will be inserted into the outer cylinder 2040 through the leading-end opening 2043. That is to say, the leading-end opening 2043 serves as an insert inlet when inserting the inner cylinder 2050 and the tampon main body 2020 into the outer cylinder 2040. As has been described above in the "Problem To Be Solved By The Invention," in order to improve the production speed of the tampon 2010, it is necessary to insert the inner cylinder 2050 and the tampon 2010 into the outer cylinder 2040 through the leading-end opening 2043 smoothly.

Now, there are cases where the petaloid parts 2044 incline inwardly in the radial direction during the period from injection molding of the outer cylinder 2040 to the mounting on the mount 2160, due to a collision between outer cylinder 2040, etc. When the petaloid parts 2044 incline inwardly in the radial direction, the leading-end opening 2043 becomes smaller and therefore it will be difficult to insert the inner cylinder 2050 and the tampon main body 2020 into the outer cylinder 2040 through the leading-end opening 2043. Also, if the inner cylinder 2050 and the tampon main body 2020 are forced to be inserted into the outer cylinder 2040 under such a condition, the petaloid parts 2044 will be rolled into the outer cylinder 2040 and thus a defective tampon 2010 will be manufactured.

Particularly, like the tampon 2010 of the present embodiment, in cases where the difference between the external diameter of the inner cylinder 2050 and the internal diameter (specifically, the difference between the external diameter of the flange part 2051a of the tampon main body 2020 and the internal diameter of the major diameter part 2041) and the difference between the diameter of the tampon main body 2020 and the inner diameter of the outer cylinder 2040 are both very small, it becomes even more difficult to insert the inner cylinder 2050 and the tampon main body 2020 into the outer cylinder 2040 through the leading-end opening 2043 in a state where the leading-end opening 2043 has become small.

Therefore, in order to prepare for a case where the petaloid parts 2044 have inclined inwards, it is necessary to have some measures to facilitate the insertion of the inner cylinder 2050 and the tampon main body 2020 into the outer cylinder 2040. Such measures may be, for example, making the external diameter of the inner cylinder 2050 and the diameter of the tampon main body smaller with respect to the inner diameter of the outer cylinder 2040. With such a measure, insertion of the inner cylinder 2050 and the tampon main body 2020 into the tampon main body 2020 can be facilitated. However, the outer cylinder 2040 and the inner cylinder 2050 (or the outer cylinder 2040 and the tampon main body 2020) will not fit well and may cause a problem when using the tampon 2010.

On the other hand, in the present embodiment, the above-mentioned broadening process is performed on the outer cylinder 2040 before inserting the inner cylinder 2050 and tampon main body 2020 into the outer cylinder 2040. Thus, the inner cylinder 2050 and the tampon main body 2020 can be inserted into the outer cylinder 2040 through the leading-end opening 2043 with the leading-end opening 2043 being broadened. As a result, the inner cylinder 2050 and the tampon main body 2020 can be smoothly inserted into the outer cylinder 2040 without changing the external diameter of the inner cylinder 2050 or the diameter of the tampon main body 2020. Also, since each of the plurality of petaloid parts 2044 are bent outwardly in the radial direction of the outer cylinder 2040, the above-mentioned problem, that is to say, the rolling-in of the petaloid part 2044 into the outer cylinder 2040, can be prevented. Thereby, the tampon 2010 can be assembled properly.

As has been described above, by performing the broadening process on the outer cylinder 2040 before inserting the inner cylinder 2050 and the tampon main body 2020 into the outer cylinder 2040, the inner cylinder 2050 and the tampon main body 2020 can be smoothly inserted into the outer cylinder 2040 and the tampon 2010 can be assembled properly. Therefore, according to the manufacturing method of the tampon 2010 of the present embodiment, the production speed of the tampon 2010 can be improved.

Further, in the present embodiment, the broadening process is performed on the outer cylinder 2040 after mounting the outer cylinder 2040 on the mount 2160. That is to say, the broadening is a process in which broadening is performed on the outer cylinder 2040 after mounting the outer cylinder 2040 onto the mounting cylinder. This is because it is highly possible that the petaloid parts 2044 incline inwardly during the period from the injection molding of the outer cylinder 2040 to its mounting on the mount 2160 (specifically, during a period from the mounting onto the vibratory table 2121 of the outer cylinder transport feeder 2121 to the supplying to the transport conveyor 2110). Therefore, if the broadening process is performed on the outer cylinder 2040 after mounting the outer cylinder 2040 on the mount 2160, the broadening process will be performed effectively. The outer cylinder 2040 subjected to the broadening process is transported by the transport conveyor 2110 to the downstream side in the transport direction together with the mount 2160 and then the inner cylinder 2050 (the first inner cylinder 2051 and the second inner cylinder 2052) is inserted into the outer cylinder 2040. Thereafter, the outer cylinder 2040 in which the inner cylinder 2050 is inserted is transported by the transport conveyor 2110 to the downstream side in the transport direction together with the mount 2160 and then the tampon main body 2020 is inserted into the outer cylinder 2040. Thus, it becomes easier to keep the leading-end opening 2043 in an open state until the inner cylinder 2050 and the tampon main body 2020 are inserted into the outer cylinder 2040.

The present embodiment has been described with reference to an example in which the outer cylinder 2040 is kept mounted on the same mount 2160 during the period from the mounting of the outer cylinder 2040 onto the mount 2160 to the completion of the assembly of the tampon 2010 (see FIG. 20), however, it is not limited to such an example. For example, with a structure in which a single outer cylinder 2040 is transported by a plurality of transport conveyors 2110, when the single outer cylinder 2040 is passed from one transport conveyors 2110 to the other transport conveyor 2110, the mount 2160 on which the outer cylinder 2040 is mounted is switched over. That is to say, there may be a case where the outer cylinder 2040 mounted on the mount 2160 should be mounted again on another mount 2160. Even in such a case, by performing the broadening process on the outer cylinder 2040 after the outer cylinder 2040 is mounted on the mount 2160 on which the outer cylinder 2040 is mounted at first (in other words, the mount 2160 that receives the mount 2160 from the outer cylinder supplying mechanism 2120), the broadening process can be performed efficiently.

Also, in the present embodiment, prior to inserting each of the second inner cylinder 2052 and the tampon main body 2020 into the outer cylinder 2040, the broadening process is performed each time on the outer cylinder 2040 (S2013, S2015 and S2018 in FIG. 27). Thereby, when inserting each of the first inner cylinder 2051, the second inner cylinder 2052 and the tampon main body 2020 into the outer cylinder 2040, the leading-end opening 2043 can be broadened more securely.

—Other Embodiments—

The foregoing embodiments are merely for the purpose of elucidating the manufacturing method and manufacturing apparatus (assembling apparatus) of the tampon 2010 of the present invention and are not to be interpreted as limiting the invention. The invention can of course be altered and improved without departing from the gist thereof and equivalents are intended to be embraced therein. Also, the above-mentioned setting values, sizes and configurations, etc., are merely an example provided to show the effect of the present invention and is not to be interpreted as limiting the invention.

In the above-mentioned embodiment, the tampon 2010 having the inner cylinder 2050 of a two-tier structure as a pushing member has been described, but the present invention is not limited thereto. For example, it can be a tampon 2010 having the inner cylinder 2050 with a fixed length (which does not extend or contract).

Also, in the above-mentioned embodiment, the outer cylinder 2040 is mounted on the mount 2160 with the leading-end opening 2043 facing substantially directly upwards. That is to say, the above-mentioned embodiment has a structure that inserts the inner cylinder 2050 (the first inner cylinder 2051 and the second inner cylinder 2052) and the tampon main body 2020 into the outer cylinder 2040 from above. However, it is not limited to such structure and can be a structure, for example, in which the outer cylinder 2040 is placed on the transport conveyor 2110 in a state where the leading-end opening 2043 is facing substantially directly laterally and the inner cylinder 2050 and the tampon main body 2020 can be inserted into the outer cylinder 2040 from the side. With such a structure, in order to perform the broadening process on the outer cylinder 2040, the pushers 2200 and 2210 can be inserted into the outer cylinder 2040 from the side and pressed against each of the plurality of the petaloid part 2044 from the side.

Also, in the above-mentioned embodiment, although the inner cylinder 2050 and the tampon main body 2020 are separately inserted into the outer cylinder 2040, it is not limited to such a structure. For example, it may be a structure in which the tampon main body 2020 is accommodated in the outer cylinder 2040 in a state it is inserted in the inner cylinder 2050. When manufacturing the tampon 2010 of such a structure, after inserting the tampon main body 2020 into the inner cylinder 2050, the inner cylinder 2050 in which the tampon main body 2020 is inserted may be inserted into the outer cylinder 2040 (That is to say, the tampon main body 2020 and the inner cylinder 2050 may be inserted into the outer cylinder 2040 at the same time).

Figure 28:
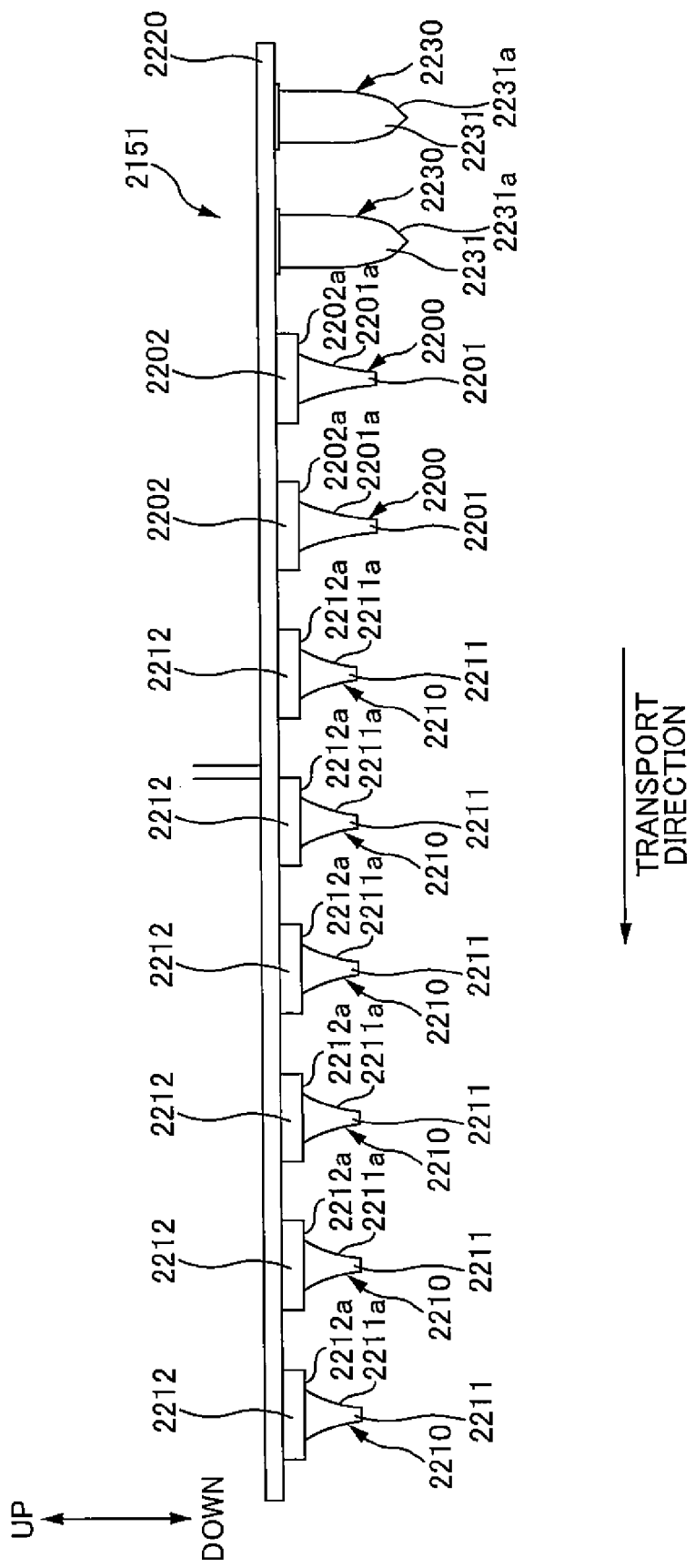
FIG. 28 is a diagram showing the structure for simultaneously performing the broadening process on a plurality of outer cylinders 2040.

Also, in the above-mentioned embodiment, a structure in which the broadening process is performed to the outer cylinder 2040 one by one. However, the present invention is not limited to such a structure and may be a structure in which the broadening process is performed on a plurality of outer cylinders 2040 at the same time. For example, as shown in FIG. 28, if a plurality of pushers 2200 and 2210 having mutually the same configuration are attached to the attachment plate 2220 in a group, the broadening process can be performed simultaneously on the plurality of outer cylinders 2040 (in the structure shown in FIG. 28, two outer cylinders 2040). FIG. 28 is a diagram showing the structure for simultaneously performing the broadening process on a plurality of outer cylinders 2040 and is a diagram corresponding to FIG. 22A.

(Part Three)

An apparatus for manufacturing a tampon, the tampon including an absorbent body that absorbs liquid, an accommodating member that is cylindrical and accommodates the absorbent body, and a pushing member that moves inside the accommodating member and pushes the absorbent body out of the accommodating member, the accommodating member including a minor diameter part provided at a one-end part thereof and a major diameter part provided at an other-end part thereof, the major diameter part having an external diameter greater than that of the minor diameter part, is provided, the apparatus including:

an orienting mechanism that orients the accommodating member;

a first inserting mechanism that inserts the pushing member into the accommodating member oriented by the orienting mechanism; and a second inserting mechanism that inserts the absorbent body into the accommodating member in which the pushing member is inserted, the orienting mechanism including:

an opening through which the accommodating member is inputted;

a pair of first protruded parts located on one-end side in a longitudinal direction of the opening and protruding inwardly in an opposing manner into the opening; and a pair of second protruded parts located on other-end side in the longitudinal direction of the opening and protruding inwardly in an opposing manner into the opening, a gap between the pair of first protruded parts being greater than the external diameter of the minor diameter part and smaller than the external diameter of the major diameter part, and a gap between the pair of second protruded parts being greater than the external diameter of the minor diameter part and smaller than the external diameter of the major diameter part.

With such an apparatus of manufacturing a tampon, since the accommodating cylinder received by the receiving part when there is the accommodating cylinder in the receiving part is discharged out of the second transport path, the accommodating cylinders can be prevented from being piled up before the receiving part. Thereby, the accommodating cylinders are prevented from being joined to each other and thus the accommodating cylinder can be supplied properly.

In the above apparatus for manufacturing a tampon, the supplying mechanism may include:

a parts feeder having a placing table and moves the accommodating cylinder placed on the placing table towards the first transport path; and a third transport path that transports the accommodating cylinder that is discharged out of the second transport path through the outlet to the placing table. With the above apparatus for manufacturing a tampon, the accommodating cylinder that is discharged out of the second transport can be transported again to the second transport path.

In the above apparatus for manufacturing a tampon, each of the first transport path and the third transport path is inclined in such a manner that the accommodating cylinder slides down on each of the first transport path and the third transport path;

the receiving part is a recess between the first transport path and the third transport path;

the recess receives the accommodating cylinder which has slid down the first transport path when there is no accommodating cylinder in the recess and receives the accommodating cylinder which has slid down the first transport path when there is the accommodating cylinder in the recess in such a manner that it is piled on top of the accommodating cylinder in the recess; and the side wall discharges the accommodating cylinder piled on top of the accommodating cylinder in the recess out of the second transport path through the outlet.

With such an apparatus for manufacturing a tampon, the accommodating cylinder can be discharged out of the second transport path by making use of the momentum acquired by the accommodating cylinder sliding down on the first transport path.

In the above apparatus for manufacturing a tampon, the outlet may be a cutaway part formed in the side wall;

the side wall includes a retaining part provided below the cutaway part, the retaining part retains, in the receiving part, the accommodating cylinder received by the receiving part when there is no accommodating cylinder in the receiving part;

a height of the retaining part being smaller than the external diameter of the one-end part in the longitudinal direction of the accommodating cylinder;

a height of a part of the side wall that is adjacent to the retaining part in the second transport direction being greater than the external diameter of the one-end part in the longitudinal direction of the accommodating cylinder. With an apparatus for manufacturing a tampon of such a structure, the accommodating cylinder that cannot fit on the second transport path can be properly discharged out of the second transport path and the accommodating cylinder that is traveling on the second transport path can be prevented from falling off from the second transport path.

The above apparatus for manufacturing a tampon may further include:

an orienting mechanism that orients the accommodating cylinder;

the first transport path transporting the accommodating cylinder that has been oriented by the orienting mechanism into the first transport direction; and the orienting mechanism orients the accommodating cylinder in such a manner that the accommodating cylinder travels on the first transport path with the one-end part in the longitudinal direction of the accommodating cylinder being located on an upstream side in the first transport direction than the other-end part in the longitudinal direction of the accommodating cylinder. When the accommodating cylinder is passed from the first transport path to the second transport path, the accommodating cylinder may collide with the side wall. If the one-end part in the longitudinal direction where the petaloid parts are provided collides with the side wall, the petaloid parts may bend inwardly. With the above structure, the petaloid parts can be prevented from bending inwards.

Further, a method of manufacturing a tampon including a tampon main body, an accommodating cylinder that accommodates the tampon main body, and a pushing member that moves in the accommodating cylinder and pushes the tampon main body out of the accommodating cylinder, a plurality of petaloid parts being provided at a one-end part in the longitudinal direction of the accommodating cylinder, may be provided, the method including:

supplying the accommodating cylinder by a supplying mechanism; and inserting, by an inserting mechanism, the tampon main body and the pushing member into the accommodating cylinder supplied by the supplying mechanism, the supplying mechanism including:

a first transport path transporting the accommodating cylinder in a first transport direction lying along the longitudinal direction of the accommodating cylinder; and a second transport path transporting the accommodating cylinder in a second transport direction intersecting the longitudinal direction of the accommodating cylinder, the second transport path including:

a receiving part that receives from the first transport path the accommodating cylinder that has traveled on the first transport path;

a side wall formed on an end part opposite to a side where the accommodating cylinder is passed to the receiving part from the first transport path in the first transport direction; and an outlet that is formed in the side wall and discharges the accommodating cylinder out of the second transport path, the side wall retains in the receiving part the accommodating cylinder which the receiving part has received when there is no accommodating cylinder in the receiving part and discharges out of the second transport path through the outlet the accommodating cylinder which the receiving part has received when there is an accommodating cylinder in the receiving part. As has been described above, with such a method of manufacturing a tampon, the other accommodating cylinder can be prevented from being caught into the one-end part in the longitudinal direction of the accommodating cylinder and thus the accommodating cylinder can be supplied properly.

—Structure of Tampon—

In describing an apparatus and method of manufacturing a tampon of the present invention, the structure of the tampon 3010 manufactured by such apparatus and method of manufacturing will be described with reference to FIGS. 29 through 34.

Figure 29:
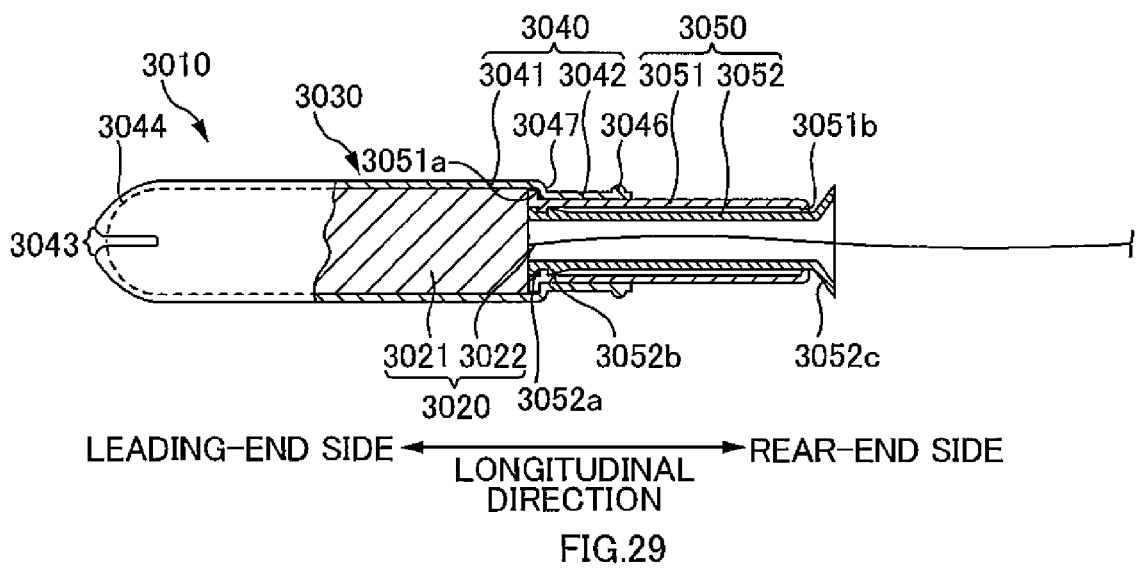
FIG. 29 is a cross-sectional view showing components of a tampon 3010.
Figure 30:
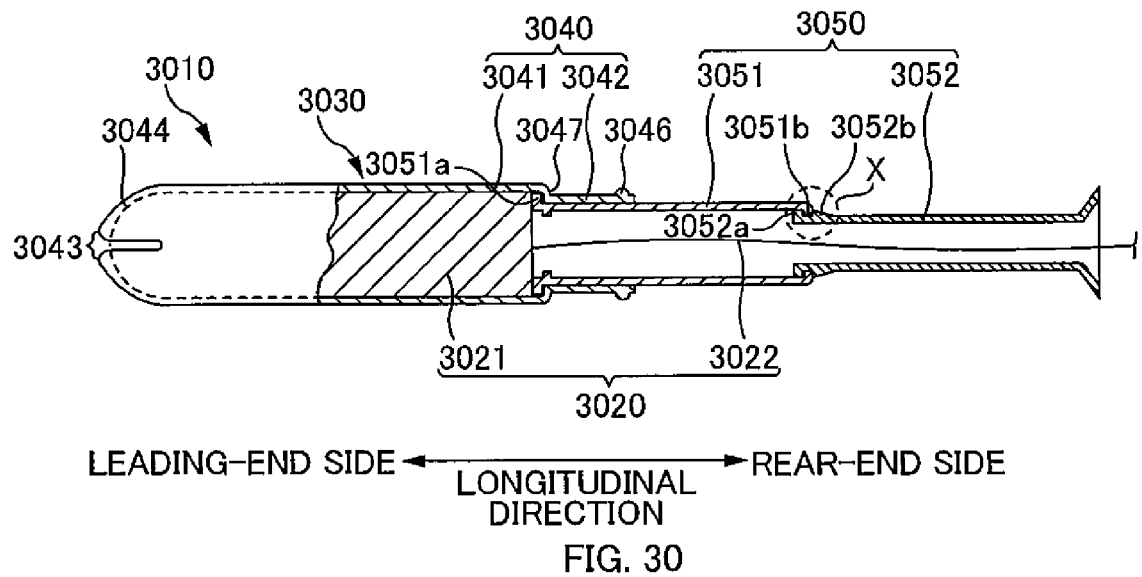
FIG. 30 is a cross-sectional view showing components of the tampon 3010.
Figure 31:
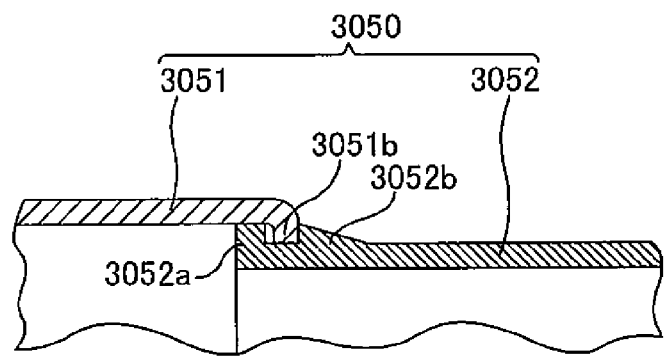
FIG. 31 is a diagram showing state in which a first inner cylinder 3051 and a second inner cylinder 3052 are joined.
Figure 32A:
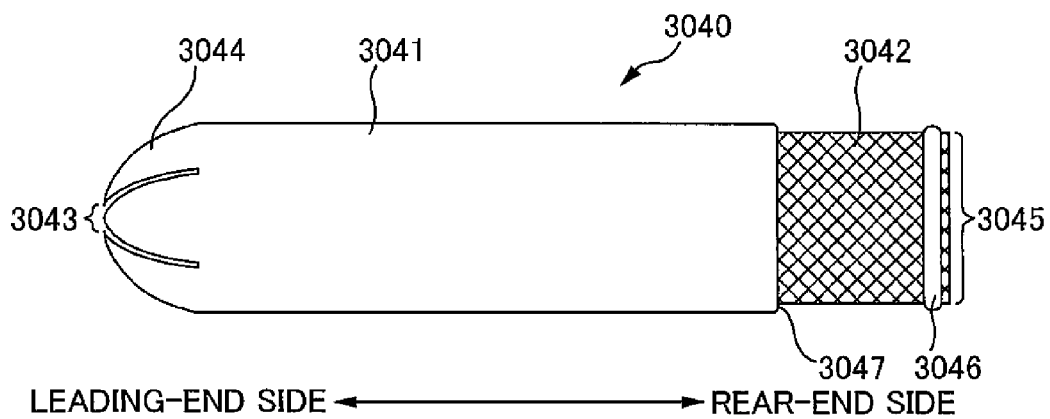
FIG. 32A is an external view of an outer cylinder 3040.
Figure 32B:
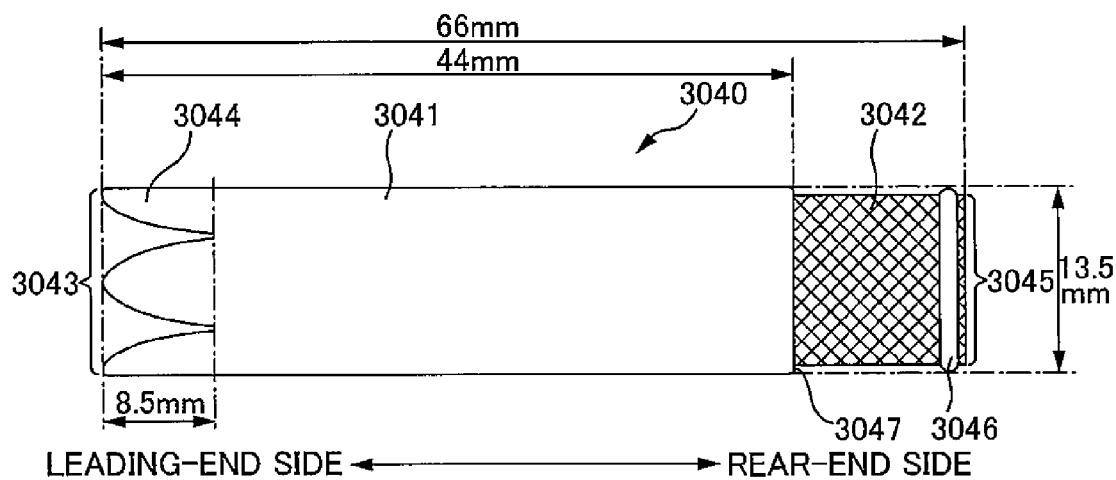
FIG. 32B is an external view of the outer cylinder 3040.
Figure 32C:
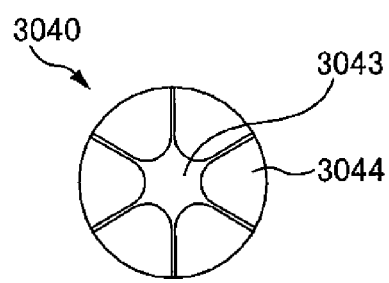
FIG. 32C is a diagram showing the outer cylinder 3040 shown in FIG. 32A from its leading-end side.
Figure 33:
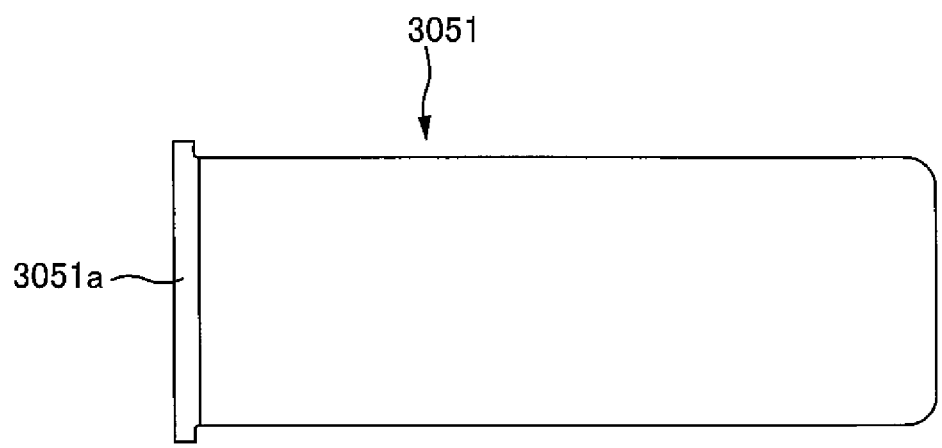
FIG. 33 is an external view of the first inner cylinder 3051.
Figure 34:
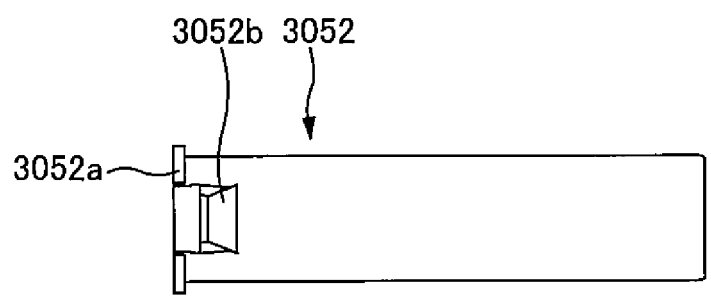
FIG. 34 is an external view of the second inner cylinder 3052.

FIGS. 29 and 30 are cross-sectional views showing the components of the tampon 3010. FIG. 29 shows the tampon 3010 in a state where the inner cylinder 3050 is contracted and FIG. 30 shows the tampon 3010 in a state where the inner cylinder 3050 is extended. FIG. 31 is a diagram showing how the first inner cylinder 3051 and the second inner cylinder 3052 are joined and is an enlarged view of the area labeled "X" in FIG. 30. FIGS. 32A and 32B are external views of the outer cylinder 3040. FIG. 32C is a diagram showing the outer cylinder 3040 shown in FIG. 32A from its leading-end side. FIG. 33 is an external view of the first inner cylinder 3051. FIG. 34 is an external view of the second inner cylinder 3052. In the following description, in the longitudinal direction of the tampon 3010, the side which is inserted in to the vaginal cavity is referred to as a leading-end side and the opposite side is referred to as a rear-end side.

As shown in FIG. 29, the tampon 3010 of the present embodiment is a sanitary product including a tampon main body 3020 and an applicator 3030. As shown in the same diagram, the tampon main body 3020 includes a cotton body 3021 and a cord 3022. The cotton body 3021 is an absorbent body that blocks the vaginal cavity and absorbs liquid such as menstrual blood, and is formed by cutting a cotton strip covered with non-woven fabric on both sides and by shaping into a substantially bullet like shape by heat forming. The cord 3022 extends through the rear-end side of the cotton body 3021 and is then held by a user when the cotton body 3021 inside the vaginal cavity is pulled out of the vaginal cavity. As shown in FIG. 29, the cord 3022 extends through the applicator 3030 and somewhat extends out of the rear end of the applicator.

The applicator 3030 is an aid device for guiding the tampon main body 3020 (specifically, the cotton body 3021) into a vaginal cavity. As shown in FIG. 29, the applicator 3030 includes an outer cylinder 3040 which is an example of a cylindrical accommodating member that accommodates the tampon main body 3020 and an inner cylinder 3050 which is an example of a pushing member that pushes the tampon main body 3020 out of the outer cylinder 3040.

The outer cylinder 3040 is a cylindrical body formed by injection molding a thermoplastic resin and has an appropriate flexibility. The outer cylinder 3040 includes a major diameter part 3041 provided on the leading-end part (corresponds to a one-end part in the longitudinal direction) and a minor diameter part 3042 provided at the rear-end part (corresponds to an other-end part in the longitudinal direction) and having an external diameter that is smaller than that of the major diameter part 3041. That is to say, an internal diameter of the leading-end part of the outer cylinder 3040 is greater than an external diameter of the rear-end part. It is to be noted that the dimensions of each part of the outer cylinder 3040 in the present embodiment is as shown in FIG. 32B.

The major diameter part 3041 is a part that has a slightly greater internal diameter than the diameter of the tampon main body 3020 and accommodates the tampon main body 3020 therein. The major diameter part 3041 is inserted into the vaginal cavity upon usage of the tampon 3010 with the tampon main body 3020 being accommodated therein. The tampon main body 3020 is accommodated in the major diameter part 3041 with its outer peripheral surface being in contact with the inner peripheral surface of the major diameter part 3041. The minor diameter part 3042 is a part held by a user when using the tampon 3010.

As shown in FIGS. 32A and 32B, the outer cylinder 3040 includes an opening formed at a leading end (hereinafter referred to as a leading-end opening 3043) of the outer cylinder 3040 and a plurality of petaloid parts 3044 (in this embodiment, six petaloid parts) at the leading-end part of the outer cylinder 3040 and surrounding the leading edge opening 3043. When shipping the tampon 3010, each of the plurality of petaloid parts 3044 is inwardly bent in an arc in the radial direction of the outer cylinder 3040 as shown in FIG. 32A. Therefore, when the outer cylinder 3040 is inserted into the vaginal cavity, the leading-end part of the outer cylinder 3040 is substantially hemispherical as shown in FIGS. 29 and 30 and the leading-end opening 3043 is substantially in a closed state as shown in FIG. 32C. On the other hand, as for the outer cylinder 3040 shortly after being injection molded, each of the plurality of petaloid parts 3044 is open (i.e., along the central axis of the outer cylinder 3040, as shown in FIG. 32B), and the leading-end opening 3043 is in an open state.

Further, as shown in FIG. 32A, the outer cylinder 3040 includes an opening formed at a rear end of the outer cylinder 3040 (hereinafter, referred to as a rear-end opening 3045) and an annular rib 3046 provided at a position slightly towards the leading-end side than the rear-end opening 3045. Further, an annular stepped part 3047 is formed between the major diameter part 3041 and the minor diameter part 3042.

The inner cylinder 3050 is a cylindrical body inserted into the minor diameter part 3042 of the outer cylinder 3040. The inner cylinder 3050 is located at a position nearer to the rear end-side than the tampon main body 3020 in the outer cylinder 3040 and moves along the central axis of the outer cylinder 3040 to pushes the tampon main body 3020 from the rear towards the leading-end opening 3043. Thereby, the tampon main body 3020 pushes each of the plurality of petaloid parts 3044 outwardly in the radial direction of the outer cylinder 3040 (in other words, opens the leading-end opening 3043) and is pushed out of the outer cylinder 3040. That is to say, the inner cylinder 3050 is movable in the outer cylinder 3040 and has a push-out function to push the tampon main body 3020 out of the outer cylinder 3040 through the leading-end opening 3043.

It is to be noted that the inner cylinder 3050 of the present embodiment has an extendable structure to make the over all length of the tampon 3010 compact. In detail, when the inner cylinder 3050 is contracted as shown in FIG. 29, the length of the inner cylinder 3050 is shorter than the outer cylinder 3040 and becomes a length suitable for carrying the tampon 3010. On the other hand, when the inner cylinder 3050 extends as shown in FIG. 30, the length of the inner cylinder 3050 will be a length sufficient to push the tampon main body 3020 out of the outer cylinder 3040. As has been described above, in order to make the inner cylinder 3050 extendable, in this embodiment, the inner cylinder 3050 has a two-tier structure. In detail, as shown in FIG. 29, the inner cylinder 3050 of the present embodiment includes a first inner cylinder 3051 and a second inner cylinder 3052 that is slidably inserted into the first inner cylinder 3051.

The first inner cylinder 3051 is a cylindrical body formed by injection molding plastics. The first inner cylinder 3051 has an external diameter that is slightly smaller than the internal diameter of the minor diameter part 3042. As shown in FIG. 29, The first inner cylinder 3051 is slidably inserted in the minor diameter part 3042. As shown in FIG. 33, an annular flange part 3051a is formed on an outer peripheral surface of the leading-end part of the first inner cylinder 3051. The flange part 3051a has an external diameter that is slightly smaller than the major diameter part 3041 of the outer cylinder 3040 and engages with an inner surface of the stepped part 2047, thereby preventing the inner cylinder 3050 from falling off from the rear-end opening 2045 of the outer cylinder 3040. When the inner cylinder 3050 pushes the tampon main body 3020 out of the outer cylinder 3040, the inner cylinder 3050 moves in such a manner that the outer peripheral surface of the flange part 3051a is in contact with the inner peripheral surface of the major diameter part 3041. Further, as shown in FIGS. 29 and 30, at the rear-end side on an inner peripheral surface of the first inner cylinder 3051, an annular protrusion 3051b extending inwardly in the radial direction of the first inner cylinder 3051 is provided.

The second inner cylinder 3052 is a cylindrical body formed by injection molding a thermoplastic resin. The second inner cylinder 3052 has an external diameter that is slightly smaller than the internal diameter of the first inner cylinder 3051. The second inner cylinder 3052 is, when the inner cylinder 3050 is in a contracted state, inserted in the first inner cylinder 3051 as shown in FIG. 29 and, when the inner cylinder 3050 is in an extended position, connected to the rear-end part of the first inner cylinder 3051 at the leading-end part of the second inner cylinder 3052 as shown in FIG. 30. Further, as shown in FIG. 34, on the outer peripheral surface of the leading-end part of the second inner cylinder 3052, an arcuate flange part 3052a and a protruded part 3052b located nearer to the rear-end side than the flange part 3052a is formed. As shown in FIG. 31, the height of the protruded part 3052b becomes lower at the rear-end. It is to be noted that the gap the gap between the flange part 3052a of the second inner cylinder 3052 and the protruded part 3052b is thicker than the thickness of the annular protrusion 3051b of the first inner cylinder 3051.

When the second inner cylinder 3052 is pulled towards the rear-end part, the annular protrusion 3051b of the first inner cylinder 3051 will be located between the flange part 3052a of the second inner cylinder 3052 and the protruded part 3052b. In such a state, as shown in FIG. 31, the annular protrusion 3051b engages the flange part 3052a and the protruded part 3052b and thereby the first inner cylinder 3051 and the second inner cylinder 3052 are joined.

Further, as shown in FIGS. 29 and 30, a flared part 3052c is formed at the rear end of the second inner cylinder 3052. Preferably, the external diameter of the flared part 3052c is greater than the internal diameter of the first inner cylinder 3051 and greater than the internal diameter of the minor diameter part 3042 of the outer cylinder 3040.

—Method of Manufacturing a Tampon 3010—

Figure 35A:
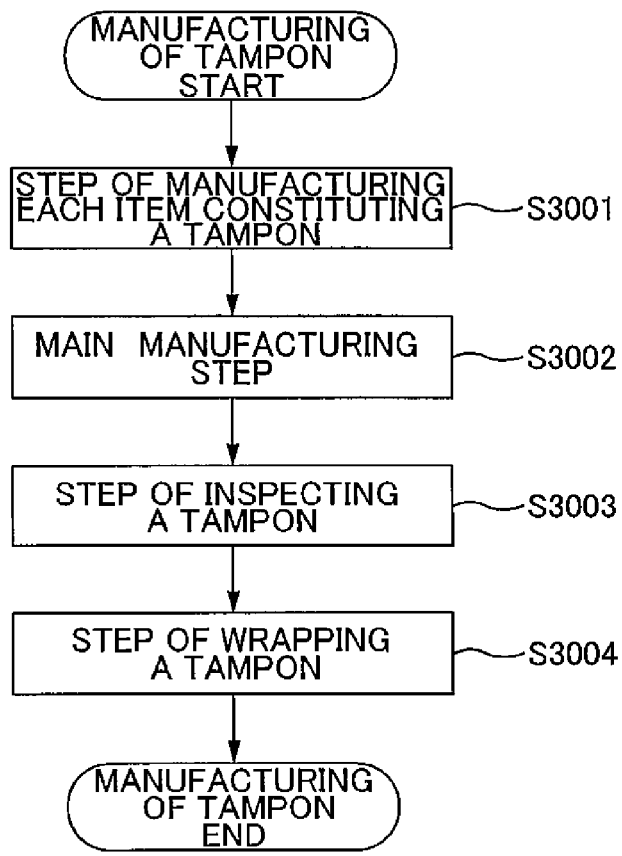
FIGS. 35A and 35B are flowcharts of the manufacturing of the tampon 3010.
Figure 35B:
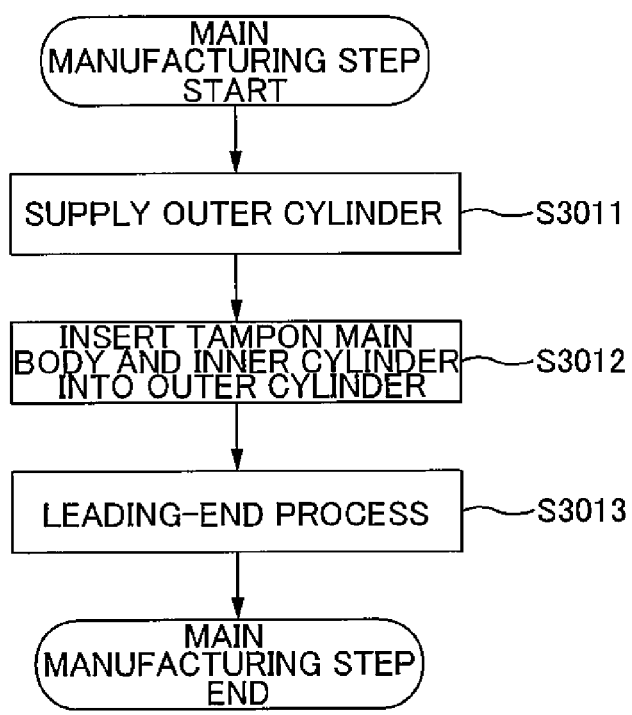

A method of manufacturing the tampon 3010 of the present embodiment will be described with reference to FIGS. 35A to 35D. FIGS. 35A and 35B are flowcharts showing how a tampon 3010 is manufactured. FIGS. 36A to 36D are diagrams in a series showing how a tampon 3010 is manufactured.

As shown in FIG. 35A, the method of manufacturing the tampon 3010 includes a step of manufacturing each item constituting the tampon 3010 (S3001), a step of supplying the manufactured items to an assembly apparatus 3100 to be described later and to manufacture the tampon 3010 by assembling the tampon 3010 (hereinafter referred to as a main manufacturing step S3002), a step of inspecting the manufactured tampon 3010 (S3003) and a step of wrapping the tampon 3010 (S3004).

As shown in FIG. 35B, the main manufacturing step S3002 starts with a step of supplying the injection molded outer cylinder 3040 (S3011). This step is performed by the supplying mechanism 3120 described later. It is to be noted that the outer cylinder 3040 at the step of being supplied by the supplying mechanism is in a state where the plurality of petaloid part 3044 are each in an open state (in other words, the leading-end opening 3043 is open). Thereafter, a step of inserting the tampon main body 3020 and the inner cylinder 3050 into the outer cylinder 3040 supplied by the supplying mechanism 3120 is performed (S3012). This step is performed by the inserting mechanism 3130 to be described later. The tampon 3010 is gradually assembled in accordance with the progress of the step.

Figure 36A:
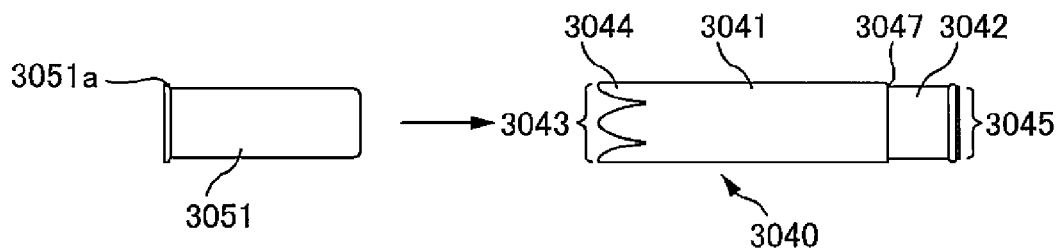
FIGS. 36A to 36D are diagrams in a series showing how the tampon 3010 is manufactured.

Now, the procedure of inserting the tampon main body 3020 and the inner cylinder 3050 into the outer cylinder 3040 is described in detail. As shown in FIG. 36A, the first inner cylinder 2051 is inserted into the outer cylinder 3040 through the leading-end opening 3043 of the outer cylinder 3040. The first inner cylinder 3051 inserted into the outer cylinder 3040 will be in a state where its rear-end part protrudes from the rear-end opening 3045 of the outer cylinder 3040 and the flange part 3051a engages the inner wall of the stepped part 3047 of the outer cylinder 3040 (see FIG. 36B).

Figure 36B:
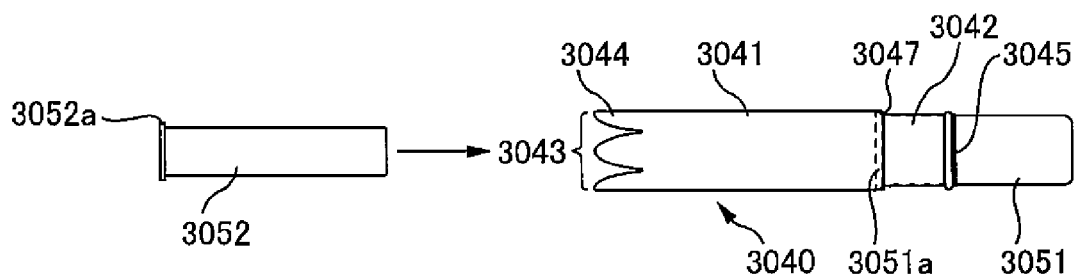

Then, as shown in FIG. 36B, the second inner cylinder 3052 is inserted into the outer cylinder 3040 through the leading-end opening 3043. The second inner cylinder 3052 inserted in the outer cylinder 3040 will be in a state where its rear-end part protrudes through the opening on the rear-end side of the first inner cylinder 3051 and the flange part 3052a engages with the inner peripherals surface of the first inner cylinder 3051 (see FIG. 36C). It is to be noted that, as shown in FIG. 36B, at the time supplied to the assembling apparatus 3100, a flared part 3052c is not yet formed on the second inner cylinder 3052. After the second inner cylinder 3052 is inserted into the outer cylinder 3040, the flared part 3052c will be formed by thermoforming the rear-end part of the second inner cylinder 3052. When the above-described steps are terminated, the assembly of the applicator 3030 is complete.

Figure 36C:
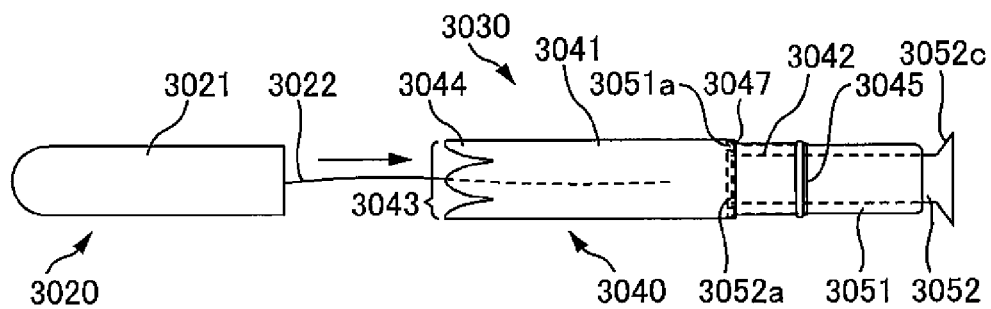
Figure 36D:
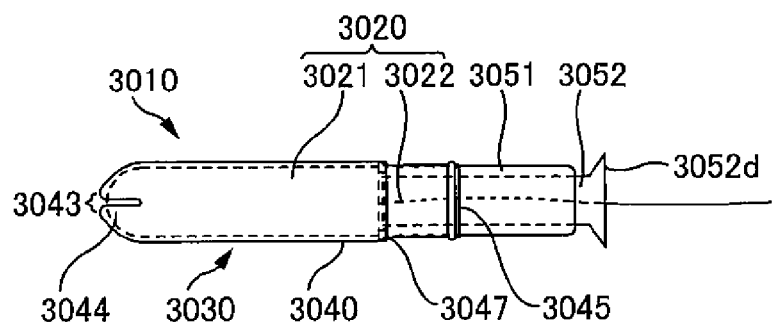

Then, as shown in FIG. 36C, the tampon main body 3020 is inserted into outer cylinder 3040 through the leading-end opening 3043. At this point, as shown in FIG. 36C, the tampon main body 3020 is inserted from its cord 3022 side. When the tampon main body 3020 is inserted in the outer cylinder 3040, the cotton body 3021 is accommodated in the major diameter part 3041 of the outer cylinder 3040 and the cord 3022 extends out of the rear end of the applicator 3030 (specifically, out of the opening on the rear-end of the second inner cylinder 3052). When the insertion of the tampon main body 3020 is terminated, the assembly of the tampon 3010 is complete.

After assembling the tampon 3010 in a manner described above, as shown in FIG. 36D, a process of heat forming is performed in which the leading-end of the outer cylinder 3040 is formed into a substantially hemispherical shape by bending each of the plurality of petaloid parts 2044 in such a manner that it is inclined inwardly in the radial direction of the outer cylinder 3040 (hereinafter referred to as a leading-end processing). When the leading-end processing is terminated, the main manufacturing step S3002 is complete.

It is to be noted that as described below, the assembling apparatus 3100 includes an assembling conveyor 3110 (see FIG. 37). This assembling conveyor 3110 intermittently carries out motions of transporting the assembled product in the transport direction (transport motions). Between the transport motions, i.e., when the assembled item is in a rest, each of the above-mentioned steps is sequentially performed.

—Assembling Apparatus 3100 of Tampon 3010—

Figure 37:
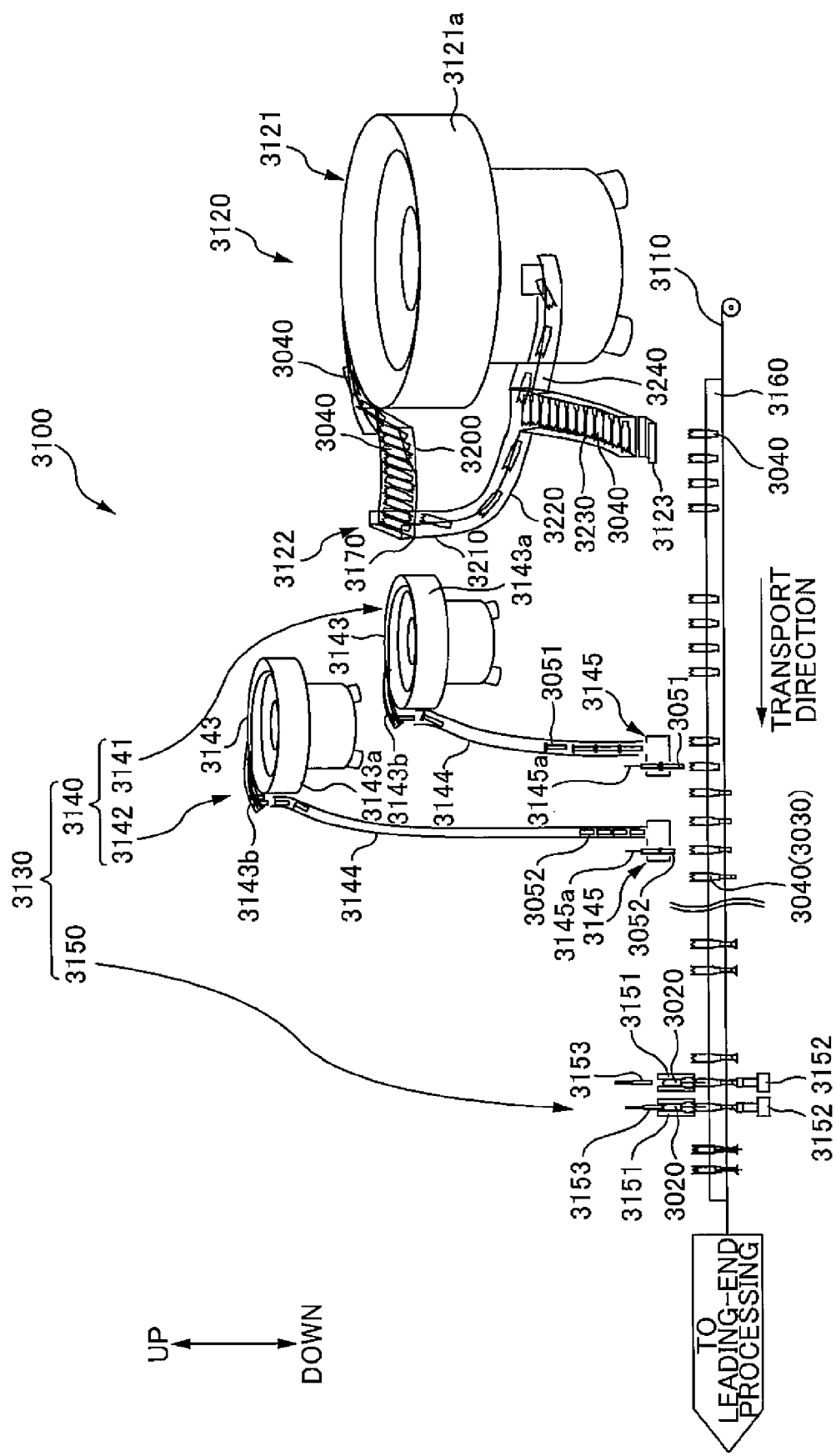
FIG. 37 is a diagram showing the assembling apparatus 3100 of the tampon 3010.

In the above-mentioned main manufacturing step S3002, a series of steps of assembling the tampon 3010 is performed by the assembling apparatus 3100 shown in FIG. 37. FIG. 37 is a diagram showing the assembling apparatus 3100. This assembling apparatus 3100 is an example of a manufacturing apparatus of the tampon 3010 and as shown in FIG. 37, includes an assembling conveyor 3110, a supplying mechanism 3120 and an inserting mechanism 3130.

The assembling conveyor 3110 is a device that transports the outer cylinder 3040 and items inserted in the outer cylinder 3040 (first inner cylinder 3051, second inner cylinder 3052 and tampon main body 3020) in the transport direction (direction indicated by an arrow in FIG. 37). A mount 3160 that mounts the outer cylinder 3040 thereon is placed on the assembling conveyor 3110 and the mount 3160 is transported in the transport direction by the assembling conveyor 3110. Thereby, the outer cylinder 3040 mounted on the mount 3160 and the items inserted in the outer cylinder 3040 are transported in the transport direction together with the mount 3160. Circular holes 3161 (for example, see FIG. 39) are formed in the mount 3160 in the vertical direction and the outer cylinder 3040 is mounted on the mount 3160 by fitting into the circular hole 3161 from the rear-end side. The outer cylinder 3040 mounted on the mount 3160 will be in a state that the central axis of the outer cylinder 3040 lies along the vertical direction and the leading-end opening 3043 faces directly upwards as shown in FIG. 37.

The supplying mechanism 3120 is a mechanism that individually supplies the injection molded outer cylinder 3040. As shown in FIG. 37, some of the outer cylinders 3040 supplied by the supplying mechanism 3120 are mounted on the mount 3160 and are transported by the assembling conveyor 3110 together with the mount 3160. It is to be noted that an orienting mechanism 3170 that orients the outer cylinders 3040 is built in the supplying mechanism 3120 of the present embodiment. (In other words, the assembling apparatus 3100 of the present embodiment includes an orienting mechanism 3170.) This orienting mechanism 3170 orients the outer cylinders 3040 in such a manner that the orientation of the outer cylinder 3040 supplied by the supplying mechanism 3120 is in the predetermined orientation. Since the outer cylinders 3040 are oriented by the orienting mechanism 3170, the outer cylinders 3040 are mounted on the mount 3160 in a state shown in FIG. 37. (That is to say, the central axis of the outer cylinder 3040 lies along the vertical direction and the leading-end opening 3043 faces directly upwards.) Details of each of the supplying mechanism 3120 and the orienting mechanism 3170 will be described later.

The inserting mechanism 3130 is a mechanism that inserts the inner cylinder 3050 and the tampon main body 3020 into the outer cylinder 3040 mounted on the mount 3160 that is apart of the outer cylinders 3040 supplied by the supplying mechanism 3120. As shown in FIG. 37, the inserting mechanism 3130 includes an inner cylinder inserting mechanism 3140 that inserts the inner cylinder 3050 into the outer cylinder 3040 and a tampon main body inserting mechanism 3150 that inserts the tampon main body 3020 into the outer cylinder 3040.

The inner cylinder inserting mechanism 3150 inserts the inner cylinder 3050 into the outer cylinder 3040 mounted on the mount 3160 through the leading-end opening 3043 of the outer cylinder 3040. It is to be noted that the inner cylinder inserting mechanism 3140 of the present embodiment includes a mechanism that inserts a first inner cylinder 3051 constituting the outer cylinder 3040 into the outer cylinder 3040 (hereinafter referred to as a first inner cylinder inserting mechanism 3141) and a mechanism that similarly inserts the second inner cylinder 3052 constituting the inner cylinder 3050 into the outer cylinder 3040 (hereinafter referred to as a second inner cylinder inserting mechanism 3142) respectively.

As shown in FIG. 37, the first inner cylinder inserting mechanism 3141 includes an inner cylinder feeder 3143, an inner cylinder pressing device 3145 that presses and inserts the first inner cylinder 3051 into the outer cylinder 3040 and a tube 3144 provided between the inner cylinder feeder 3143 and the inner cylinder pressing device 3145.

The inner cylinder feeder 3143 is a parts feeder including a bowl-shaped vibratory table 3143a. By vibrating the vibratory table 3143a, the inner cylinder feeder 3143 moves the first inner cylinders 3051 accumulated at the bottom part of the vibratory table 3143a sequentially and spirally from the bottom part.

Also, as shown in FIG. 37, a pair of rails 3143b is connected to the terminal end part of the vibratory table 3143a. Between the pair of rails 3143b, a gap that is slightly longer than the external diameter of the first inner cylinder 3051 is formed. The first inner cylinder 3051 that has moved on the vibratory table 3143a travels along the rails 3143b while being held between the pair of rails 3143b. At this time, the flange part 3051a of the first inner cylinder 3051 hangs at the top part of the rails 3143b and the first inner cylinder 3051 will be suspended from the rails 3143b. Then, after passing the terminal end of the rails 3143b, the first inner cylinder 3051 drops with the leading-end of the first inner cylinder 3051 being located above the rear-end and supplied to the inner cylinder pressing device 3145 through the tube 3144.

The inner cylinder pressing device 3145 receives the first inner cylinder 3051 that has dropped through the tube 3144. When the outer cylinder 3040 is transported to a position below the inner cylinder pressing part 3145 by the assembly conveyor 3110, the inner cylinder pressing device 3145 presses down the received first inner cylinder 3050 by a pressing jig 3145a. Thus, the first inner cylinder 3051 is inserted into the outer cylinder 3040 through the leading-end opening 3043 of the outer cylinder 3040.

Since the second inner cylinder inserting mechanism 3142 has a structure that is substantially similar to that of the first inner cylinder inserting mechanism 3141, it will not be described in detail here. As shown in FIG. 37, the second inner cylinder inserting mechanism 3142 is provided at a downstream position, in the transport direction of the transport conveyor 2110, than the first inner cylinder inserting mechanism 3141. Accordingly, the second inner cylinder inserting mechanism 3142 inserts the second inner cylinder 3052 into the outer cylinder 3040 in which the first inner cylinder 3051 is inserted.

The tampon main body inserting mechanism 3140 inserts the tampon main body 3020 into the outer cylinder 3040 through the leading-end opening 3043 of the outer cylinder 3040. The tampon main body inserting mechanism 3150 is provided on the downstream side of the inner cylinder inserting mechanism 3140 in the transport direction of the assembling conveyor 3110. Accordingly, the tampon main body inserting mechanism 3150 inserts the tampon main body 3020 into the outer cylinder 3040 in which the first inner cylinder 3051 and the second inner cylinder 3052 are inserted (in other words, the assembled applicator 3030). As shown in FIG. 37, the tampon main body inserting mechanism 3150 includes a guide tube 3151, a suction device 3152 and a tampon main body pressing device 3153.

The guide tube 3151 is a cylindrical body that guides the tampon main body 3020 when the tampon main body 3020 is inserted into the outer cylinder 3040. With the tampon main body 3020 being held inside the guide tube 3151, the guide tube 3151 is connected to the outer cylinder 3040 mounted on the mount 3160 as shown in FIG. 37. In detail, when the outer cylinder 3040 is transported to the position below the guide tube 3151 by the assembling conveyor 3110, the guide tube 3151 is lowered. Thus, the leading-end part of the outer cylinder 3040 will fit into the lower end of the guide tube 3151. It is to be noted that the tampon main body 3020 is held inside the guide tube 3151 in such a manner that the cord 3022 hangs down at a position below the cotton body 3021.

The tampon main body pressing device 3153 presses down the tampon main body 3020 held inside the guide tube 3151 in a state that the guide tube 3151 is connected to the outer cylinder 3040. Thereby, the tampon main body 3020 moves inside the guide tube 3151 and is inserted into the outer cylinder 3040 connected to the guide tube 3151 from the side where the cord 3022 is provided.

The suction device 3152 takes the air in from the rear-end side of the outer cylinder 3040 (specifically, an opening at the rear-end side of the second inner cylinder 3052 inserted in the outer cylinder 3040) while the tampon main body pressing device 3153 is pressing the tampon main body 3020. According to the suction of the suction device 3152, the cord 3022 will be pulled directly downwards when the tampon main body 3020 is inserted into the outer cylinder 3040. As a result, the cord 3022 will smoothly passes through the leading-end opening 3043 of the outer cylinder 3040. It is to be noted that at the time when the tampon main body 3020 is accommodated into the outer cylinder 3040, the cord 3022 is somewhat pulled out of the rear-end opening (in other words, the rear end of the assembled applicator 3030) of the second inner cylinder 3052 inserted into the outer cylinder 3040.

—Structure of Supplying Mechanism 3120 and Orienting Mechanism 3170—

<Structure of Supplying Mechanism 3120>

Figure 38:
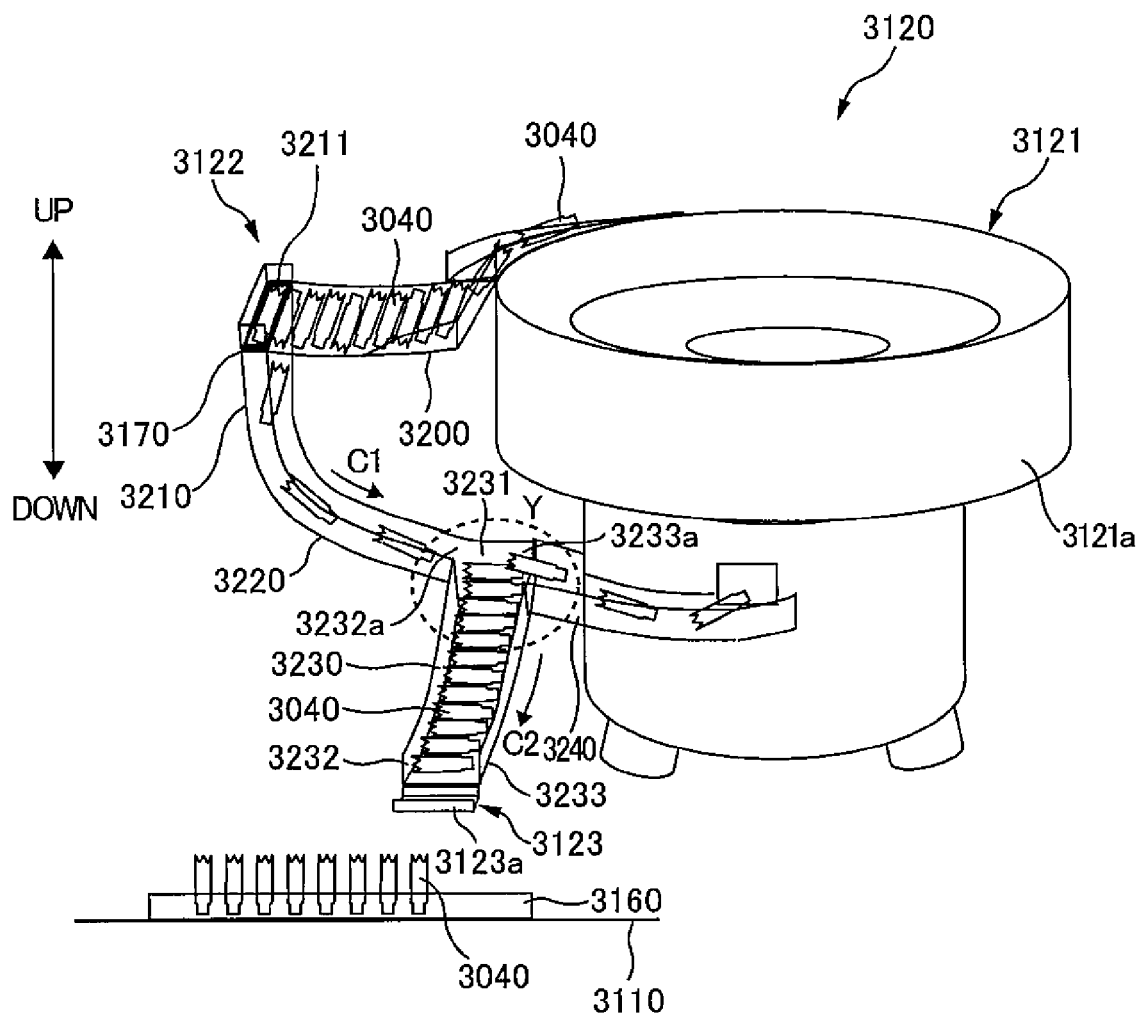
FIG. 38 is an enlarged view of a supplying mechanism 3120 shown in FIG. 37.
Figure 39:
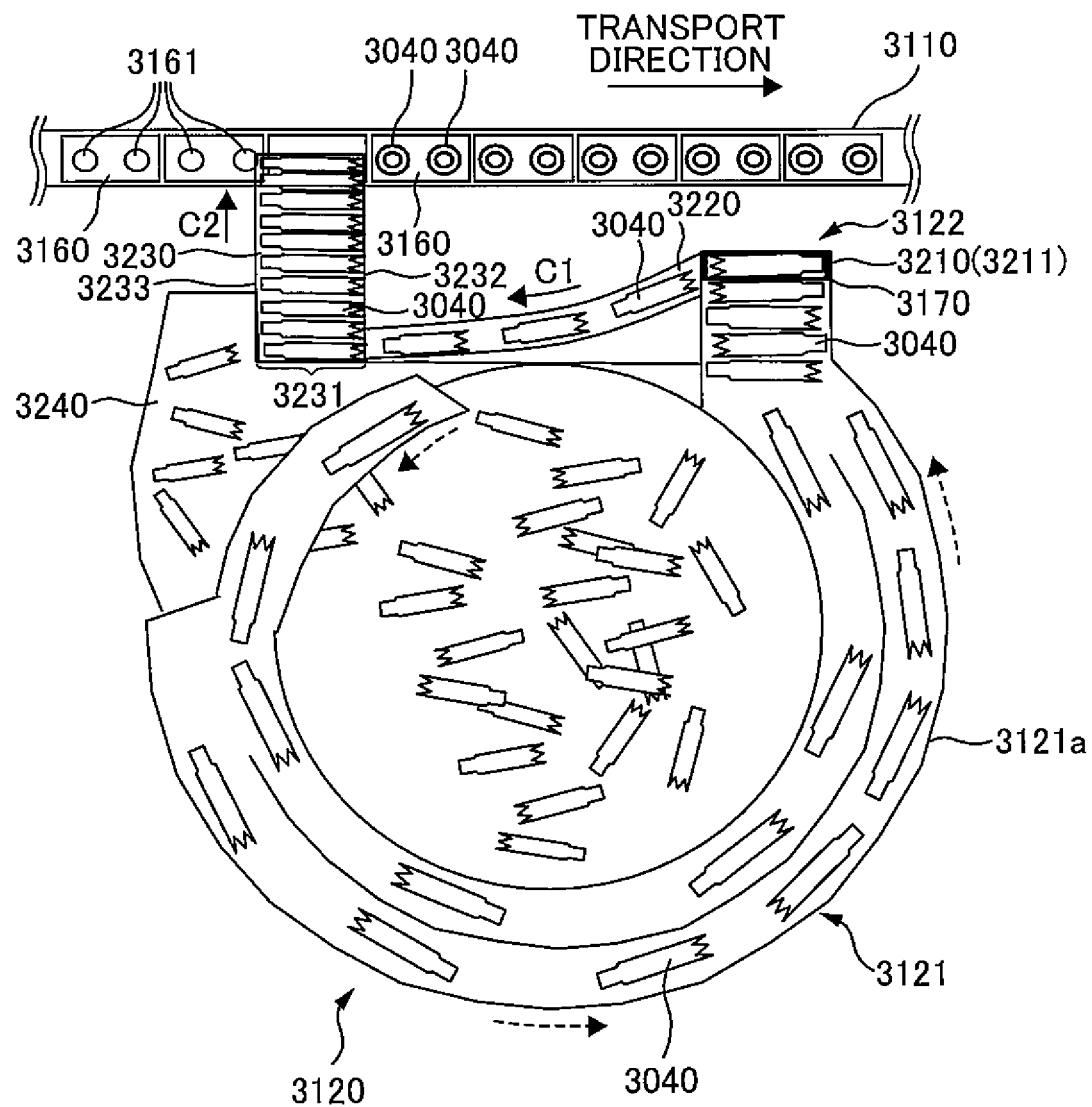
FIG. 39 is a top plan view of the supplying mechanism 3120.

The structure of the above-described supplying mechanism 3120 will be described with reference to FIGS. 38 and 39. FIG. 38 is an enlarged view of the supplying mechanism 3120 shown in FIG. 37. FIG. 39 is a top plan view of the supplying mechanism 3120.

As has been described above, the supplying mechanism 3120 supplies the injection molded outer cylinders 3040 individually. That is to say, the outer cylinder 3040 supplied by the supplying mechanism 3120 is set at regular intervals on the assembling conveyor 3110. (Specifically, it is mounted on the mount 3160 placed on the assembling conveyor 3110.) Also, as shown in FIG. 38, the supplying mechanism 3120 includes an outer cylinder feeder 3121, a transport path 3122 and an outer cylinder setting part 3123. Hereinafter, each component of the supplying mechanism 3120 will be described.

<Outer Cylinder Feeder 3121>

The outer cylinder feeder 3121 is a parts feeder 3121 including a bowl-shaped vibratory table 3121a and is a device that moves the outer cylinder 3040 mounted on the vibratory table 3121a by vibrating the vibratory table 3121a. Here, the vibratory table 3121a is an example of the placing table. Then the injection molded outer cylinders 3040 are once accumulated at the bottom part of the vibratory table 3121a and then move spirally from the bottom part as shown in FIG. 39. It is to be noted that the outer cylinder 3040 moves on the vibratory table 3121a in such a manner that its direction of movement (in FIG. 39, the direction shown by a broken-line arrow) lies along the longitudinal direction of the outer cylinder 3040. Then, the outer cylinder feeder 3121 moves the plurality of outer cylinders 3040 in such a manner that the plurality of outer cylinders 3040 aligns in the direction of movement on the vibratory table 3121a.

<Transport Path 3122>

The transport path 3122 receives the outer cylinder 3040 that has moved on the vibratory table 3121a and to transport the outer cylinder 3040. As shown in FIG. 38, the transport path 3122 includes, from the top, a guide path 3200, a drop chute 3210, a first transport path 3220, a second transport path 3230 and a third transport path 3240.

The guide path 3200 is apart of the transport path 3122 that receives the outer cylinder 3040 from the outer cylinder feeder 3121 and guides the outer cylinder 3040 to the drop chute 3210. The guide path 3200 is formed at the upstream side end part of the transport path 3122 and is located at the upper most position in the transport path 3122. The starting end part of the guide path 3200 is directly connected to the vibratory table 3121a and the terminal end part of the guide path 3200 extends to an opening 3211 in the drop chute 3210. After being passed to the guide path 3200, the outer cylinder 3040 that has moved on the vibratory table 3121a is guided by the guide path 3200 and moves towards the drop chute 3210. It is to be noted that since the starting end part of the guide part 3200 is directly connected to the vibratory table 3121a, the vibration of the vibratory table 3121a is transferred to the guide part 3200. Therefore, since the guide part 3200 vibrates by the vibration transferred from the vibratory table 3121a, the outer cylinder 3040 will move on the guide part 3200.

Also, as shown in FIGS. 38 and 39, when the outer cylinder 3040 is passed from the vibratory table 3121a to the guide part 3200, the orientation of the outer cylinder 3040 is changed. In detail, the orientation of the outer cylinder 3040 that has moved on the vibratory table 3121a in the longitudinal direction of the outer cylinder 3040 is changed in such a manner that it moves in a direction intersecting the longitudinal direction of the outer cylinder 3040 on the guide path 3200. The purpose of changing the orientation of the outer cylinder 3040 is to input the outer cylinder 3040 into the drop chute 3210 in such a state that the longitudinal direction of the outer cylinder 3040 lies along the longitudinal direction of the opening 3211 of the drop chute 3210. The outer cylinder 3040 the orientation of which has turned over in a manner described above travels on the guide path 3200 while maintaining such an orientation. On the other hand, the outer cylinder 3040 whose orientation was not properly changed will be rejected and returns to the bottom part of the vibratory table 3121a.

The outer cylinder 3040 that has moved on the guide path 3200 is inputted into the drop chute 3210 one by one. Here, a number of outer cylinders 3040 passed from the outer cylinder feeder 3121 to the guide path 3200 at a unit time is greater than a number of outer cylinders 3040 inputted into the drop chute 3210 from the guide path 3200 at a unit time. Therefore, on the guide path 3200, as shown in FIGS. 38 and 39, the outer cylinders 3040 are temporarily accumulated side-by-side (specifically, in a state that they are aligned in a direction intersecting the longitudinal direction of the outer cylinder 3040).

The drop chute 3210 is a part of the transport path 3122 through which the outer cylinder 3040 that has traveled on the guide path 3200 is dropped substantially directly downwards. The opening 3211 in the drop chute 3210 is substantially rectangular and is adjacent to the terminal end part of the guide path 3200. Among the outer cylinders 3040 accumulated on the guide path 3200, the outer cylinder 3040 located at the most terminal part of the guide path 3200 is inputted and dropped into the drop chute 3210 through the opening 3211. As has been described above, the outer cylinder 3040 is inputted into the drop chute 3210 with the longitudinal direction of the outer cylinder 3040 lying along the longitudinal direction of the opening 3211.

Further, the orienting mechanism 3170 is provided at the opening 3211 of the drop chute 3210. While being inputted into the drop chute 3210 from the opening 3211, the outer cylinder 3040 is oriented by the orienting mechanism 3170. To be more specifically, the orientation of the outer cylinder 3040 is oriented in such a manner that the rear end part of the outer cylinder 3040 drops before the leading-end part. Thereafter, the outer cylinder 3040 maintains the orientation mentioned above and drops to the lower-end part of the drop chute 3210.

The first transport path 3220 is a part that is connected to the lower-end part of the drop chute 3210 and transports the outer cylinder 3040 that has dropped through the drop chute 3210. The outer cylinder 3040 that has been sent from the outer cylinder feeder 3121 reaches the first transport path 3220 via the guide path 3200 and the drop chute 3210 and then transported by the first transport path 3220. In other words, the outer cylinder feeder 3121 moves the outer cylinder 3040 mounted on the vibratory table 3121a provided in the outer cylinder feeder 3121 towards the first transport path 3220.

The first transport path 3220 transports the outer cylinder 3040 in the first transport direction (direction labeled "C1" in FIGS. 38 and 39) lying along the longitudinal direction of the outer cylinder 3040. The first transport path 3220 is inclined in such a manner that the outer cylinder 3040 slides down the first transport path 3220. Further, since the first transport path 3220 is located at a position on the downstream side of the orienting mechanism 3170, the first transport path 3220 transports the outer cylinder 3040 that has been oriented by the orienting mechanism 3170. As has been described above, the orienting mechanism 3170 orients the outer cylinder 3040 in such a manner that the rear end part of the outer cylinder 3040 drops before the leading-end part. Therefore, the outer cylinder 3040 will move on the first transport path 3220 with the leading-end part of the outer cylinder 3040 being located on the upstream side the rear-end part.

The second transport path 3230 is a part that is connected to the terminal end part of the first transport path 3220 and receives and transports the outer cylinder 3040 that has traveled on the first transport path 3220 from the first transport path 3220. The second transport path 3230 is, in a similar manner to the first transport path 3220, inclined in such a manner that the outer cylinder 3040 slides down the second transport path 3230. The second transport path 3230 extends towards the assembling conveyor 3110. Therefore, the outer cylinder 3040 slides down the second transport path 3230 and moves towards the assembling conveyor 3110. The outer cylinder 3040 that has slid down the second transport path 3230 is passed to an outer cylinder setting part 3123 which will be described later and set on the assembling conveyor 3110 by the outer cylinder setting part 3123.

As shown in FIGS. 38 and 39, the second transport path 3230 is formed in such a manner that it intersects with (specifically, so as to be perpendicular to) the first transport path 3220. Therefore, the second transport direction (direction labeled "C2" in FIG. 39) in which the second transport path 3230 transports the outer cylinder 3040 intersects (is perpendicular to) the first transport direction. In other words, the second transport path 3230 transports the outer cylinder 3040 received from the first transport path 3220 in the second transport direction that intersects with (is perpendicular to) the longitudinal direction of the outer cylinder 3040.

In the following description, the purpose of providing the direction in which the second transport path 3230 transports the outer cylinder 3040 (second transport direction) in such a manner that it intersects (is perpendicular to) the direction in which the first transport path 3220 transports the outer cylinder 3040 (first transport direction) will be described.

As shown in FIGS. 38 and 39, there is a case where the outer cylinders 3040 accumulate in the second transport path 3230. This is because the number of outer cylinders 3040 passed from the first transport path 3220 to the second transport path 3230 per unit time is greater than the number of outer cylinders 3040 passed from the second transport path 3230 to the outer cylinder setting part 3123 per unit time. Now, assuming a case in which the second transport path 3230 transports the outer cylinders 3040 in the direction lying along the longitudinal direction of the outer cylinder 3040, from the reason described above, the outer cylinders 3040 will accumulate in the direction lying along the longitudinal direction of the outer cylinder 3040 on the second transport path 3230 (that is to say, the outer cylinders 3040 accumulate in a longitudinally aligned state). Also, by means of the orienting mechanism 3170, the outer cylinder 3040 is oriented in such a manner that it travels on the first transport path 3220 with the leading-end part of the outer cylinder 3040 being located upstream of the rear-end part in the first transport direction. As a result, if the outer cylinders 3040 accumulate on the second transport path 3230 in a longitudinally aligned manner, the outer cylinders 3040 will be mutually connected on the second transport path 3230.

Explaining in detail, among the outer cylinders 3040 accumulated on the second transport path 3230, if we focus on the neighboring two outer cylinders 3040, the rear-end part of the outer cylinder 3040 at the upstream side is caught in the leading-end opening 3043 of the outer cylinder 3040 at the downstream side (a so-called jamming). This jamming occurs when the plurality of petaloid parts 3044 provided on the downstream side outer cylinder 3040 inclines outwards and the leading-end opening 3043 is broadened, and the rear-end part of the outer cylinder 3040 on the upstream side easily get caught in such rear-end opening 3045.

Whereas in the present embodiment, the outer cylinders 3040 are accumulated on the second transport path 3230 in a side-by-side manner. Therefore, the jamming does not occur on the second transport path 3230 and the outer cylinders 3040 can be properly accumulated on the second transport path 3230. As shown in FIGS. 38 and 39, the outer cylinders 3040 accumulated on the second transport path 3230 are in mutually the same orientation. This is because the outer cylinders 3040 travels on the first transport path 3220 with the same orientation oriented by the orienting mechanism 3170 and passed to the second transport path 3230 while keeping the same orientation.

Figure 42:
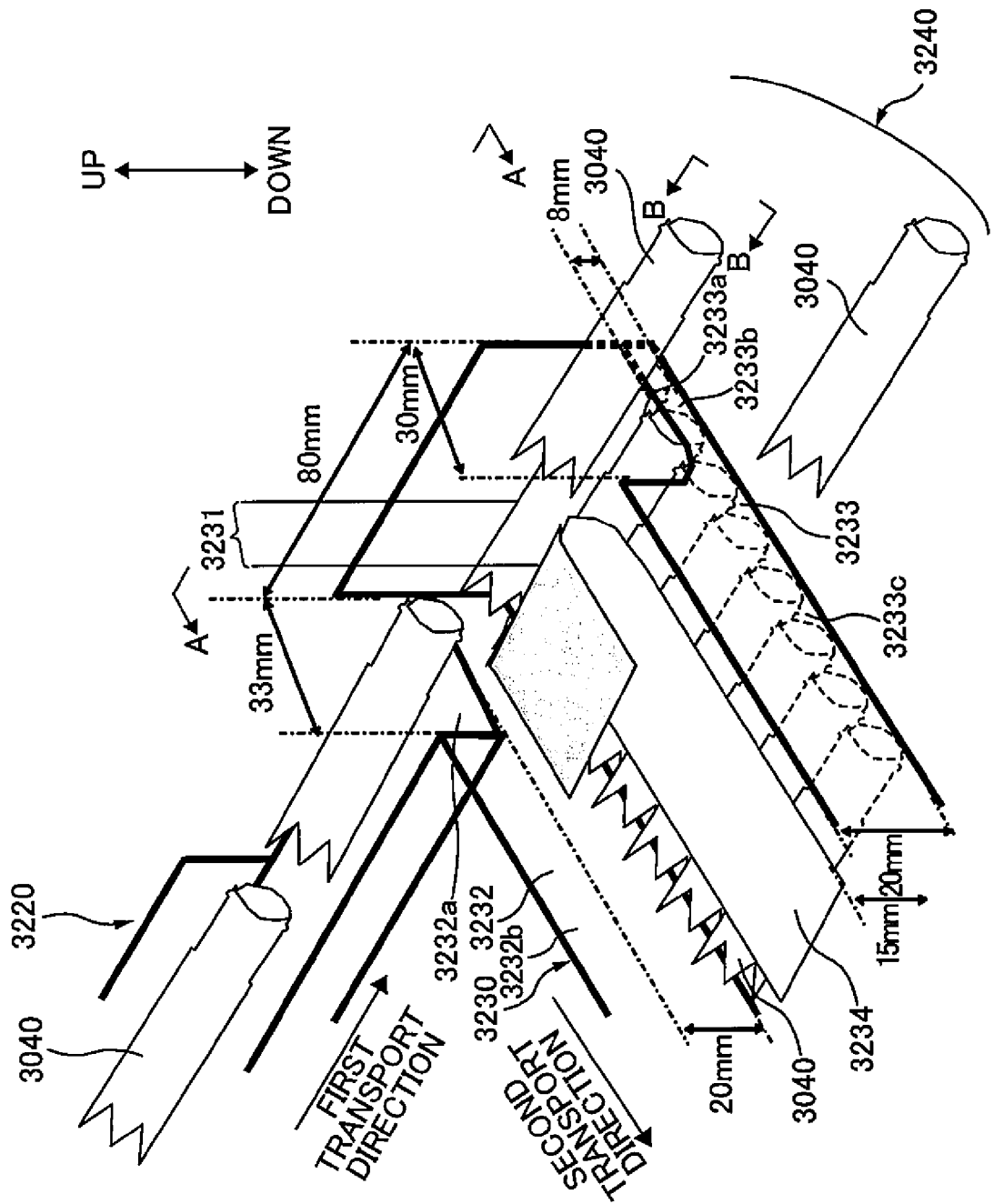
FIG. 42 is an enlarged view of the area labeled "Y" in FIG. 38.

The starting-end part of the second transport path 3230 (i.e., the upstream end part of the second transport path 3230 in the second transport direction) is connected to the terminal end part of the first transport path 3220 via a stepped part and is located at a position lower than the terminal end part of the first transport path 3220 (for example, see FIG. 42). Therefore, the outer cylinder 3040 that has slid down the first transport path 3220 drops after reaching the terminal end of the first transport path 3220 and is received by the starting end part of the transport path 3230. In other words, the starting end part of the second transport path 3230 includes a receiving part 3231 that receives the outer cylinder 3040 that has traveled (slid down) the first transport path 3220 from the first transport path 3220. As will be described later, the receiving part 3231 of the present embodiment is capable of holding a single outer cylinder 3040 received from the second transport path 3230.

Further, the second transport path 3230 includes side walls 3232 and 3233 at both end parts in the direction intersecting the second transport direction (the first transport direction). The side walls 3232 and 3233 extends from the upstream side part of to the downstream side part the second transport path 3230 and stands substantially upright. The outer cylinder 3040 on the second transport path 3230 travels on the second transport path 3230 in a state that it is held between the side walls 3232 and 3233. The gap between the side walls 3232 and 3233 is somewhat longer than the length between the leading-end part and the rear end part of the outer cylinder 3040 while the petaloid parts 3044 are open (specifically, approximately 66 mm) and is approximately 80 mm in the present embodiment. (See FIG. 42).

As shown in FIG. 38, among the side walls 3232 and 3233, in the side wall 3232 formed at the end part (hereinafter referred to as one-end part) at the side where the outer cylinder 3040 is passed from the first transport path 3220 to the receiving part 3231 in the first transport direction, an inlet 3232a is formed that guides the outer cylinder 3040 that has traveled on the first transport path 3220 into the receiving part 3231.

On the other hand, the end part (hereinafter referred to as other-end part) opposite to the side to which the outer cylinder 3040 is passed to the receiving part 3231, an outlet 3233a is formed that discharges the outer cylinder 3040 out of the second transport path 3230. From this outlet 3233a, the outer cylinder 3040 received by the receiving part 3231 while the outer cylinder 3040 is on the receiving part 3231 (that is to say, the outer cylinder 3040 that the receiving part 3231 which is already holding the outer cylinder 3040 has newly received) is discharged. It is to be noted that either of the inlet 3232a and outlet 3233a is provided at the starting-end part of the second transport path 3230 and is located at substantially the same position in the second transport direction.

The third transport path 3240 is a part connected to the starting-end part of the second transport path 3230 and receives and transports the outer cylinder 3040 discharged out of the second transport path 3230 through the above-mentioned outlet 3233a. The third transport path 3240 is, in a similar manner to the first transport path 3220 and the second transport path 3230, inclined in such a manner that the outer cylinder 3040 slides down the third transport path 3240. Further, the third transport path 3240 extends from the outlet 3233a to the base part of the vibratory table 3121a of the outer cylinder feeder 3121. Therefore, the outer cylinder 3040 that is discharged out of the second transport path 3230 through the outlet 3233a is returned to the outer cylinder feeder 3121 by sliding on the third transport path 3240 and will travel again on the transfer path 3122 from the transport path 3122.

<Outer Cylinder Setting Part 3123>

The outer cylinder setting part 3123 receives the outer cylinder 3040 that has slid down the second transport path 3230 from the second transport path 3230 and sets the outer cylinder 3040 on the assembling conveyor 3110. In detail, the outer cylinder setting part 3123 mounts the outer cylinder 3040 received from the second transport path 3230 on the mount 3160 placed on the assembling conveyor 3110.

Figure 40A:
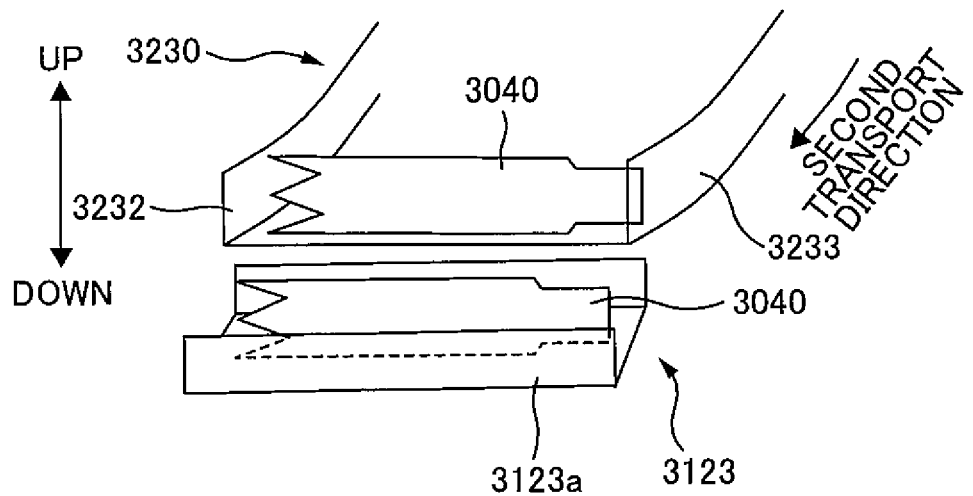
FIGS. 40A and 40B are a diagram showing an outer cylinder setting part 3123.
Figure 40B:
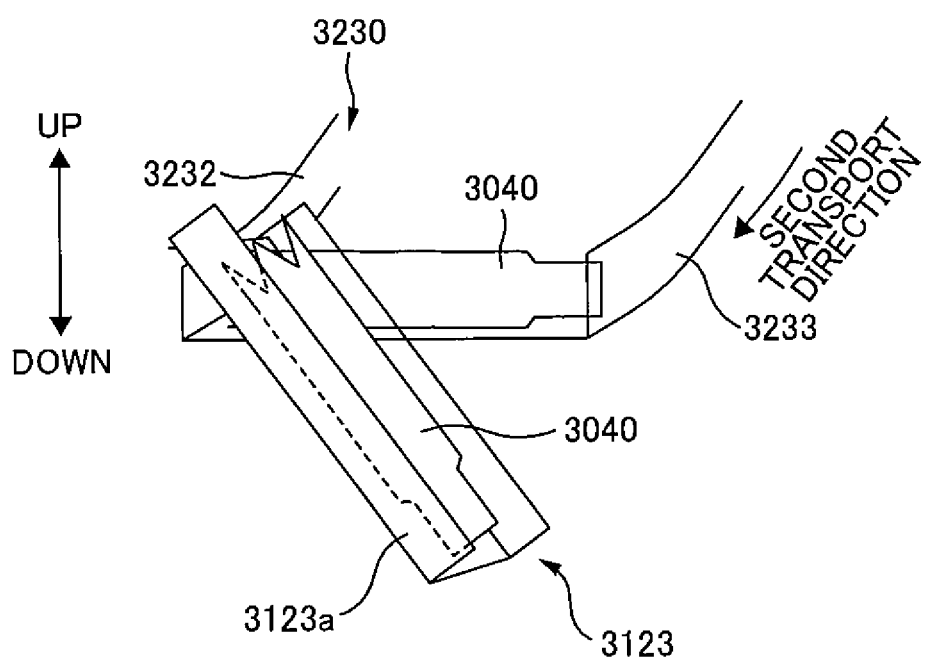

As shown in FIGS. 40A and 40B, the outer cylinder setting part 3123 includes an outer cylinder receiving table 3123a and a rotator mechanism (not shown) that rotates the outer cylinder receiving table 3123a. FIGS. 40A and 40B are diagrams showing the outer cylinder setting part 3123. The outer cylinder receiving table 3123a is located at a position adjacent to the terminal-end part of the second transport path 3230 in the second transport direction. The outer cylinder receiving table 3123a is located below the terminal end of the second transport path 3230. The outer cylinder receiving table 3123a receives the outer cylinder 3040 dropped from the terminal end part of the second transport path 3230. It is to be noted that the number of outer cylinders that the outer cylinder receiving table 3123a can receive is one.

As shown in FIG. 40A, the outer cylinder receiving table 3123a receives the outer cylinder 3040 in a state that its longitudinal direction lying along the horizontal direction. After receiving the outer cylinder 3040, the outer cylinder receiving table 3123a rotates in such a manner that the longitudinal direction of the outer cylinder receiving table 3123a inclines against the horizontal direction as shown in FIG. 40B. Thus, the outer cylinder 3040 on the outer cylinder receiving table 3123a will slide down on the outer cylinder receiving table 3123a. At this time, the outer cylinder 3040 slides down with the rear-end first (in other words, the outer cylinder receiving table 3123a rotates in such a manner that the outer cylinder 3040 slides down with its rear-end first). At the front of the lower-end part of the outer cylinder receiving table 3123a in an inclined state, the mount 3160 is in a stand-by state. The outer cylinder 3040 that has slid down the outer cylinder receiving table 3123a is fitted into a circular hole 3161 of the mount 3160 and is mounted on the mount 3160.

<<Structure of Orienting Mechanism 3170>>

Figure 41A:
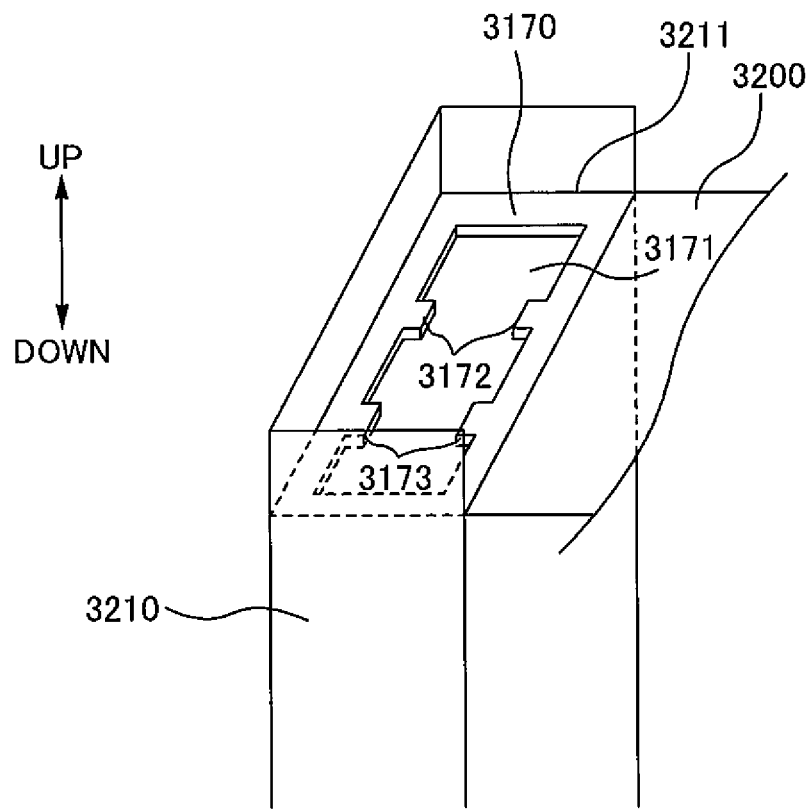
FIG. 41A is a diagram showing the position at which an orienting mechanism 3170 is provided.
Figure 41B:
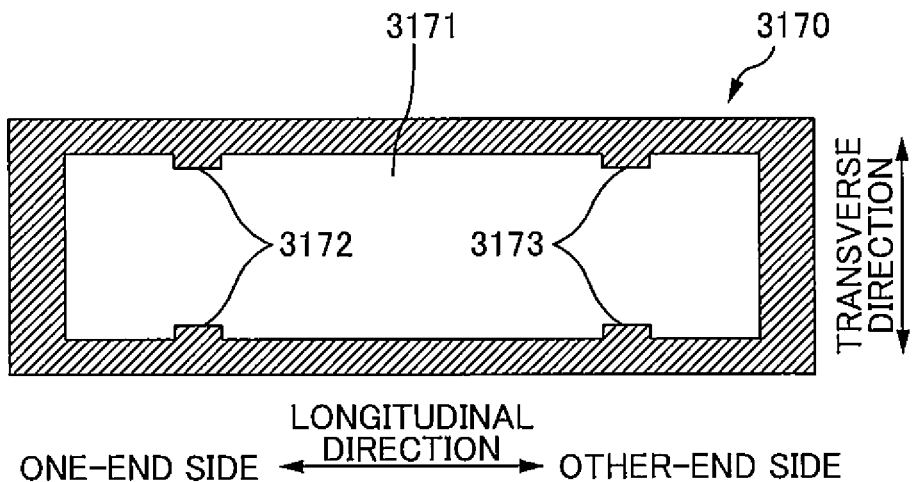
FIG. 41B is a plan view of the orienting mechanism 3170.
Figure 41C:
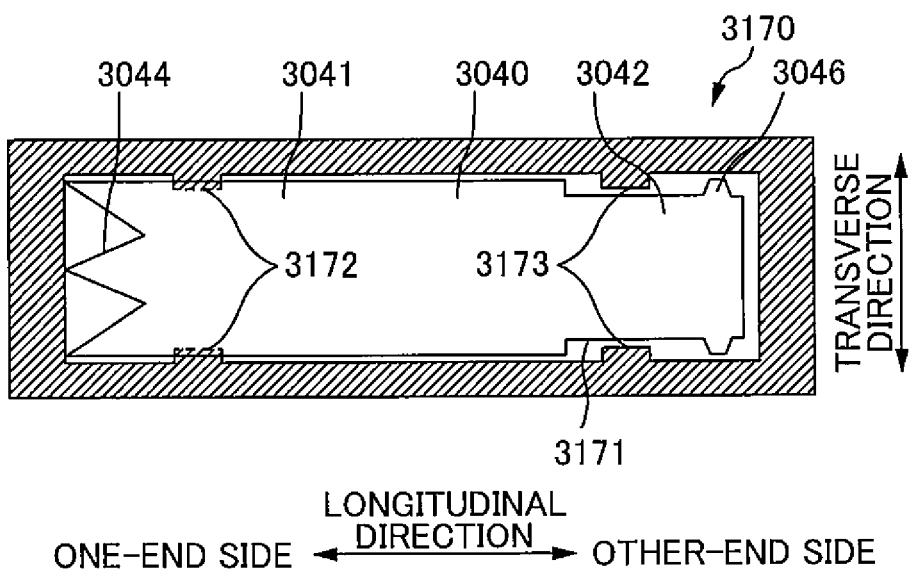
FIG. 41C is a diagram showing how the outer cylinder 3040 passes through a hole 3171 in the orienting mechanism 3170.

Now, the structure of the orienting mechanism 3170 will be described with reference to FIGS. 41A to 41C. FIG. 41A is a diagram showing the position at which the orienting mechanism 3170 is provided. FIG. 41B is a plan view of the orienting mechanism 3170. FIG. 41C is a diagram showing how the outer cylinder 3040 passes through the hole 3171 in the orienting mechanism 3170.

As shown in FIG. 41A, the orienting mechanism 3170 of the present embodiment is a flat plate provided at the opening 3211 of the drop chute 3210 and has substantially the same size as the opening 3211. As shown in FIG. 41B, the orienting mechanism 3170 includes a hole 3171 formed through which the outer cylinder 3040 may pass and a pair of first protruded parts 3172 and a pair of second protruded parts 3173 protruding inwardly into the hole 3171.

The hole 3171 is a rectangular hole 3171 and is formed with a size slightly larger than the contour of the outer cylinder 3040. The outer cylinder 3040 that has traveled on the guide path 3200 is input into the drop chute 3210 by passing through the hole 3171. It is to be noted that as shown in FIG. 41B, the outer cylinder 3040 passes through the hole 3171 in such a manner that the longitudinal direction of the outer cylinder 3040 lies along the longitudinal direction of the hole 3171.

The pair of first protruded parts 3172 is located at one-end side in the longitudinal direction of the hole 3171 and is formed in such a manner that each of the first protruded parts 3172 opposes each other. The pair of second protruded parts 3173 is located at the other-end side in the longitudinal direction of the hole 3171 and is formed in such a manner that each of the second protruded parts 3173 opposes each other. As shown in FIG. 41C, the gap between the pair of first protruded parts 3172 and the gap between the pair of second protruded parts 3173 are greater than the external diameter of the minor diameter part 3042 of the outer cylinder 3040 and is smaller than the external diameter of the major diameter part 3041. The external diameter of the annular rib 3046 of the outer cylinder 3040 is greater than the gap between the pair of first protruded parts 3172 and the gap between the pair of second protruded parts 3173. Accordingly, a part of the outer cylinder 3040 where the major diameter part 3041 and the annular rib 3046 are formed cannot pass between the pair of first protruded parts 3172 and between the pair of second protruded parts 3173. Whereas, the minor diameter part 3042 can pass between the pair of first protruded parts 3172 and between the pair of second protruded parts 3173.

Now, the positional relationship between the outer cylinder 3040 that passes through the hole 3171 and the first protruded part 3172 and the second protruded part 3173 will be described. When the outer cylinder 3040 passes through the hole 3171 in a state shown in FIG. 41C, the first protruded part 3172 and the second protruded part 3173 are located at positions that do not come into contact with the annular rib 3046 in the longitudinal direction of the hole 3171. The first protruded part 3172 is located at a position that comes into contact with the major diameter part 3041 (specifically, a part closer to the rear-end side than the petaloid part 3044). Therefore, the first protruded part 3172 is located at a position where the major diameter part 3041 cannot pass through the pair of first protruded parts 3172. On the other hand, the second protruded part 3173 is located at a position where the minor diameter part 3042 passes through the pair of second protruded parts 3173.

When the outer cylinder 3040 passes through the hole 3171 under such a positional relationship, the major diameter part 3041 cannot pass between the pair of first protruded parts 3172 and the minor diameter part 3042 can pass between the pair of second protruded parts 3173. Thus, the rear-end part of the outer cylinder 3040 will drop first. Thereafter, the outer cylinder 3040 inclines in such a manner that the rear end is located below the leading end. Thereby, the leading-end part of the outer cylinder 3040 will pass through the central part (between the pair of first protruded parts 3172 and the pair of second protruded parts 3173) in the longitudinal direction of the hole 3171. As a result, the rear-end part of the outer cylinder 3040 drops through the drop chute 3210 before the leading-end part. Therefore, the outer cylinder 3040 proceeds from the rear-end part into the first transport path 3220 and travels on the first transport path 3220 with the leading-end part of the outer cylinder 3040 being situated on the upstream side than the rear-end part in the first transport direction.

On the other hand, when the outer cylinder 3040 passes through the hole 3171 with an orientation opposite to the orientation shown in FIG. 41C (the outer cylinder 3040 shown in FIG. 41C is inverted), the minor diameter part 3042 passes between the pair of first protruded parts 3172 and the major diameter part 3041 cannot pass between the pair of second protruded parts 3173. Therefore, in the above-mentioned case, the outer cylinder 3040 drops through the drop chute 3210 with its rear-end part prior to the leading-end part. Thus, the outer cylinder 3040 travels on the first transport path 3220 with the leading-end part being situated on the upstream side of the rear-end part in the first transport direction.

—Structure of Discharging the Outer Cylinder 3040 Out of the Second Transport Path 3230—

In the present embodiment, as has been described above, the outer cylinders 3040 may accumulate on the second transport path 3230. That is to say, because the outer cylinders 3040 are filled in from the starting end of the second transport path 3230 to the terminal end thereof, there may be a case where the outer cylinders 3040 cannot be fitted in anymore on the second transport path 3230. (That is to say, the outer cylinders 3040 may stuff up on the second transport path 3230). Therefore, the outer cylinders 3040 that are newly received by the receiving part 3231 while the outer cylinders 3040 are accumulated from the starting end to the terminal end of the second transport path, are discharged (expelled) from the second transport path 3230.

Before explaining the structure of discharging the outer cylinders 3040 out of the second transport path 3230, the second transport path 3230 will be explained again with reference to FIGS. 42 to 44B.

Figure 43:
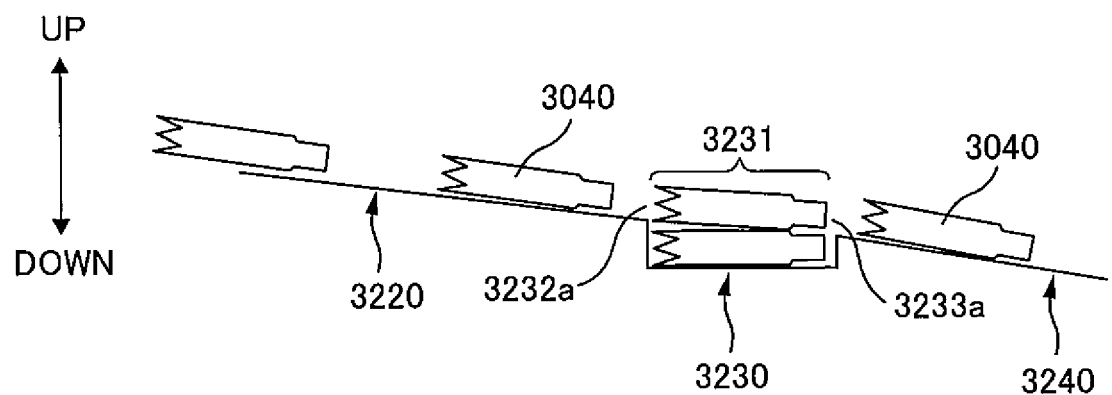
FIG. 43 is a diagram showing a positional relationship in the vertical direction between a first transport path 3220, a second transport path 3230 and a third transport path 3240.
Figure 44A:
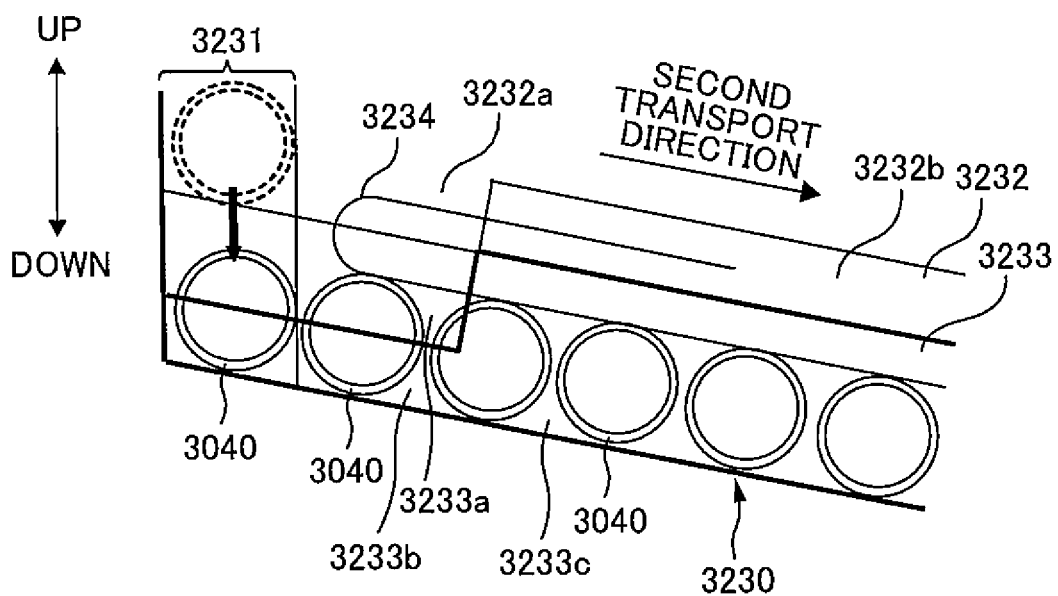
FIGS. 44A and 44B are diagrams showing a state how a receiving part 3231 receives the outer cylinder 3040.
Figure 44B:
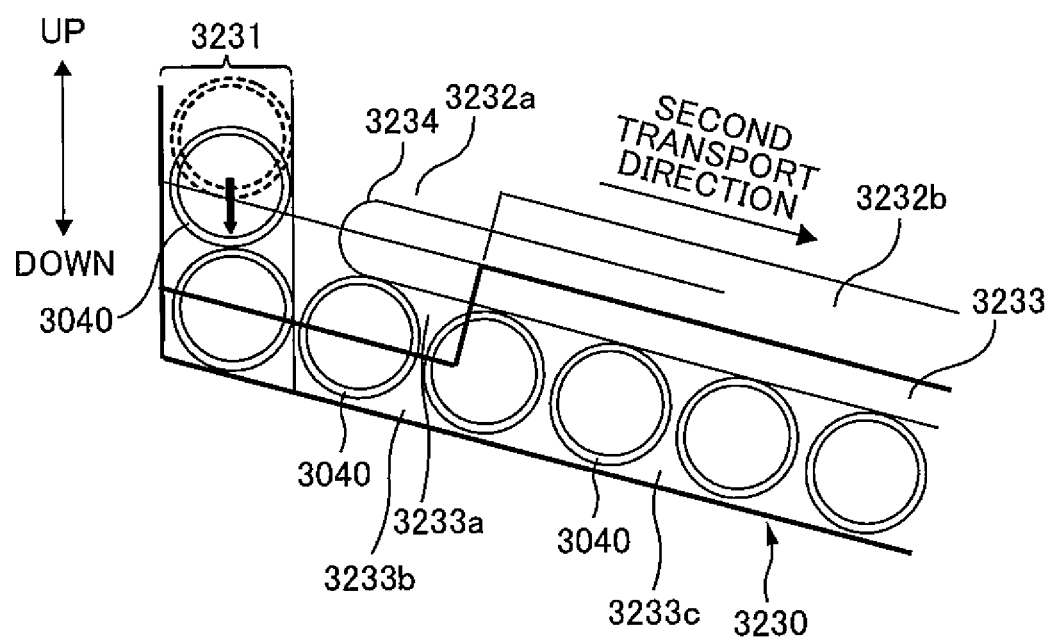

FIG. 42 is an enlarged view of the area labeled "Y" in FIG. 38. FIG. 43 is a diagram showing the positional relationship in the vertical direction between the first transport path 3220, the second transport path 3230 and the third transport path 3240 and viewing such positional relationship in the direction of arrow A shown in FIG. 42. FIGS. 44A and 44B are diagrams showing the state in which the receiving part 3231 receives the outer cylinder 3040 and viewing such a state in the direction of arrow B shown in FIG. 42.

The second transport path 3230 includes the above-mentioned receiving part 3231 at its starting-end part. As shown in FIG. 42, the second transport path 3230 includes a restricting plate 3234 provided at the downstream side of the receiving part 3231 in the second transport direction. This restricting plate 3234 restricts the outer cylinders 3040 on the second transport path 3230 in such a manner that each of the outer cylinder 3040 does not pile up on other outer cylinders 3040. In detail, the gap between the lower surface of the restricting plate 3234 and the bottom surface of the second transport path 3230 is slightly longer than the external diameter of the leading-end part of the outer cylinder 3040 (specifically, approximately 15 mm). The outer cylinder 3040 received by the receiving part 3231 passes between the lower surface of the restricting plate 3234 and the bottom surface of the second transport path 3230 when traveling on the second transport path 3230. As a result, when the outer cylinders 3040 accumulate on the second transport path 3230, each of the outer cylinders 3040 will accumulate without piling up on other outer cylinders 3040.

A part of the restricting plate 3234 that is situated at the most upstream side in the second transport direction is spaced apart from the starting end of the second transport path 3230 (upstream side in the second transport direction) with a distance slightly greater than the external diameter of the major diameter part 3041 of the outer cylinder 3040. On the other hand, the receiving part 3231 is located between the starting end of the second transport path 3230 and the restricting plate 3234 in the second transport direction. That is to say, the receiving part 3231 of the present embodiment is a space formed between the starting end of the second transport path 3230 and the restricting plate 3234 in the second transport direction. The receiving part 3231 has a width, in the second transport direction, capable of accommodating a single outer cylinder 3040 (see FIG. 42). It is to be noted that it is not necessary to provide the restricting plate 3234.

As shown in FIG. 43, the receiving part 3231 of the present embodiment is a recess provided between the terminal end part of the first transport path 3220 and the starting-end part of the third transport path 3240. That is to say, the bottom surface of the starting-end part of the second transport path 3230 is located at a position lower than the bottom surface of each of the terminal end part of the first transport path 3220 and the starting-end part of the third transport path 3240.

The side wall 3232 at the one-end part of the second transport path 3230 (the end part on the side where the outer cylinder 3040 is passed from the first transport path 3220 to the receiving part 3231 in the first transport direction) includes, as has been described above, an inlet 3232a formed thereon. As shown in FIG. 42, the inlet 3232a is a substantially rectangular cutaway part (hereinafter, also referred to as a one-end cutaway part) formed on the upstream side end part of the side wall 3232 in the second transport direction. The first transport path 3220 extends to the one-end cutaway part. It is to be noted that the lateral width of the one-end cutaway part is equal to the lateral width of the terminal end part of the first transport path 3220 and is specifically approximately 33 mm.

The outer cylinder 3040 that has slid down on the first transport path 3220 to the one-end cutaway part drops at the stepped part formed under the one-end cutaway part. A height of the stepped part formed under the cutaway part is a height of a part of the one-end part side wall 3232 of the second transport path 3230 that is located under the one-end cutaway part (that is, the inlet 3232a). In the present embodiment, the height is greater than the external diameter of the leading-end part of the outer cylinder 3040 (that is, the external diameter of the major diameter part 3041) and is less than double the external diameter (specifically, approximately 20 mm).

As has been described above, on the side wall 3233 at the other end part of the second transport path 3230 (the end part opposite to the side where the outer cylinder 3040 is passed from the first transport path 3220 to the receiving part 3231 in the first transport direction), the outlet 3233a is formed. As shown in FIG. 42, the outlet 3233a is also a substantially rectangular cutaway part (hereinafter, also referred to as an other-end cutaway part) formed on the upstream side end part of the side wall 3233 in the second transport direction. The third transport path 3240 extends from the other-end cutaway part. It is to be noted that the lateral width of the other-end cutaway part is equal to the lateral width of the starting-end part of the third transport path 3240 and is specifically approximately 30 mm.

As shown in FIG. 42, a part of the side wall 3233 at the one-end part of the second transport path 3230 that is located under the other-end cutaway part forms a stepped part. A height of the stepped part is less than the external diameter of the leading-end part of the outer cylinder 3040 (that is, the external diameter of the major diameter part 3041) (specifically, approximately 8 mm).

With the above-mentioned structure, the recess that serves as the receiving part 3231 receives the outer cylinder 3040 that has slid down on the first transport path 3220. Also, the recess has a depth in the vertical direction which is capable of holding (keeping inside the recess) a single outer cylinder 3040. That is to say, the outer cylinder 3040 that slides down on the first transport path 3220 while there is no outer cylinder 3040 in the recess drops in the recess and will be held in the recess.

Referring to FIG. 44A, a mechanism of holding the outer cylinder 3040 in the recess will be described. The outer cylinder 3040 that has slid down on the first transport path 3220 while there is no outer cylinder 3040 drops into the recess in a state where it still maintains a momentum acquired by sliding down on the first transport path 3220. It is to be noted that the outer cylinder 3040 drops into the recess in a state where the longitudinal direction of the outer cylinder 3040 is substantially parallel to the first transport direction (in other words, in a state substantially perpendicular to the second transport direction). The outer cylinder 3040 that has dropped into the recess (that is, the outer cylinder 3040 received by the recess) is caught by the side wall 3233 formed at the other end part of the second transport path 3230 and is retained in the recess. In other words, the side wall 3233 formed at the other end part of the second transport path 3230 retains the outer cylinder 3040 that has slid down on the first transport path 3220 while there is no outer cylinder 3040 in the recess into the recess.

In detail, the side wall 3233 formed at the other end part of the second transport path 3230 includes a retaining part 3233b below the other-end cutaway part (that is, the outlet 3233a). This retaining part 3233b catches the outer cylinder 3040 that has slid down on the first transport path 3220 while there is no outer cylinder 3040 in the recess. Then, the outer cylinder 3040 caught by the retaining part 3233b looses the momentum acquired by sliding on the first transport path 3220 and is retained in the recess.

The outer cylinder 3040 is oriented by the orienting mechanism 3170 and travels on the first transport path 3220 in a state where the leading-end part of the outer cylinder 3040 is located in the upstream side of the rear-end part in the first transport direction. Thus, when the outer cylinder 3040 is caught in the retaining part 3233b, the rear end of the outer cylinder 3040 may collide with the retaining part 3233b. If the leading end of the outer cylinder 3040 collides with the retaining part 3233b, the petaloid part 3044 provided at the end part of the leading-end side will bend inwardly. Since the leading-end opening 3043 is narrowed if the petaloid part 3044 is bent inwardly, there arises a disadvantage that it becomes difficult to insert the tampon main body 3020 or inner cylinder 3050 during the step of inserting the tampon main body 3020 or inner cylinder 3050 into the outer cylinder 3040. Whereas, in the present embodiment, such a disadvantage can be overcome since the rear end of the outer cylinder 3040 collides with the retaining part 3233b.

The outer cylinder 3040 that is retained in the recess serving as the receiving part 3231 moves to the downstream side of the second transport path 3230 as the outer cylinder 3040 located on the more downstream side in the second transport path 3230 moves on the second transport path 3230. Thus, there will be no outer cylinder 3040 in the recess and the outer cylinder 3040 that is received by the recess thereafter will be retained in the recess.

The outer cylinder 3040 moves on the second transport path 3230 while being restricted by the sidewalls 3232 and 3233 provided on the second transport path 3230. Specifically, the side wall 3232 formed on the other end part of the second transport path 3230 includes a portion adjacent to the retaining part 3233b in the second transport direction (hereinafter, an adjacent part 3233c). As shown in FIG. 42, the height of the adjacent part 3233c is greater than the external diameter of the leading-end part of the outer cylinder 3040. Also, the side wall 3232 formed on the one end part of the second transport path 3230 includes a part opposing the adjacent part 3233c (hereinafter, an opposing part 3232b). As shown in FIG. 42, the height of the opposing part 3232b is greater than the external diameter of the leading-end part of the outer cylinder 3040. Thus, the outer cylinder 3040 travels between the adjacent part 3233c and the opposing part 3232b when traveling on the second transport path 3230. Thereby, the outer cylinder 3040 traveling on the second transport path 3230 is prevented from falling off from the second transport path 3230.

On the other hand, the outer cylinder 3040 that has slid down on the first transport path 3220 when there is the outer cylinder 3040 in the recess serving as the receiving part 3231 is discharged out of the second transport path 3230 through the outlet 3233a. That is to say, the outer cylinder 3040 received by the recess while the outer cylinders 3040 are accumulated from the starting end to the terminal end of the second transport path 3230 passes by the recess and is passed to the third transport path 3240 through the outlet 3233a. This will be described in detail with reference to FIG. 44B. In the description below, the outer cylinder 3040 that the recess has previously received is referred to as a previous outer cylinder 3040 and the outer cylinder 3040 that slides down on the first transport path 3220 while the previous outer cylinder 3040 is in the recess (that is, the outer cylinder 3040 that the recess subsequently receives) is referred to as a subsequent outer cylinder 3040.

When the subsequent outer cylinder 3040 drops into the recess after passing by the inlet 3232a, it will be stacked on the previous outer cylinder 3040 as shown in FIG. 44B. That is to say, the recess serving as the receiving part 3231 receives the outer cylinder 3040 that has slid down on the first transport path 3220 when the previous outer cylinder 3040 is in the recess (that is, the subsequent outer cylinder 3040) in such a manner that it is stacked on the previous outer cylinder 3040.

The subsequent outer cylinder 3040 that is stacked on the previous outer cylinder 3040 moves in the recess in such a manner that it slides on the previous outer cylinder 3040 (see FIG. 42). At this time, the subsequent outer cylinder 3040 moves in such a manner that the longitudinal direction of the subsequent outer cylinder 3040 lies along the longitudinal direction of the previous outer cylinder 3040. That is to say, even after being received by the recess, the subsequent outer cylinder 3040 keeps on traveling in the direction that it has slid down on the first transport path 3220 (that is, the first transport direction). Thereafter, the subsequent outer cylinder 3040 passes by the outlet 3233a. That is to say, the side wall 3233 formed at the other end part of the second transport path 3230 discharges the subsequent outer cylinder 3040 stacked on the previous outer cylinder 3040 out of the second transport path 3230 through the outlet 3233a.

In detail, the height of the retaining part 3233b formed in the side wall 3233 is less than the external diameter of the leading-end part of the outer cylinder 3040. Thus, the retaining part 3233b can retain the previous outer cylinder 3040 and cannot retain the subsequent outer cylinder 3040 that is stacked on the previous outer cylinder 3040 at the same time. Therefore, since the subsequent outer cylinder 3040 keeps on moving in the recess serving as the receiving part 3231 while maintaining the momentum acquired by sliding down on the first transport path 3220, it will go over the retaining part 3233b and is passed to the third transport path 3240. (That is to say, it is discharged out of the second transport path 3230 through the other-end cutaway part.)

Then, the subsequent outer cylinder 3040 discharged out of the second transport path 3230 will be returned to the outer cylinder feeder 3121 (specifically, the bottom part of the vibratory table 3121a provided in the outer cylinder feeder 3121) by the third transport path 3240 (See FIGS. 38 and 39). In other words, the outer cylinder 3040 discharged out of the second transport path 3230 will be transported towards the first transport path 3220 again by the outer cylinder feeder 3121 and circulates between the outer cylinder feeder 3121 and the transport path 3122 until it moves on the second transport path 3230.

—Effectiveness of Assembling Apparatus 3100 of the Present Embodiment—

According to the assembling apparatus 3100 of the present embodiment, as has been described above, when the supplying mechanism 3120 supplies the outer cylinder 3040, the outer cylinder 3040 received by the receiving part 3231 when there is no outer cylinder 3040 in the receiving part 3231 is retained in the receiving part 3231 by the side wall 3233 formed on the other end part of the second transport path 3230. On the other hand, the outer cylinder received by the receiving part 3231 when there is the outer cylinder 3040 in the receiving part 3231 is discharged out of the second transport path 3230 through the outlet 3233a formed in the side wall 3233. Thus, the outer cylinder 3040 can be supplied properly.

Hereinafter, the effectiveness of the assembling apparatus 3100 of the present embodiment will be described with reference to FIG. 45.

Figure 45:
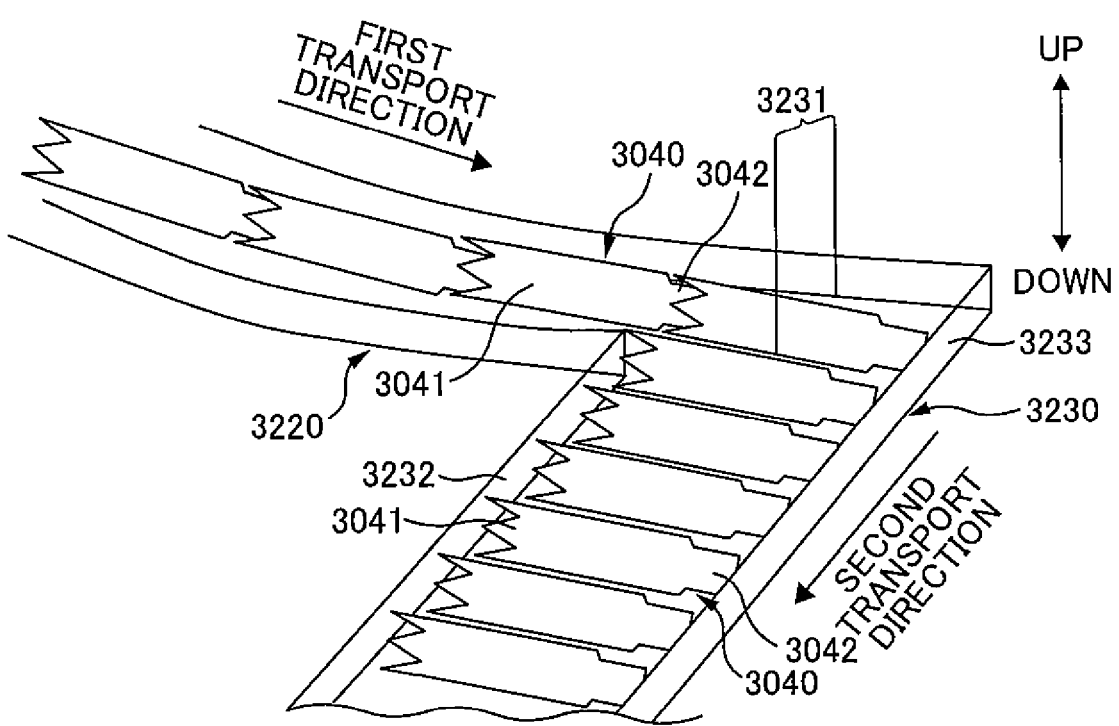
FIG. 45 is a diagram showing the comparison example for explaining the effectiveness of the assembling apparatus 3100 of the present embodiment.

FIG. 45 is a diagram showing the comparison example for explaining the effectiveness of the assembling apparatus 3100 of the present embodiment.

Because of the reasons described above, the outer cylinders 3040 may accumulate on the second transport path 3230 in a side-by-side manner. Further, if the outer cylinders 3040 accumulate from the starting end to the terminating end of the second transport path 3230, the outer cylinder 3040 cannot be accommodated on the second transport path 3230 anymore. That is to say, the outer cylinder 3040 which the receiving part 3231 has received when there is the outer cylinder 3040 in the receiving part 3231 cannot be accommodated on the second transport path 3230 any more.

As for the outer cylinders 3040 that cannot be accommodated on the second transport path 3230 any more, as shown in FIG. 45, the outer cylinders 3040 are gradually piled up before the receiving part 3231 (that is to say, at the terminating end part of the first transport path 3220). At this time, the outer cylinders 3040 pile up in the direction lying along the longitudinal direction of the outer cylinder 3040. Further, the outer cylinder 3040 is oriented by the orienting mechanism 3170 in such a manner that it travels on the first transport path 3220 in a state where the leading-end part of the outer cylinder 3040 is situated on the upstream side than the rear-end part in the first transport direction. As a result, the outer cylinders 3040 that have piled up before the receiving part 3231 will be joined with each other, as shown in FIG. 45. That is to say, the above-mentioned jamming occurs before the receiving part 3231. With the outer cylinders 3040 being joined to each other, each outer cylinder 3040 cannot be supplied individually and thus each of the outer cylinders 3040 will not be properly set on the assembling conveyor 3110. As a result, the manufacturing speed of the tampon 3010 may be lowered.

On the contrary, according to the present embodiment, when there is a spatial allowance for accommodating the outer cylinders 3040 on the second transport path 3230 (that is to say, when there are no outer cylinders 3040 on the receiving part 3231), the outer cylinder 3040 that is passed from the first transport path 3220 is retained in the receiving part 3231. On the other hand, the outer cylinder 3040 that was passed when the outer cylinders 3040 cannot be accommodated on the second transport path 3230 anymore (that is to say, when there are the outer cylinder 3040 in the receiving part 3231) is discharged out of the second transport path 3230.

As has been described above, in the present embodiment, depending on the state in which how the outer cylinders 3040 are accommodated on the second transport path 3230, the outer cylinder 3040 newly passed to the second transport path 3230 from the first transport path 3220 can be transported to a proper transport destination. As a result, the outer cylinders 3040 can be avoided from being piled up before the receiving part 3231 and thus the problem illustrated in FIG. 45, in other words the jamming in front of the receiving part 3231, can be eliminated. Therefore, with the assembling apparatus 3100 of the present embodiment, the outer cylinders 3040 can be appropriately supplied individually and the tampon 3010 can be manufactured efficiently.

It is to be noted that in the present embodiment, the internal diameter of the leading-end part of the outer cylinder 3040 (that is to say, the major diameter part 3041) is greater than the external diameter of the rear-end part (that is to say, the minor diameter part 3042). In such a case, the rear-end part of the other outer cylinder 3040 can be easily caught into the leading-end part of the outer cylinder 3040 and thus may easily cause the above-mentioned jamming. It is to be noted that when the internal diameter of the leading-end part of the outer cylinder 3040 is the same as or even smaller than the external diameter of the rear-end part, if the petaloid parts 3044 incline outwards and the leading-end opening 3043 broadens, the rear-end part may get caught in the leading-end part. That is to say, even if the internal diameter of the leading-end part of the outer cylinder 3040 is the same as or even smaller than the external diameter of the rear-end part, the jamming could occur and thus the assembling apparatus 3100 of the present embodiment is effective.

In the present embodiment, each of the first transport path 3220 and the third transport path 3240 is inclined in such a manner that the outer cylinder 3040 slides down on each of them and the receiving part 3231 is a recess between the first transport path 3220 and the third transport path 3240. With such a structure, the outer cylinder 3040 that slides down on the first transport path 3220 when there is the outer cylinder 3040 in the recess is discharged out of the second transport path 3230 by using the momentum acquired by sliding down on the first transport path 3220. Thus, the outer cylinder 3040 can be properly discharged out of the second transport path 3230 without separately providing a device for discharging the outer cylinder 3040 out of the second transport path 3230.

—Other Embodiment—

In each of the embodiments described above, the manufacturing method and manufacturing device (assembling apparatus 3100) of the present invention has been mainly described, but the above-embodiments are solely for facilitating the understanding of the present invention and by no means regarded as limitations on the present invention. The invention can of course be altered and improved without departing from the gist thereof and equivalents are intended to be embraced therein. Also, the above-mentioned setting values, sizes and configurations, etc., are merely an example provided to show the effect of the present invention and is not to be interpreted as limiting the invention.

In the above-mentioned embodiment, the tampon 3010 having the inner cylinder 3050 of a two-tier structure (in other words, extendable inner cylinder 3050) as a pushing member has been described, but the present invention is not limited thereto. For example, it can be a tampon 3010 having the inner cylinder 3050 with a fixed length (which does not extend or contract).

Also, in the above-mentioned embodiment, although the outer cylinder 3040 including the major diameter part 3041 and the minor diameter part 3042 has been described, the outer cylinder 3040 may be without the minor diameter part 3042. That is to say, the external diameter and the internal diameter may be the same between the leading-end part (one-end part in the longitudinal direction) and the rear-end part (other-end part in the longitudinal direction).

Also, in the above-mentioned embodiment, the outer cylinder 3040 that has traveled on the second transport path 3230 is passed from the second transport path 3230 to the assembling conveyor 3110 (specifically, the mount 3160 placed on the assembling conveyor 3110) via the outer cylinder setting part 3123. That is to say, in the above-mentioned embodiment, the second transport path 3230 is a part of the transport path 3122 that is nearest to the assembling conveyor 3110, but is not limited thereto. The second transport path 3230 may be a portion of the transport path 3122 that is not nearest to the assembling conveyor 3110 and can be, for example, apart that is midway on the transport path 3122.

LIST OF REFERENCE NUMERALS

1001 tampon, 1004 tampon main body, 1005 absorbent body,
1008 cord, 1010 applicator,
1011 outer cylinder (accommodating member),
1012 minor diameter part, 1013 major diameter part,
1014 leading-end opening, 1015 petaloid part, 1016 rear-end opening,
1017 annular protrusion, 1018 stepped part,
1020 inner cylinder (pushing member), 1021 first inner cylinder,
1022 flange part, 1023 annular protrusion, 1025 second inner cylinder,
1026 flange part, 1027 protruded part, 1028 flared part,
1040 assembling apparatus (apparatus for manufacturing tampon),
1041 outer cylinder supplying part,
1042 outer cylinder transport feeder, 1042a vibratory table,
1043 transport path, 1044 accumulating part, 1045 drop chute,
1046 accumulating part, 1050 transport conveyor,
1051 first inner cylinder supplying part,
1052 second inner cylinder supplying part,
1053 inner cylinder transport feeder,
1053a vibratory table, 1054 transport tube (first inserting mechanism),
1055 rail, 1060 orientation orienting mechanism (orienting mechanism),
1061 orienting plate, 1062 opening, 1062a one-end opening,
1062b center opening, 1062c other-end opening,
1063 first protruded part, 1064 second protruded part,
1067 first jet part, 1067a nozzle, 1068 second jet part,
1068a nozzle,
1070 tampon main body inserting part (second inserting mechanism),
1071 guide part, 1072 pin, 1081 transport roller,
1082 transport roller, 1084 bent part,
2010 tampon, 2020 tampon main body, 2021 cotton body, 2022 cord,
2030 applicator, 2040 outer cylinder (accommodating cylinder),
2041 major diameter part, 2042 minor diameter part,
2043 leading-end opening (opening), 2044 petaloid part,
2045 rear-end opening, 2046 annular rib, 2047 stepped part,
2050 inner cylinder (pushing member), 2051 first inner cylinder,
2051a flange part, 2051b annular protrusion,
2052 second inner cylinder, 2052a flange part,
2052b protruded part, 2052c flared part,
2100 assembling apparatus (apparatus for manufacturing tampon 2010),
2110 transport conveyor, 2120 outer cylinder supplying mechanism,
2121 outer cylinder transport feeder, 2121a vibratory table,
2122 transport path, 2122a accumulating part, 2122b drop chute,
2122c accumulating part,
2130 inner cylinder inserting mechanism (pushing member inserting mechanism), 2131 first inner cylinder inserting mechanism,
2132 second inner cylinder inserting mechanism,
2133 inner cylinder transport feeder, 2133a vibratory table,
2133b rail, 2134 supplying tube, 2135 inner cylinder inserting part,
2135a pressing member, 2140 tampon main body inserting mechanism,
2141 guide tube, 2142 suction device, 2143 pressing member,
2150 broadening mechanism, 2151 first pusher unit,
2152 second pusher unit, 2153 third pusher unit, 2160 mount,
2160 mounting jig, 2200, 2210 pusher (jig),
2201, 2211 tapered part,
2201a, 2211a outer peripheral surface,
2202, 2212 projected part,
2202a, 2212a projected surface (surface at the leading end of the projected part 2002 and projecting towards outside than the outer edge of the rear end of the tapered part 2201),
2220 attachment plate, 2230 auxiliary pusher (other jig),
2231 other tapered part, 2231a outer peripheral surface,
3010 tampon,
3020 tampon main body, 3031 cotton body, 3022 cord, 3030 applicator,
3040 outer cylinder (accommodating cylinder), 3041 major diameter part,
3042 minor diameter part, 3043 leading-end opening (opening),
3044 petaloid part, 3045 rear-end opening, 3046 annular rib,
3047 stepped part, 3050 inner cylinder (pushing member),
3051 first inner cylinder, 3051a flange part,
3051b annular protrusion, 3052 second inner cylinder, 3052a flange part, 3052b protruded part, 3052c flared part,
3100 assembling apparatus (apparatus for manufacturing tampon 3010),
3110 assembling conveyor, 3120 supplying mechanism,
3121 outer cylinder feeder (parts feeder),
3121a vibratory table (placing table),
3122 transport path, 3123 outer cylinder setting part,
3123a outer cylinder receiving table, 3130 inserting mechanism,
3140 inner cylinder inserting mechanism,
3141 first inner cylinder inserting mechanism,
3142 second inner cylinder inserting mechanism,
3143 inner cylinder feeder, 3143a vibratory table,
3143b rail, 3144 tube, 3145 inner cylinder pushing device,
3145a pressing jig, 3150 tampon main body inserting mechanism,
3151 guide tube, 3152 suction device,
3153 tampon main body pressing device,
3160 mount, 3161 hole,
3170 orienting mechanism, 3171 hole,
3172 first protruded part, 3173 second protruded part,
3200 guide path, 3210 drop chute, 3211 opening,
3220 first transport path, 3230 second transport path,
3231 receiving part, 3232 side wall, 3232a inlet,
3232b opposing part, 3233 side wall, 3233a outlet,
3233b retaining part,
3233c adjacent part (part adjacent to retaining part 3233b in the second transport direction),
3234 restricting plate, 3240 third transport path

The invention claimed is:

1. An apparatus for manufacturing a tampon, the tampon including an absorbent body for absorbing liquid, an accommodating member that is cylindrical and accommodates the absorbent body, and a pushing member that is configured to move inside the accommodating member and push the absorbent body out of the accommodating member, the accommodating member including a minor diameter part provided at a first end thereof and a major diameter part provided at a second end thereof, the major diameter part having an external diameter greater than that of the minor diameter part, the major diameter part, at a leading end thereof, including a plurality of petaloid parts, said apparatus comprising:
an orienting mechanism configured to orient the accommodating member;
a first inserting mechanism configured to insert the pushing member into the accommodating member oriented by the orienting mechanism; and
a second inserting mechanism configured to insert the absorbent body into the accommodating member in which the pushing member is inserted,
the orienting mechanism including:
an opening through which the accommodating member is inputted;
a pair of first protruded parts located on a first side in a longitudinal direction of the opening and protruding inwardly in an opposing manner into the opening; and
a pair of second protruded parts located on a second side in the longitudinal direction of the opening and protruding inwardly in an opposing manner into the opening,
a gap between the pair of first protruded parts configured to be greater than the external diameter of the minor diameter part and smaller than the external diameter of the major diameter part, and
a gap between the pair of second protruded parts configured to be greater than the external diameter of the minor diameter part and smaller than the external diameter of the major diameter part,
wherein
when the opening of the orienting mechanism receives the accommodating member in a manner that a longitudinal direction of the accommodating member lies along the longitudinal direction of the opening,
one of the pair of first protruded parts and the pair of second protruded parts is positioned where the minor diameter part passes between said one of the pair of first protruded parts and the pair of second protruded parts, and
the other of the pair of first protruded parts and the pair of second protruded parts is positioned (a) where the major diameter part cannot pass between said other of the pair of first protruded parts and the pair of second protruded parts and (b) to contact with a part of the accommodating member that is nearer to a center of the accommodating member in the longitudinal direction than the petaloid parts.

2. An apparatus according to claim 1, wherein, when the opening of the orienting mechanism receives the accommodating member in such a manner that the longitudinal direction of the accommodating member lies along the longitudinal direction of the opening,
the other of the pair of first protruded parts and the pair of second protruded parts is positioned to contact with the part of the accommodating member that is closer to the petaloid parts than to the center of the accommodating member in the longitudinal direction.

3. An apparatus according claim 1, wherein
the accommodating member includes an annular protrusion provided nearer to the first end than the minor diameter part,
the gap between the pair of first protruded parts and the gap between the pair of second protruded parts are configured to be smaller than an external diameter of the annular protrusion, and
when the opening of the orienting mechanism receives the accommodating member in such a manner that the longitudinal direction of the accommodating member lies along the longitudinal direction of the opening,
the one of the pair of first protruded parts and the pair of second protruded parts is positioned to not come into contact with the annular protrusion.

4. An apparatus according to claim 1, wherein the orienting mechanism further includes:
a first jet part that is provided at a position opposing the first protruded parts and configured to inject air towards the first protruded parts; and
a second jet part that is provided at a position opposing the second protruded parts and configured to inject air towards the second protruded parts.

5. An apparatus according to claim 1, further comprising:
a transport path configured to transport the accommodating member and to input the accommodating member into the opening,
wherein
the transport path has an accumulating part configured to accumulate a plurality of accommodating members in a side-by-side manner, and
the transport path is configured to input the accommodating members accumulated in the accumulating part one-by-one into the opening in such a manner that the major diameter part of the inputted accommodating member comes into contact with said one of the pair of first protruded parts and the pair of second protruded parts.

6. An apparatus according to claim 1, wherein
the opening has a rectangular shape, and
a distance in the longitudinal direction between an edge of the opening on the first side and the first protruded parts is equal to a distance in the longitudinal direction between an edge of the opening on the second side and the second protruded parts.

* * * * *